(12) United States Patent
Cuti et al.

(10) Patent No.: US 11,701,162 B2
(45) Date of Patent: Jul. 18, 2023

(54) SMART BLADE APPLICATION FOR REUSABLE AND DISPOSABLE DEVICES

(71) Applicant: Ethicon LLC, Guaynabo, PR (US)

(72) Inventors: Alexander R. Cuti, Pittsburgh, PA (US); Matthew S. Schneider, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 1015 days.

(21) Appl. No.: 16/144,478

(22) Filed: Sep. 27, 2018

(65) Prior Publication Data

US 2019/0274714 A1   Sep. 12, 2019

Related U.S. Application Data

(60) Provisional application No. 62/640,415, filed on Mar. 8, 2018.

(51) Int. Cl.
*A61B 17/32* (2006.01)
*A61B 18/12* (2006.01)
(Continued)

(52) U.S. Cl.
CPC ........ *A61B 18/1206* (2013.01); *A61B 8/4483* (2013.01); *A61B 8/56* (2013.01);
(Continued)

(58) Field of Classification Search
CPC .............. A61B 17/32; A61B 17/00234; A61B 17/320092; A61B 17/320068;
(Continued)

(56) References Cited

U.S. PATENT DOCUMENTS 1,853,416 A   4/1932   Hall
2,222,125 A   11/1940  Stehlik
(Continued)

FOREIGN PATENT DOCUMENTS

AU   2015201140 A1   3/2015
CA   2795323 A1      5/2014
(Continued)

OTHER PUBLICATIONS

US 10,504,709, 08/2018, Karancsi et al. (withdrawn).
(Continued)

*Primary Examiner* — Vi X Nguyen

(57) ABSTRACT

An ultrasonic device may include an electromechanical system defined by a resonant frequency and further include an ultrasonic transducer coupled to an ultrasonic blade. The device may be composed of two or more components, one of which is reusable and one of which is disposable. A method of detecting a proper installation of the components may include determining a spectroscopy signature of the blade coupled to the transducer, comparing the signature to a reference signature, determining an installation state of the components based on the comparison, and controlling a delivery of power to the transducer based on the comparison. The method may include enabling an operation of the device when the installation state of components is proper. The method may further include disabling the device when the installation state is not proper and generating a warning. The warning may be visible, audible, or tactile.

16 Claims, 32 Drawing Sheets

(51) Int. Cl.

| | | |
|---|---|---|
| *A61B 18/14* | (2006.01) | |
| *A61B 17/3211* | (2006.01) | |
| *A61B 8/00* | (2006.01) | |
| *B06B 1/06* | (2006.01) | |
| *H03H 9/00* | (2006.01) | |
| *A61B 90/00* | (2016.01) | |
| *G05B 19/05* | (2006.01) | |
| *A61B 17/00* | (2006.01) | |
| *A61B 18/00* | (2006.01) | |
| *A61B 17/28* | (2006.01) | |
| *A61B 34/30* | (2016.01) | |
| *A61B 17/29* | (2006.01) | |

(52) U.S. Cl.
CPC .... *A61B 17/00234* (2013.01); *A61B 17/3211* (2013.01); *A61B 17/320068* (2013.01); *A61B 17/320092* (2013.01); *A61B 18/1442* (2013.01); *A61B 18/1445* (2013.01); *A61B 90/08* (2016.02); *B06B 1/0644* (2013.01); *G05B 19/058* (2013.01); *H03H 9/0004* (2013.01); *A61B 17/282* (2013.01); *A61B 34/30* (2016.02); *A61B 2017/0003* (2013.01); *A61B 2017/00017* (2013.01); *A61B 2017/00022* (2013.01); *A61B 2017/0023* (2013.01); *A61B 2017/00039* (2013.01); *A61B 2017/00061* (2013.01); *A61B 2017/0084* (2013.01); *A61B 2017/00106* (2013.01); *A61B 2017/00119* (2013.01); *A61B 2017/00154* (2013.01); *A61B 2017/00185* (2013.01); *A61B 2017/00199* (2013.01); *A61B 2017/00221* (2013.01); *A61B 2017/00398* (2013.01); *A61B 2017/00477* (2013.01); *A61B 2017/00482* (2013.01); *A61B 2017/2927* (2013.01); *A61B 2017/32007* (2017.08); *A61B 2017/320071* (2017.08); *A61B 2017/320074* (2017.08); *A61B 2017/320084* (2013.01); *A61B 2017/320094* (2017.08); *A61B 2017/320095* (2017.08); *A61B 2017/320097* (2017.08); *A61B 2018/0063* (2013.01); *A61B 2018/00589* (2013.01); *A61B 2018/00595* (2013.01); *A61B 2018/00601* (2013.01); *A61B 2018/00619* (2013.01); *A61B 2018/00684* (2013.01); *A61B 2018/00791* (2013.01); *A61B 2018/00827* (2013.01); *A61B 2018/00875* (2013.01); *A61B 2018/00892* (2013.01); *A61B 2018/00994* (2013.01); *A61B 2018/126* (2013.01); *A61B 2018/128* (2013.01); *A61B 2018/1253* (2013.01); *A61B 2018/1455* (2013.01); *A61B 2090/0804* (2016.02); *A61B 2090/0807* (2016.02); *A61B 2090/0808* (2016.02); *A61B 2090/0809* (2016.02); *A61B 2217/005* (2013.01); *A61B 2218/002* (2013.01); *A61B 2218/008* (2013.01); *G05B 2219/14074* (2013.01)

(58) Field of Classification Search
CPC ......... A61B 2017/320072; A61B 2017/00119; A61B 90/00; A61B 90/08
See application file for complete search history.

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |

(56) References Cited

U.S. PATENT DOCUMENTS

| | | |
|---|---|---|
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |

(56) References Cited

U.S. PATENT DOCUMENTS

| | | |
|---|---|---|
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |

(56) References Cited

U.S. PATENT DOCUMENTS

| | | |
|---|---|---|
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |

(56) References Cited

U.S. PATENT DOCUMENTS

| | | |
|---|---|---|
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |

(56) References Cited

U.S. PATENT DOCUMENTS

| | | |
|---|---|---|
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |

(56) References Cited

U.S. PATENT DOCUMENTS

| | | |
|---|---|---|
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondon et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |

(56) References Cited

U.S. PATENT DOCUMENTS

| | | |
|---|---|---|
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |

(56) References Cited

U.S. PATENT DOCUMENTS

| | | |
|---|---|---|
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,413 B2 | 12/2019 | Schepis et al. |
| 10,512,461 B2 | 12/2019 | Gupta et al. |
| 10,512,499 B2 | 12/2019 | McHenry et al. |

(56) References Cited

U.S. PATENT DOCUMENTS

| | | |
|---|---|---|
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savaii et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |

(56) References Cited

U.S. PATENT DOCUMENTS

| | | |
|---|---|---|
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,784 B2 | 3/2021 | Mozdzierz et al. |
| 10,950,982 B2 | 3/2021 | Regnier et al. |
| 11,000,276 B2 | 5/2021 | Shelton, IV et al. |
| 11,051,817 B2 | 7/2021 | Shelton, IV et al. |
| 11,058,501 B2 | 7/2021 | Tokarchuk et al. |
| 11,071,595 B2 | 7/2021 | Johnson et al. |
| 11,141,213 B2 | 10/2021 | Yates et al. |
| 11,185,325 B2 | 11/2021 | Shelton, IV et al. |
| 11,218,822 B2 | 1/2022 | Morgan et al. |
| D950,728 S | 5/2022 | Bakos et al. |
| D952,144 S | 5/2022 | Boudreaux |
| 11,350,978 B2 | 6/2022 | Henderson et al. |
| 2001/0056237 A1 | 12/2001 | Cane et al. |
| 2002/0049551 A1 | 4/2002 | Friedman et al. |
| 2002/0052616 A1* | 5/2002 | Wiener .......... A61B 17/320068 606/169 |
| 2002/0072746 A1 | 6/2002 | Lingenfelder et al. |
| 2002/0138642 A1 | 9/2002 | Miyazawa et al. |
| 2002/0169584 A1 | 11/2002 | Fu et al. |
| 2003/0009111 A1 | 1/2003 | Cory et al. |
| 2003/0018329 A1 | 1/2003 | Hooven |
| 2003/0046109 A1 | 3/2003 | Uchikubo |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |

(56) References Cited

U.S. PATENT DOCUMENTS

| | | |
|---|---|---|
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0167644 A1* | 7/2008 | Shelton ............ A61B 17/07207 606/34 |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0234708 A1 | 9/2008 | Houser et al. |
| 2008/0235052 A1 | 9/2008 | Node-Langlois et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0306581 A1 | 12/2009 | Claus |
| 2009/0307681 A1 | 12/2009 | Armado |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |

(56) References Cited

U.S. PATENT DOCUMENTS

| | | |
|---|---|---|
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0197531 A1 | 8/2013 | Boukhny et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William et al. |
| 2014/0117256 A1 | 5/2014 | Mueller et al. |
| 2014/0121669 A1 | 5/2014 | Claus |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276749 A1 | 9/2014 | Johnson |
| 2014/0287393 A1 | 9/2014 | Kumar et al. |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0057675 A1 | 2/2015 | Akeel et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282821 A1 | 10/2015 | Look et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |

(56) References Cited

U.S. PATENT DOCUMENTS

| | | |
|---|---|---|
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0184054 A1 | 6/2016 | Lowe |
| 2016/0192960 A1 | 7/2016 | Bueno et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0270861 A1 | 9/2016 | Guru et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | McHenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0156076 A1 | 6/2017 | Eom et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0173262 A1 | 6/2017 | Veltz |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153436 A1 | 6/2018 | Olson |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |

(56) References Cited

U.S. PATENT DOCUMENTS

| | | |
|---|---|---|
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0315492 A1 | 11/2018 | Bishop et al. |
| 2018/0317826 A1 | 11/2018 | Muhsin et al. |
| 2018/0317916 A1 | 11/2018 | Wixey |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0351987 A1 | 12/2018 | Patel et al. |
| 2018/0353186 A1 | 12/2018 | Mozdzierz et al. |
| 2018/0357383 A1 | 12/2018 | Allen et al. |
| 2018/0360454 A1 | 12/2018 | Shelton, IV et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159777 A1 | 5/2019 | Ehrenfels et al. |
| 2019/0159778 A1 | 5/2019 | Shelton, IV et al. |
| 2019/0162179 A1 | 5/2019 | O'Shea et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |

(56) References Cited

U.S. PATENT DOCUMENTS

| | | |
|---|---|---|
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207911 A1 | 7/2019 | Wiener et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |

(56) References Cited

U.S. PATENT DOCUMENTS

| | | |
|---|---|---|
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzad et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0160438 A1 | 5/2022 | Shelton, IV et al. |
| 2022/0175374 A1 | 6/2022 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 2037167 A1 | 7/1980 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |

(56) References Cited

FOREIGN PATENT DOCUMENTS

| | | |
|---|---|---|
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2509523 A | 7/2014 |
| JP | S5373315 A | 6/1978 |
| JP | 2001029353 A | 2/2001 |
| JP | 2007123394 A | 5/2007 |
| JP | 2010057642 A | 3/2010 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015129395 A1 | 9/2015 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

(56) References Cited

OTHER PUBLICATIONS

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence—Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode," Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?v=UIdQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgicai_devices.pdf.
Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Lalys, et al., "Automatic knowledge-based recognition of low-level tasks in ophthalmological procedures", Int J Cars, vol. 8, No. 1, pp. 1-49, Apr. 19, 2012.
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

\* cited by examiner

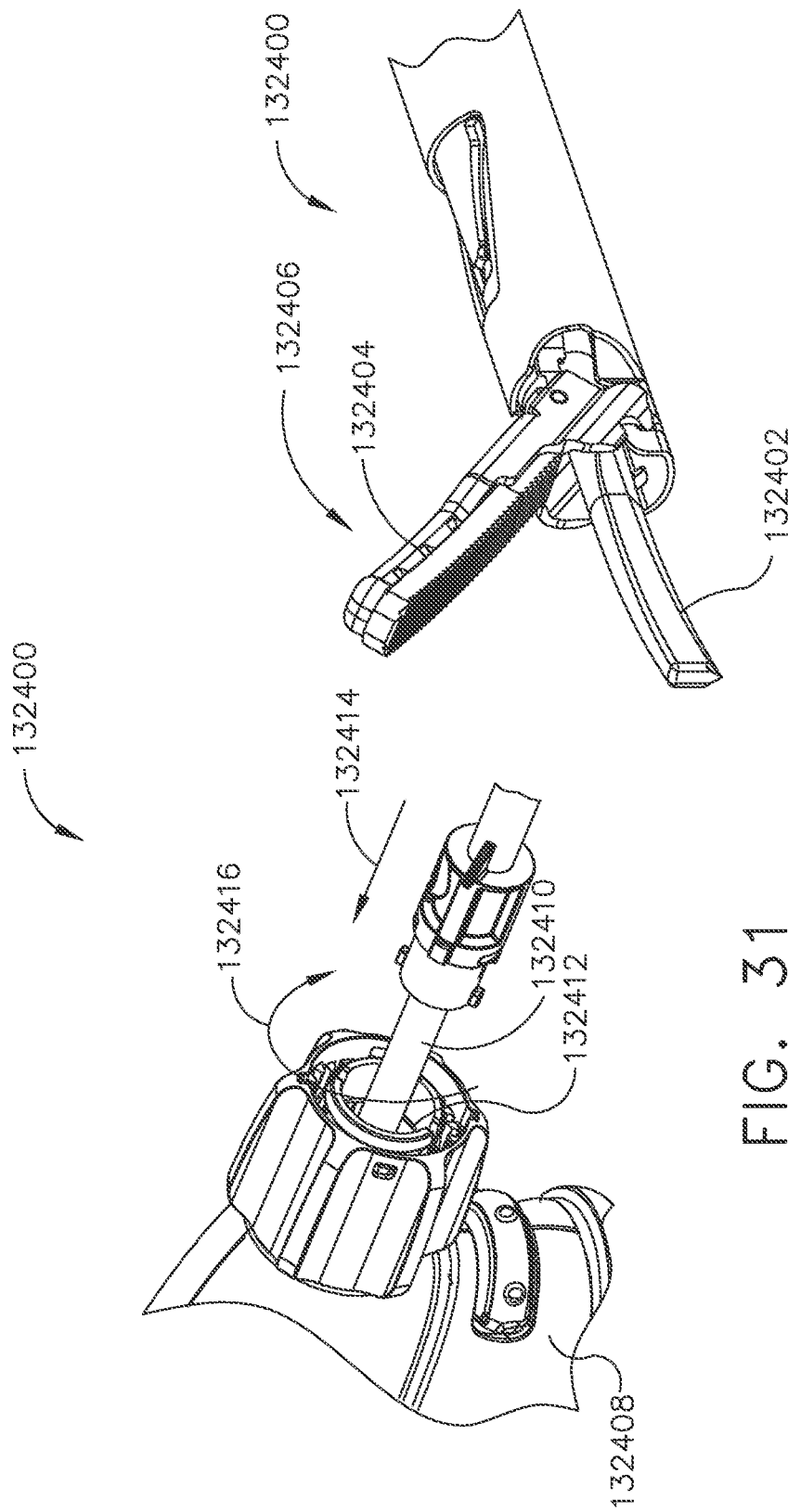

SMART BLADE APPLICATION FOR REUSABLE AND DISPOSABLE DEVICES

CROSS-REFERENCE TO RELATED APPLICATION

This application claims the benefit of priority under 35 U.S.C. § 119(e) to U.S. Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of which is herein incorporated by reference in its entirety.

BACKGROUND

In a surgical environment, smart energy devices may be needed in a smart energy architecture environment. Ultrasonic surgical devices, such as ultrasonic scalpels, are finding increasingly widespread applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device may comprise a handpiece containing an ultrasonic transducer, and an instrument coupled to the ultrasonic transducer having a distally-mounted end effector (e.g., a blade tip) to cut and seal tissue. In some cases, the instrument may be permanently affixed to the handpiece. In other cases, the instrument may be detachable from the handpiece, as in the case of a disposable instrument or an interchangeable instrument. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures and can be transmitted to the end effector by an ultrasonic generator in communication with the handpiece. Vibrating at high frequencies (e.g., 55,500 cycles per second), the ultrasonic blade denatures protein in the tissue to form a sticky coagulum. Pressure exerted on tissue by the blade surface collapses blood vessels and allows the coagulum to form a hemostatic seal. A surgeon can control the cutting speed and coagulation by the force applied to the tissue by the end effector, the time over which the force is applied, and the selected excursion level of the end effector.

The ultrasonic transducer may be modeled as an equivalent circuit comprising a first branch having a static capacitance and a second "motional" branch having a serially connected inductance, resistance and capacitance that define the electromechanical properties of a resonator. Known ultrasonic generators may include a tuning inductor for tuning out the static capacitance at a resonant frequency so that substantially all of a generator's drive signal current flows into the motional branch. Accordingly, by using a tuning inductor, the generator's drive signal current represents the motional branch current, and the generator is thus able to control its drive signal to maintain the ultrasonic transducer's resonant frequency. The tuning inductor may also transform the phase impedance plot of the ultrasonic transducer to improve the generator's frequency lock capabilities. However, the tuning inductor must be matched with the specific static capacitance of an ultrasonic transducer at the operational resonant frequency. In other words, a different ultrasonic transducer having a different static capacitance requires a different tuning inductor.

Additionally, in some ultrasonic generator architectures, the generator's drive signal exhibits asymmetrical harmonic distortion that complicates impedance magnitude and phase measurements. For example, the accuracy of impedance phase measurements may be reduced due to harmonic distortion in the current and voltage signals.

Moreover, electromagnetic interference in noisy environments decreases the ability of the generator to maintain lock on the ultrasonic transducer's resonant frequency, increasing the likelihood of invalid control algorithm inputs.

Electrosurgical devices for applying electrical energy to tissue in order to treat and/or destroy the tissue are also finding increasingly widespread applications in surgical procedures. An electrosurgical device may comprise a handpiece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

Electrical energy applied by an electrosurgical device can be transmitted to the instrument by a generator in communication with the handpiece. The electrical energy may be in the form of radio frequency (RF) energy. RF energy is a form of electrical energy that may be in the frequency range of 300 kHz to 1 MHz, as described in EN60601-2-2:2009+A11:2011, Definition 201.3.218—HIGH FREQUENCY. For example, the frequencies in monopolar RF applications are typically restricted to less than 5 MHz. However, in bipolar RF applications, the frequency can be almost any value. Frequencies above 200 kHz are typically used for monopolar applications in order to avoid the unwanted stimulation of nerves and muscles which would result from the use of low frequency current. Lower frequencies may be used for bipolar techniques if a risk analysis shows the possibility of neuromuscular stimulation has been mitigated to an acceptable level. Normally, frequencies above 5 MHz are not used in order to minimize the problems associated with high frequency leakage currents. It is generally recognized that 10 mA is the lower threshold of thermal effects on tissue.

During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Due to their unique drive signal, sensing and feedback needs, ultrasonic and electrosurgical devices have generally required different generators. Additionally, in cases where the instrument is disposable or interchangeable with a handpiece, ultrasonic and electrosurgical generators are limited in their ability to recognize the particular instrument configuration being used and to optimize control and diagnostic processes accordingly. Moreover, capacitive coupling between the non-isolated and patient-isolated circuits of the generator, especially in cases where higher voltages and frequencies are used, may result in exposure of a patient to unacceptable levels of leakage current.

Furthermore, due to their unique drive signal, sensing and feedback needs, ultrasonic and electrosurgical devices have generally required different user interfaces for the different generators. In such conventional ultrasonic and electrosurgical devices, one user interface is configured for use with an ultrasonic instrument whereas a different user interface may be configured for use with an electrosurgical instrument. Such user interfaces include hand and/or foot activated user interfaces such as hand activated switches and/or foot activated switches. As various aspects of combined generators for use with both ultrasonic and electrosurgical instruments are contemplated in the subsequent disclosure, additional user interfaces that are configured to operate with both ultrasonic and/or electrosurgical instrument generators also are contemplated.

Additional user interfaces for providing feedback, whether to the user or other machine, are contemplated within the subsequent disclosure to provide feedback indicating an operating mode or status of either an ultrasonic and/or electrosurgical instrument. Providing user and/or machine feedback for operating a combination ultrasonic and/or electrosurgical instrument will require providing sensory feedback to a user and electrical/mechanical/electromechanical feedback to a machine. Feedback devices that incorporate visual feedback devices (e.g., an LCD display screen, LED indicators), audio feedback devices (e.g., a speaker, a buzzer) or tactile feedback devices (e.g., haptic actuators) for use in combined ultrasonic and/or electrosurgical instruments are contemplated in the subsequent disclosure.

Other electrical surgical instruments include, without limitation, irreversible and/or reversible electroporation, and/or microwave technologies, among others. Accordingly, the techniques disclosed herein are applicable to ultrasonic, bipolar or monopolar RF (electrosurgical), irreversible and/or reversible electroporation, and/or microwave based surgical instruments, among others.

SUMMARY

An aspect of an ultrasonic device may include an electromechanical ultrasonic system defined by a predetermined resonant frequency, the electromechanical ultrasonic system further having an ultrasonic transducer coupled to an ultrasonic blade. An aspect of a method of detecting proper installation of two or more components of ultrasonic device may include determining, by a processor or control circuit, a spectroscopy signature of the ultrasonic blade coupled to the ultrasonic transducer, comparing, by the processor or control circuit, the spectroscopy signature to a reference spectroscopy signature, determining, by the processor or control circuit, an installation state of the two or more components based on the comparison, and controlling, by the processor or control circuit, a delivery of power to the ultrasonic transducer based on the comparison.

In one aspect, the method may further include enabling, by the processor or control circuit, an operation of the ultrasonic device when the installation state of the two or more components is proper.

In one aspect, the method may further include disabling, by the processor or control circuit, an operation of the ultrasonic device when the installation state of the two or more components is not proper and generating, by the processor or control circuit, a warning.

In one aspect of the method, generating, by the processor or control circuit, a warning may include generating, by the processor or control circuit, a visible warning.

In one aspect of the method, generating, by the processor or control circuit, a warning may include generating, by the processor or control circuit, an audible warning.

In one aspect of the method, generating, by the processor or control circuit, a warning may include generating, by the processor or control circuit, a tactile warning.

In one aspect of the method, determining, by a processor or control circuit, a spectroscopy signature of the ultrasonic blade coupled to the ultrasonic transducer may include measuring, by the processor or control circuit, a complex impedance of the ultrasonic transducer, wherein the complex impedance is defined as $$Z_g(t) = \frac{V_g(t)}{I_g(t)},$$

receiving, by the processor or control circuit, a complex impedance measurement data point, comparing, by the processor or control circuit, the complex impedance measurement data point to a data point in a reference complex impedance characteristic pattern, classifying, by the processor or control circuit, the complex impedance measurement data point based on a result of the comparison analysis, and assigning, by the processor or control circuit, a state or condition of an end effector based on the result of the comparison analysis.

In one aspect of the method, comparing, by the processor or control circuit, the complex impedance measurement data point to a data point in a reference complex impedance characteristic pattern may include comparing, by the processor or control circuit, the spectroscopy signature of the ultrasonic blade coupled to the ultrasonic transducer to the reference spectroscopy signature.

In one aspect of the method, determining, by a processor or control circuit, a spectroscopy signature of the ultrasonic blade coupled to the ultrasonic transducer may include applying, by a drive circuit, a drive signal to the ultrasonic transducer, wherein the drive signal is a periodic signal defined by a magnitude and frequency, sweeping, by a processor or control circuit, the frequency of the drive signal from below resonance to above resonance of the electromechanical ultrasonic system, measuring and recording, by the processor or control circuit, impedance/admittance circle variables $R_e$, $G_e$, $X_e$, and $B_e$, comparing, by the processor or control circuit, the measured impedance/admittance circle variables $R_e$, $G_e$, $X_e$, and $B_e$ to reference impedance/admittance circle variables $R_{ref}$, $G_{ref}$, $X_{ref}$, and $B_{ref}$, and determining, by the processor or control circuit, a state or condition of an end effector based on the result of the comparison analysis.

An aspect of an ultrasonic surgical instrument may include an ultrasonic electromechanical system having an ultrasonic transducer coupled to an ultrasonic blade via an ultrasonic waveguide, in which the ultrasonic electromechanical system my include two or more components of which at least one of the two or more components is a disposable device and of which at least one of the two or more components is a reusable device. An aspect of the ultrasonic surgical instrument may further include a generator configured to supply power to the ultrasonic transducer, in which the generator includes a control circuit configured to determine a spectroscopy signature of the ultrasonic blade coupled to the ultrasonic transducer, compare the spectroscopy signature to a reference spectroscopy signature, determine an installation state of the two or more components based on the comparison, and control a delivery of power to the ultrasonic transducer based on the comparison.

In one aspect of the ultrasonic surgical instrument, the control circuit may be further configured to enable an operation of the ultrasonic device when the installation state of the two or more components is proper.

In one aspect of the ultrasonic surgical instrument, the control circuit is further configured to disable an operation of the ultrasonic device when the installation state of the two or more components is not proper and generate a warning.

In one aspect of the ultrasonic surgical instrument, the warning comprises a visible warning.

In one aspect of the ultrasonic surgical instrument, the warning comprises an audible warning.

In one aspect of the ultrasonic surgical instrument, the warning comprises a tactile warning.

In one aspect of the ultrasonic surgical instrument, the control circuit is further configured to measure a complex impedance of the ultrasonic transducer, wherein the complex impedance is defined as $$Z_g(t) = \frac{V_g(t)}{I_g(t)},$$

receive a complex impedance measurement data point, compare the complex impedance measurement data point to a data point in a reference complex impedance characteristic pattern, classify the complex impedance measurement data point based on a result of the comparison analysis, and assign a state or condition of an end effector based on the result of the comparison analysis.

In one aspect of the ultrasonic surgical instrument, the control circuit is further configured to cause a drive circuit to apply a drive signal to the ultrasonic transducer, wherein the drive signal is a periodic signal defined by a magnitude and frequency, sweep the frequency of the drive signal from below resonance to above resonance of the electromechanical ultrasonic system, measure and record impedance/admittance circle variables $R_e$, $G_e$, $X_e$, and $B_e$, compare the measured impedance/admittance circle variables $R_e$, $G_e$, $X_e$, and $B_e$ to reference impedance/admittance circle variables $R_{ref}$, $G_{ref}$, $X_{ref}$, and $B_{ref}$, and determine a state or condition of an end effector based on the result of the comparison analysis.

An aspect of a generator for an ultrasonic surgical instrument, in which the ultrasonic surgical instrument includes two or more components of which at least one of the two or more components is a disposable device and of which at least one of the two or more components is a reusable device, may include a control circuit configured to determine a spectroscopy signature of an ultrasonic blade coupled to a ultrasonic transducer, compare the spectroscopy signature to a reference spectroscopy signature, determine an installation state of the two or more components based on the comparison, and control a delivery of power to the ultrasonic transducer based on the comparison.

In one aspect of the generator for an ultrasonic surgical instrument, the control circuit is further configured to enable an operation of the ultrasonic device when the installation state of the two or more components is proper.

In one aspect of the generator for an ultrasonic surgical instrument, the control circuit is further configured to disable an operation of the ultrasonic device when the installation state of the two or more components is not proper and generate a warning.

In one aspect of the generator for an ultrasonic surgical instrument, the warning includes a visible warning.

In one aspect of the generator for an ultrasonic surgical instrument, the warning includes an audible warning.

In one aspect of the generator for an ultrasonic surgical instrument, the warning comprises a tactile warning.

In one aspect of the generator for an ultrasonic surgical instrument, the control circuit is further configured to measure a complex impedance of the ultrasonic transducer, wherein the complex impedance is defined as $$Z_g(t) = \frac{V_g(t)}{I_g(t)},$$

receive a complex impedance measurement data point, compare the complex impedance measurement data point to a data point in a reference complex impedance characteristic pattern, classify the complex impedance measurement data point based on a result of the comparison analysis, and assign a state or condition of an end effector based on the result of the comparison analysis.

In one aspect of the generator for an ultrasonic surgical instrument, the control circuit is further configured to cause a drive circuit to apply a drive signal to the ultrasonic transducer, wherein the drive signal is a periodic signal defined by a magnitude and frequency, sweep the frequency of the drive signal from below resonance to above resonance of the electromechanical ultrasonic system, measure and record impedance/admittance circle variables $R_e$, $G_e$, $X_e$, and $B_e$, compare the measured impedance/admittance circle variables $R_e$, $G_e$, $X_e$, and $B_e$ to reference impedance/admittance circle variables $R_{ref}$, $G_{ref}$, $X_{ref}$, and $B_{ref}$, and determine a state or condition of an end effector based on the result of the comparison analysis.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 31 is an ultrasonic device configured to identify the status of the ultrasonic blade and determine the clocked clamp arm status to determine whether a disposable portion of a reusable and disposable ultrasonic device has been installed correctly, in accordance with at least one aspect of the present disclosure.

FIG. 32 is an end effector portion of the ultrasonic device shown in FIG. 31.

DESCRIPTION

Figure 1:
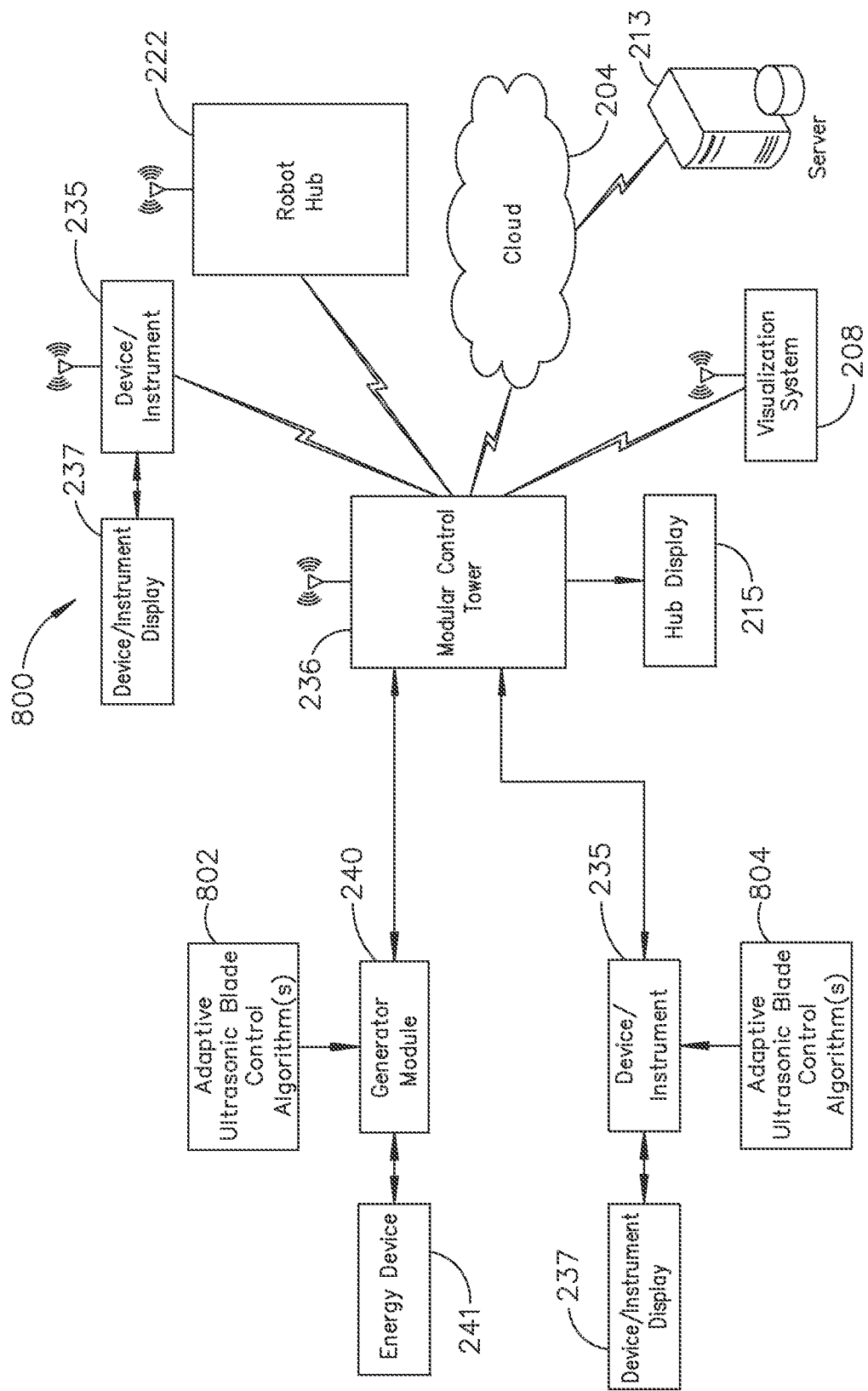
FIG. 1 is a system configured to execute adaptive ultrasonic blade control algorithms in a surgical data network comprising a modular communication hub, in accordance with at least one aspect of the present disclosure.

Applicant of the present patent application also owns the following U.S. patent applications filed on Sep. 27, 2018, each of which is herein incorporated by reference in its entirety:

- U.S. patent application Ser. No. 16/144,335, titled METHODS FOR CONTROLLING TEMPERATURE IN ULTRASONIC DEVICE, now U.S. Pat. No. 11,259,830;
- U.S. patent application Ser. No. 16/144,345, titled ULTRASONIC SEALING ALGORITHM WITH TEMPERATURE CONTROL, now U.S. Patent Application Publication No. 2019/0274718;
- U.S. patent application Ser. No. 16/144,351, titled APPLICATION OF SMART ULTRASONIC BLADE TECHNOLOGY, now U.S. Patent Application Publication No. 2019/0274705;
- U.S. patent application Ser. No. 16/144,423, titled ADAPTIVE ADVANCED TISSUE TREATMENT PAD SAVER MODE, now U.S. Patent Application Publication No. 2019/0274709;
- U.S. patent application Ser. No. 16/144,455, titled SMART BLADE TECHNOLOGY TO CONTROL BLADE INSTABILITY, now U.S. Pat. No. 11,344,326, and
- U.S. patent application Ser. No. 16/144,483, titled START TEMPERATURE OF BLADE, now U.S. Pat. No. 11,389,188.

Applicant of the present patent application also owns the following U.S. patent applications file on Sep. 27, 2018, each of which is herein incorporated by reference in its entirety:

- U.S. patent application Ser. No. 16/144,383, titled METHODS FOR ESTIMATING AND CONTROLLING STATE OF ULTRASONIC END EFFECTOR, now U.S. Patent Application Publication No. 2019/0274706;
- U.S. patent application Ser. No. 16/144,391, titled IN-THE-JAW CLASSIFIER BASED ON MODEL, now U.S. Patent Application Publication No. 2019/0274719;
- U.S. patent application Ser. No. 16/144,397, titled APPLICATION OF SMART BLADE TECHNOLOGY, now U.S. Pat. No. 11,399,858;
- U.S. patent application Ser. No. 16/144,405, titled SMART BLADE AND POWER PULSING, now U.S. Pat. No. 11,337,746;
- U.S. patent application Ser. No. 16/144,418, titled ADJUSTMENT OF COMPLEX IMPEDANCE TO COMPENSATE FOR LOST POWER IN AN ARTICULATING ULTRASONIC DEVICE, now U.S. Patent Application Publication No. 2019/0274662;
- U.S. patent application Ser. No. 16/144,427, titled USING SPECTROSCOPY TO DETERMINE DEVICE USE STATE IN COMBO INSTRUMENT, now U.S. Patent Application Publication No. 2019/0274710;
- U.S. patent application Ser. No. 16/144,434, titled VESSEL SENSING FOR ADAPTIVE ADVANCED HEMOSTASIS, now U.S. Patent Application Publication No. 2019/0274711;
- U.S. patent application Ser. No. 16/144,460, titled CALCIFIED VESSEL IDENTIFICATION, now U.S. Patent Application Publication No. 2019/0274713;
- U.S. patent application Ser. No. 16/144,472, titled DETECTION OF LARGE VESSELS DURING PARENCHYMAL DISSECTION USING A SMART BLADE, now U.S. Patent Application Publication No. 2019/0274749;
- U.S. patent application Ser. No. 16/144,486, titled LIVE TIME TISSUE CLASSIFICATION USING ELECTRICAL PARAMETERS, now U.S. Pat. No. 11,298,148; and
- U.S. patent application Ser. No. 16/144,508, titled FINE DISSECTION MODE FOR TISSUE CLASSIFICATION, now U.S. Patent Application Publication No. 2019/0274752.

Applicant of the present application owns the following U.S. Patent Applications, filed on Sep. 10, 2018, the disclosure of each of which is herein incorporated by reference in its entirety:

- U.S. Provisional Patent Application Ser. No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION;
- U.S. provisional Patent Application Ser. No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB;
- U.S. Provisional Patent Application Ser. No. 62/729,184, titled POWERED SURGICAL TOOL WITH A PREDEFINED ADJUSTABLE CONTROL ALGORITHM FOR CONTROLLING AT LEAST ONE END-EFFECTOR PARAMETER AND A MEANS FOR LIMITING THE ADJUSTMENT;
- U.S. Provisional Patent Application Ser. No. 62/729,183, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;
- U.S. Provisional Patent Application Ser. No. 62/729,191, titled A CONTROL FOR A SURGICAL NETWORK OR SURGICAL NETWORK CONNECTED DEVICE THAT ADJUSTS ITS FUNCTION BASED ON A SENSED SITUATION OR USAGE;
- U.S. Provisional Patent Application Ser. No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES;
- U.S. Provisional Patent Application Ser. No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES; and
- U.S. Provisional Patent Application Ser. No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING.

Applicant of the present application owns the following U.S. Patent Applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR EMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. Patent Applications, filed on Aug. 23, 2018, the disclosure of each of which is herein incorporated by reference in its entirety:

U.S. Provisional Patent Application No. 62/721,995, titled CONTROLLING AN ULTRASONIC SURGICAL INSTRUMENT ACCORDING TO TISSUE LOCATION;

U.S. Provisional Patent Application No. 62/721,998, titled SITUATIONAL AWARENESS OF ELECTROSURGICAL SYSTEMS;

U.S. Provisional Patent Application No. 62/721,999, titled INTERRUPTION OF ENERGY DUE TO INADVERTENT CAPACITIVE COUPLING;

U.S. Provisional Patent Application No. 62/721,994, titled BIPOLAR COMBINATION DEVICE THAT AUTOMATICALLY ADJUSTS PRESSURE BASED ON ENERGY MODALITY; and U.S. Provisional Patent Application No. 62/721,996, titled RADIO FREQUENCY ENERGY DEVICE FOR DELIVERING COMBINED ELECTRICAL SIGNALS.

Applicant of the present application owns the following U.S. Patent Applications, filed on Jun. 30, 2018, the disclosure of each of which is herein incorporated by reference in its entirety:

U.S. Provisional Patent Application No. 62/692,747, titled SMART ACTIVATION OF AN ENERGY DEVICE BY ANOTHER DEVICE;

U.S. Provisional Patent Application No. 62/692,748, titled SMART ENERGY ARCHITECTURE; and U.S. Provisional Patent Application No. 62/692,768, titled SMART ENERGY DEVICES.

Applicant of the present application owns the following U.S. Patent Applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. Provisional Patent Applications, filed on Jun. 28, 2018, the disclosure of each of which is herein incorporated by reference in its entirety:

U.S. Provisional Patent Application Ser. No. 62/691,228, titled A METHOD OF USING REINFORCED FLEX CIRCUITS WITH MULTIPLE SENSORS WITH ELECTROSURGICAL DEVICES;

U.S. Provisional Patent Application Ser. No. 62/691,227, titled CONTROLLING A SURGICAL INSTRUMENT ACCORDING TO SENSED CLOSURE PARAMETERS;

U.S. Provisional Patent Application Ser. No. 62/691,230, titled SURGICAL INSTRUMENT HAVING A FLEXIBLE ELECTRODE;

U.S. Provisional Patent Application Ser. No. 62/691,219, titled SURGICAL EVACUATION SENSING AND MOTOR CONTROL;

U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and U.S. Provisional Patent Application Ser. No. 62/691,251, titled DUAL IN-SERIES LARGE AND SMALL DROPLET FILTERS.

Applicant of the present application owns the following U.S. Provisional Patent Application, filed on Apr. 19, 2018, the disclosure of each of which is herein incorporated by reference in its entirety:

U.S. Provisional Patent Application Ser. No. 62/659,900, titled METHOD OF HUB COMMUNICATION.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Adaptive Ultrasonic Blade Control Algorithms

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 1-2, for example. Accordingly, the following description of adaptive ultrasonic blade control algorithms should be read in conjunction with FIGS. 1-2 and the description associated therewith.

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

FIG. 1 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802 as described herein. In another aspect, the device/instrument 235 is configured to execute the adaptive ultrasonic blade control algorithm(s) 804 as described herein with reference to FIGS. 19-34. In another aspect, both the device/instrument 235 and the device/instrument 235 are configured to execute the adaptive ultrasonic blade control algorithms 802, 804 as described herein with reference to FIGS. 19-34.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 7-12.

The generator module 240 or the device/instrument 235 or both are coupled to the modular control tower 236 connected to multiple operating theater devices such as, for example, intelligent surgical instruments, robots, and other computerized devices located in the operating theater. In some aspects, a surgical data network may include a modular communication hub configured to connect modular devices located in one or more operating theaters of a healthcare facility, or any room in a healthcare facility specially equipped for surgical operations, to a cloud-based system (e.g., the cloud 204 that may include a remote server 213 coupled to a storage device).

Modular devices located in the operating theater may be coupled to the modular communication hub. The network hub and/or the network switch may be coupled to a network router to connect the devices to the cloud 204 or a local computer system. Data associated with the devices may be transferred to cloud-based computers via the router for remote data processing and manipulation. Data associated with the devices may also be transferred to a local computer system for local data processing and manipulation. Modular devices located in the same operating theater also may be coupled to a network switch. The network switch may be coupled to the network hub and/or the network router to connect to the devices to the cloud 204. Data associated with the devices may be transferred to the cloud 204 via the network router for data processing and manipulation. Data associated with the devices may also be transferred to the local computer system for local data processing and manipulation.

It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub and/or computer system located in the surgical theater (e.g., a fixed, mobile, temporary, or field operating room or space) and to devices connected to the modular communication hub and/or computer system through the Internet. The cloud infrastructure may be maintained by a cloud service provider. In this context, the cloud service provider may be the entity that coordinates the usage and control of the devices located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

FIG. 1 further illustrates some aspects of a computer-implemented interactive surgical system comprising a modular communication hub that may include the system 800 configured to execute adaptive ultrasonic blade control algorithms in a surgical data network. The surgical system may include at least one surgical hub in communication with a cloud 204 that may include a remote server 213. In one aspect, the computer-implemented interactive surgical system comprises a modular control tower 236 connected to multiple operating theater devices such as, for example, intelligent surgical instruments, robots, and other computerized devices located in the operating theater. The modular control tower 236 may comprise a modular communication hub coupled to a computer system. In some aspects, the modular control tower 236 is coupled to an imaging module that is coupled to an endoscope, a generator module 240 that is coupled to an energy device 241, and a smart device/instrument 235 optionally coupled to a display 237. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display 215 also may display data received from devices connected to the modular control tower in conjunction with images and overlaid images.

Generator Hardware

Figure 2:
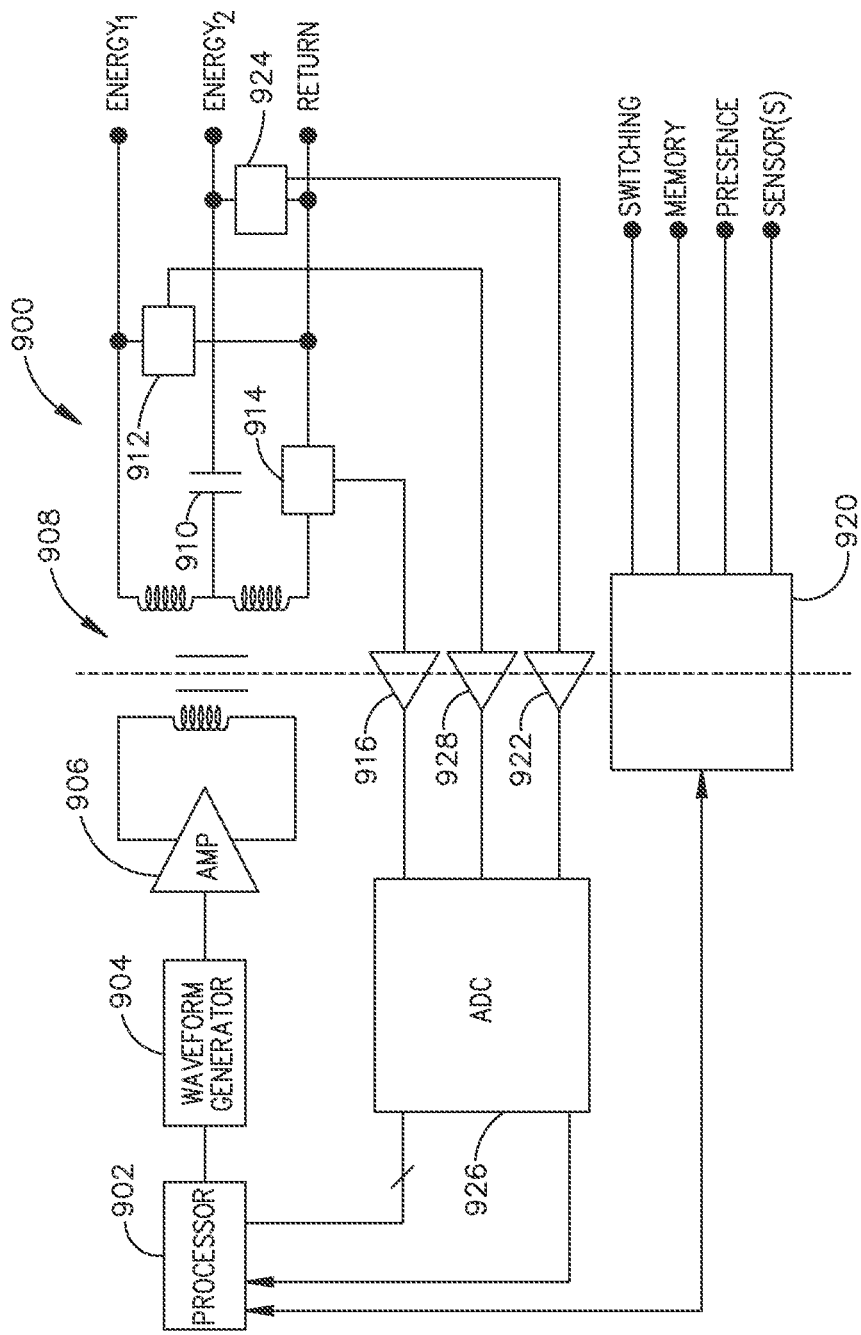
FIG. 2 illustrates an example of a generator, in accordance with at least one aspect of the present disclosure.

FIG. 2 illustrates an example of a generator 900, which is one form of a generator configured to couple to an ultrasonic instrument and further configured to execute adaptive ultrasonic blade control algorithms in a surgical data network comprising a modular communication hub as shown in FIG. 1. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 906 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 928, 922 and the output of the current sensing circuit 914 is provided to another isolation transformer 916. The outputs of the isolation transformers 916, 928, 922 on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 928, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be ultrasonic energy and the second energy modality $ENERGY_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 2 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 2, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 2. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 3:
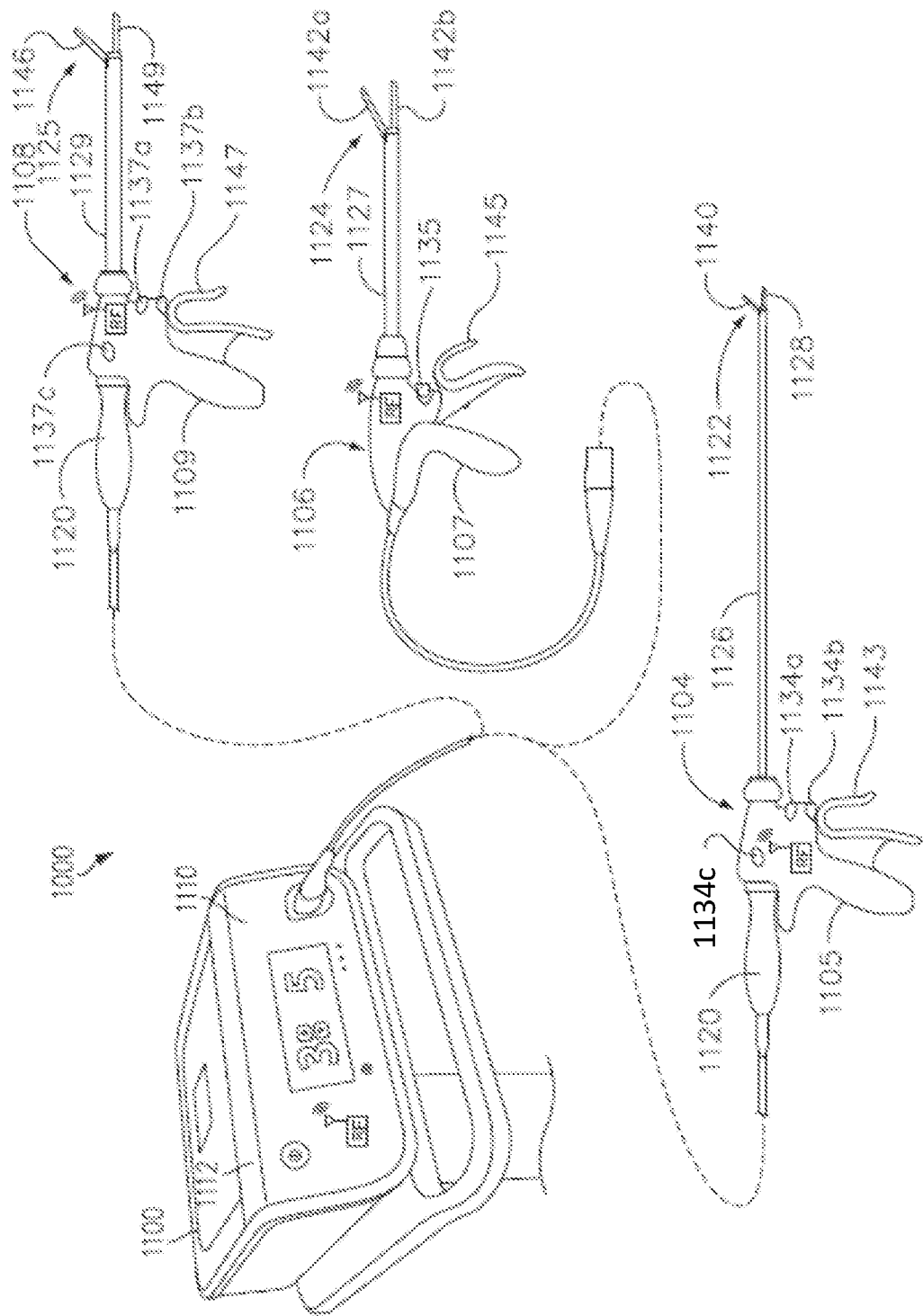
FIG. 3 is a surgical system comprising a generator and various surgical instruments usable therewith, in accordance with at least one aspect of the present disclosure.

FIG. 3 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 3 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134a, 1134b, 1134c to energize and drive the ultrasonic blade 1128 or other function. The toggle buttons 1134a, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124.

The end effector 1124 comprises electrodes in clamp arms 1142a, 1142b and return through an electrical conductor portion of the shaft 1127. The electrodes are coupled to and energized by a bipolar energy source within the generator 1100. The handpiece 1107 comprises a trigger 1145 to operate the clamp arms 1142a, 1142b and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137a, 1137b, 1137c to energize and drive the ultrasonic blade 1149 or other function. The toggle buttons 1137a, 1137b, 1137c can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 3 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

Figure 4:
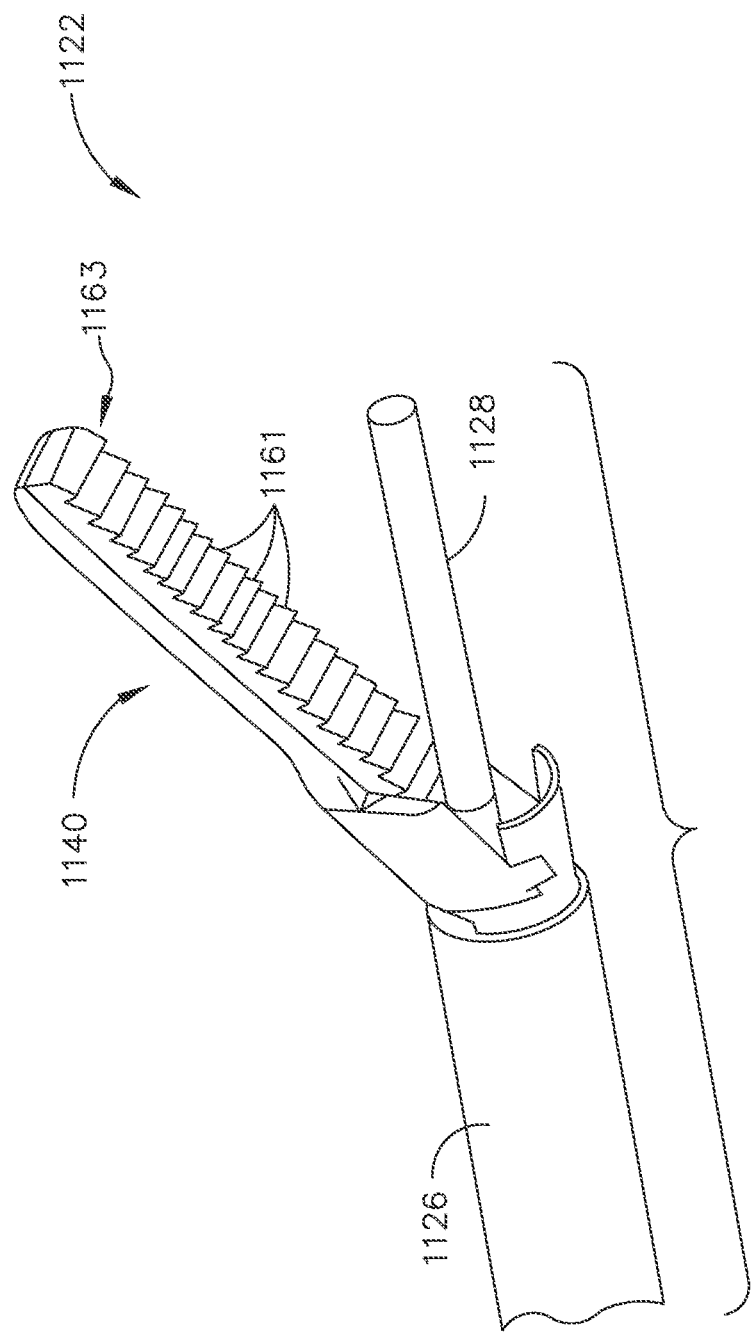
FIG. 4 is an end effector, in accordance with at least one aspect of the present disclosure.

FIG. 4 is an end effector 1122 of the example ultrasonic device 1104, in accordance with at least one aspect of the present disclosure. The end effector 1122 may comprise a blade 1128 that may be coupled to the ultrasonic transducer 1120 via a wave guide. When driven by the ultrasonic transducer 1120, the blade 1128 may vibrate and, when brought into contact with tissue, may cut and/or coagulate the tissue, as described herein. According to various aspects, and as illustrated in FIG. 4, the end effector 1122 may also comprise a clamp arm 1140 that may be configured for cooperative action with the blade 1128 of the end effector 1122. With the blade 1128, the clamp arm 1140 may comprise a set of jaws. The clamp arm 1140 may be pivotally connected at a distal end of a shaft 1126 of the instrument portion 1104. The clamp arm 1140 may include a clamp arm tissue pad 1163, which may be formed from TEFLON® or other suitable low-friction material. The pad 1163 may be mounted for cooperation with the blade 1128, with pivotal movement of the clamp arm 1140 positioning the clamp pad 1163 in substantially parallel relationship to, and in contact with, the blade 1128. By this construction, a tissue bite to be clamped may be grasped between the tissue pad 1163 and the blade 1128. The tissue pad 1163 may be provided with a sawtooth-like configuration including a plurality of axially spaced, proximally extending gripping teeth 1161 to enhance the gripping of tissue in cooperation with the blade 1128. The clamp arm 1140 may transition from the open position shown in FIG. 4 to a closed position (with the clamp arm 1140 in contact with or proximity to the blade 1128) in any suitable manner. For example, the handpiece 1105 may comprise a jaw closure trigger. When actuated by a clinician, the jaw closure trigger may pivot the clamp arm 1140 in any suitable manner.

The generator 1100 may be activated to provide the drive signal to the ultrasonic transducer 1120 in any suitable manner. For example, the generator 1100 may comprise a foot switch 1430 (FIG. 5) coupled to the generator 1100 via a footswitch cable 1432. A clinician may activate the ultrasonic transducer 1120, and thereby the ultrasonic transducer 1120 and blade 1128, by depressing the foot switch 1430. In addition, or instead of the foot switch 1430, some aspects of the device 1104 may utilize one or more switches positioned on the handpiece 1105 that, when activated, may cause the generator 1100 to activate the ultrasonic transducer 1120. In one aspect, for example, the one or more switches may comprise a pair of toggle buttons 1134, 1134a, 1134b (FIG. 3), for example, to determine an operating mode of the device 1104. When the toggle button 1134a is depressed, for example, the ultrasonic generator 1100 may provide a maximum drive signal to the ultrasonic transducer 1120, causing it to produce maximum ultrasonic energy output. Depressing toggle button 1134b may cause the ultrasonic generator 1100 to provide a user-selectable drive signal to the ultrasonic transducer 1120, causing it to produce less than the maximum ultrasonic energy output. The device 1104 additionally or alternatively may comprise a second switch to, for example, indicate a position of a jaw closure trigger for operating the jaws via the clamp arm 1140 of the end effector 1122. Also, in some aspects, the ultrasonic generator 1100 may be activated based on the position of the jaw closure trigger, (e.g., as the clinician depresses the jaw closure trigger to close the jaws via the clamp arm 1140, ultrasonic energy may be applied).

Additionally or alternatively, the one or more switches may comprise a toggle button 1134 that, when depressed, causes the generator 1100 to provide a pulsed output (FIG. 3). The pulses may be provided at any suitable frequency and grouping, for example. In certain aspects, the power level of the pulses may be the power levels associated with toggle buttons 1134a, 1134b (maximum, less than maximum), for example.

It will be appreciated that a device 1104 may comprise any combination of the toggle buttons 1134a, 1134b, 1134 (FIG. 3). For example, the device 1104 could be configured to have only two toggle buttons: a toggle button 1134a for producing maximum ultrasonic energy output and a toggle button 1134 for producing a pulsed output at either the maximum or less than maximum power level per. In this way, the drive signal output configuration of the generator 1100 could be five continuous signals, or any discrete number of individual pulsed signals (1, 2, 3, 4, or 5). In certain aspects, the specific drive signal configuration may be controlled based upon, for example, EEPROM settings in the generator 1100 and/or user power level selection(s).

In certain aspects, a two-position switch may be provided as an alternative to a toggle button 1134 (FIG. 3). For example, a device 1104 may include a toggle button 1134a for producing a continuous output at a maximum power level and a two-position toggle button 1134b. In a first detented position, toggle button 1134*b* may produce a continuous output at a less than maximum power level, and in a second detented position the toggle button 1134*b* may produce a pulsed output (e.g., at either a maximum or less than maximum power level, depending upon the EEPROM settings).

In some aspects, the RF electrosurgical end effector 1124, 1125 (FIG. 3) may also comprise a pair of electrodes. The electrodes may be in communication with the generator 1100, for example, via a cable. The electrodes may be used, for example, to measure an impedance of a tissue bite present between the clamp arm 1142*a*, 1146 and the blade 1142*b*, 1149. The generator 1100 may provide a signal (e.g., a non-therapeutic signal) to the electrodes. The impedance of the tissue bite may be found, for example, by monitoring the current, voltage, etc. of the signal.

Figure 5:
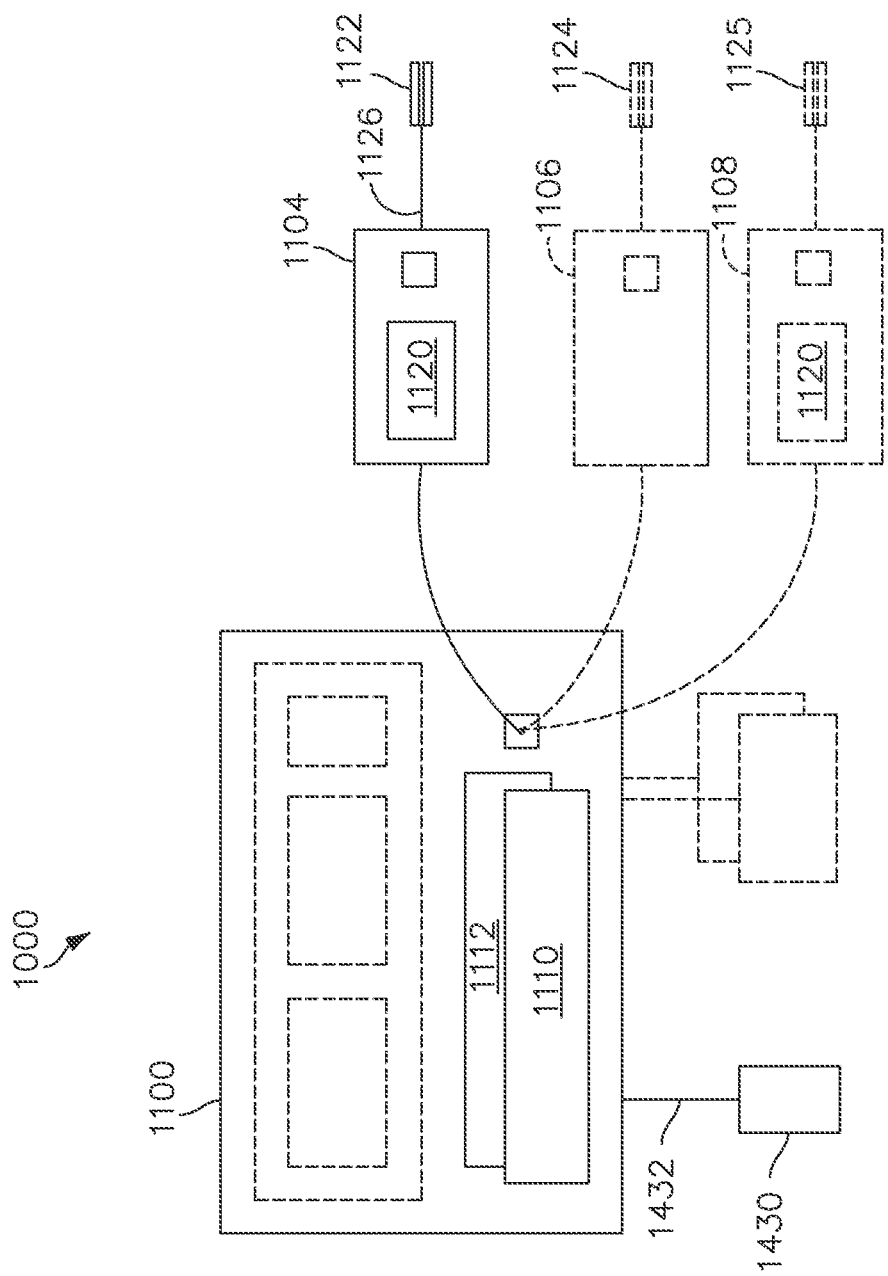
FIG. 5 is a diagram of the surgical system of FIG. 3, in accordance with at least one aspect of the present disclosure.

In various aspects, the generator 1100 may comprise several separate functional elements, such as modules and/or blocks, as shown in FIG. 5, a diagram of the surgical system 1000 of FIG. 3. Different functional elements or modules may be configured for driving the different kinds of surgical devices 1104, 1106, 1108. For example an ultrasonic generator module may drive an ultrasonic device, such as the ultrasonic device 1104. An electrosurgery/RF generator module may drive the electrosurgical device 1106. The modules may generate respective drive signals for driving the surgical devices 1104, 1106, 1108. In various aspects, the ultrasonic generator module and/or the electrosurgery/RF generator module each may be formed integrally with the generator 1100. Alternatively, one or more of the modules may be provided as a separate circuit module electrically coupled to the generator 1100. (The modules are shown in phantom to illustrate this option.) Also, in some aspects, the electrosurgery/RF generator module may be formed integrally with the ultrasonic generator module, or vice versa.

In accordance with the described aspects, the ultrasonic generator module may produce a drive signal or signals of particular voltages, currents, and frequencies (e.g. 55,500 cycles per second, or Hz). The drive signal or signals may be provided to the ultrasonic device 1104, and specifically to the transducer 1120, which may operate, for example, as described above. In one aspect, the generator 1100 may be configured to produce a drive signal of a particular voltage, current, and/or frequency output signal that can be stepped with high resolution, accuracy, and repeatability.

In accordance with the described aspects, the electrosurgery/RF generator module may generate a drive signal or signals with output power sufficient to perform bipolar electrosurgery using radio frequency (RF) energy. In bipolar electrosurgery applications, the drive signal may be provided, for example, to the electrodes of the electrosurgical device 1106, for example, as described above. Accordingly, the generator 1100 may be configured for therapeutic purposes by applying electrical energy to the tissue sufficient for treating the tissue (e.g., coagulation, cauterization, tissue welding, etc.).

The generator 1100 may comprise an input device 2150 (FIG. 8B) located, for example, on a front panel of the generator 1100 console. The input device 2150 may comprise any suitable device that generates signals suitable for programming the operation of the generator 1100. In operation, the user can program or otherwise control operation of the generator 1100 using the input device 2150. The input device 2150 may comprise any suitable device that generates signals that can be used by the generator (e.g., by one or more processors contained in the generator) to control the operation of the generator 1100 (e.g., operation of the ultrasonic generator module and/or electrosurgery/RF generator module). In various aspects, the input device 2150 includes one or more of: buttons, switches, thumbwheels, keyboard, keypad, touch screen monitor, pointing device, remote connection to a general purpose or dedicated computer. In other aspects, the input device 2150 may comprise a suitable user interface, such as one or more user interface screens displayed on a touch screen monitor, for example. Accordingly, by way of the input device 2150, the user can set or program various operating parameters of the generator, such as, for example, current (I), voltage (V), frequency (f), and/or period (T) of a drive signal or signals generated by the ultrasonic generator module and/or electrosurgery/RF generator module.

The generator 1100 may also comprise an output device 2140 (FIG. 8B) located, for example, on a front panel of the generator 1100 console. The output device 2140 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators).

Although certain modules and/or blocks of the generator 1100 may be described by way of example, it can be appreciated that a greater or lesser number of modules and/or blocks may be used and still fall within the scope of the aspects. Further, although various aspects may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one aspect, the ultrasonic generator drive module and electrosurgery/RF drive module 1110 (FIG. 3) may comprise one or more embedded applications implemented as firmware, software, hardware, or any combination thereof. The modules may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one aspect, the modules comprise a hardware component implemented as a processor for executing program instructions for monitoring various measurable characteristics of the devices 1104, 1106, 1108 and generating a corresponding output drive signal or signals for operating the devices 1104, 1106, 1108. In aspects in which the generator 1100 is used in conjunction with the device 1104, the drive signal may drive the ultrasonic transducer 1120 in cutting and/or coagulation operating modes. Electrical characteristics of the device 1104 and/or tissue may be measured and used to control operational aspects of the generator 1100 and/or provided as feedback to the user. In aspects in which the generator 1100 is used in conjunction with the device 1106, the drive signal may supply electrical energy (e.g., RF energy) to the end effector 1124 in cutting, coagulation and/or desiccation modes. Electrical characteristics of the device 1106 and/or tissue may be measured and used to control operational aspects of the generator 1100 and/or provided as feedback to the user. In various aspects, as previously discussed, the hardware components may be implemented as DSP, PLD, ASIC, circuits, and/or registers. In one aspect, the processor may be configured to store and execute computer software program instructions to generate the step function output signals for driving various components of the devices 1104, 1106, 1108, such as the ultrasonic transducer 1120 and the end effectors 1122, 1124, 1125.

An electromechanical ultrasonic system includes an ultrasonic transducer, a waveguide, and an ultrasonic blade. The electromechanical ultrasonic system has an initial resonant frequency defined by the physical properties of the ultrasonic transducer, the waveguide, and the ultrasonic blade. The ultrasonic transducer is excited by an alternating voltage $V_g(t)$ and current $I_g(t)$ signal equal to the resonant frequency of the electromechanical ultrasonic system. When the electromechanical ultrasonic system is at resonance, the phase difference between the voltage $V_g(t)$ and current $I_g(t)$ signals is zero. Stated another way, at resonance the inductive impedance is equal to the capacitive impedance. As the ultrasonic blade heats up, the compliance of the ultrasonic blade (modeled as an equivalent capacitance) causes the resonant frequency of the electromechanical ultrasonic system to shift. Thus, the inductive impedance is no longer equal to the capacitive impedance causing a mismatch between the drive frequency and the resonant frequency of the electromechanical ultrasonic system. The system is now operating "off-resonance." The mismatch between the drive frequency and the resonant frequency is manifested as a phase difference between the voltage $V_g(t)$ and current $I_g(t)$ signals applied to the ultrasonic transducer. The generator electronics can easily monitor the phase difference between the voltage $V_g(t)$ and current $I_g(t)$ signals and can continuously adjust the drive frequency until the phase difference is once again zero. At this point, the new drive frequency is equal to the new resonant frequency of the electromechanical ultrasonic system. The change in phase and/or frequency can be used as an indirect measurement of the ultrasonic blade temperature.

Figure 6:
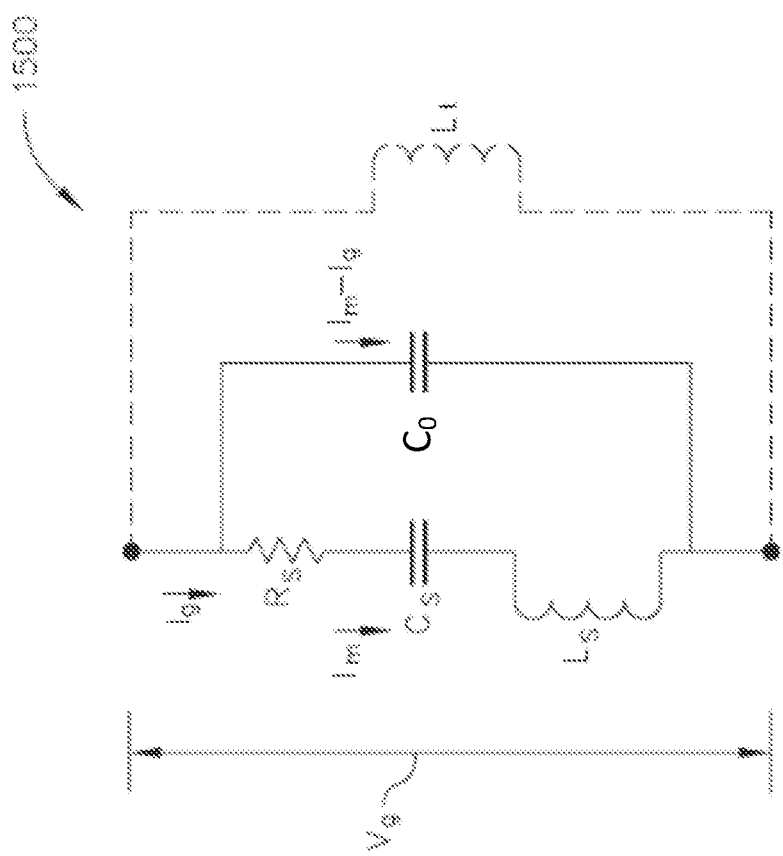
FIG. 6 is a model illustrating motional branch current, in accordance with at least one aspect of the present disclosure.

As shown in FIG. 6, the electromechanical properties of the ultrasonic transducer may be modeled as an equivalent circuit comprising a first branch having a static capacitance and a second "motional" branch having a serially connected inductance, resistance and capacitance that define the electromechanical properties of a resonator. Known ultrasonic generators may include a tuning inductor for tuning out the static capacitance at a resonant frequency so that substantially all of generator's drive signal current flows into the motional branch. Accordingly, by using a tuning inductor, the generator's drive signal current represents the motional branch current, and the generator is thus able to control its drive signal to maintain the ultrasonic transducer's resonant frequency. The tuning inductor may also transform the phase impedance plot of the ultrasonic transducer to improve the generator's frequency lock capabilities. However, the tuning inductor must be matched with the specific static capacitance of an ultrasonic transducer at the operational resonance frequency. In other words, a different ultrasonic transducer having a different static capacitance requires a different tuning inductor.

FIG. 6 illustrates an equivalent circuit 1500 of an ultrasonic transducer, such as the ultrasonic transducer 1120, according to one aspect. The circuit 1500 comprises a first "motional" branch having a serially connected inductance $L_s$, resistance $R_s$ and capacitance $C_s$ that define the electromechanical properties of the resonator, and a second capacitive branch having a static capacitance $C_0$. Drive current $I_g(t)$ may be received from a generator at a drive voltage $V_g(t)$, with motional current $I_m(t)$ flowing through the first branch and current $I_g(t)-I_m(t)$ flowing through the capacitive branch. Control of the electromechanical properties of the ultrasonic transducer may be achieved by suitably controlling $I_g(t)$ and $V_g(t)$. As explained above, known generator architectures may include a tuning inductor $L_t$ (shown in phantom in FIG. 6) in a parallel resonance circuit for tuning out the static capacitance $C_0$ at a resonant frequency so that substantially all of the generator's current output $I_g(t)$ flows through the motional branch. In this way, control of the motional branch current $I_m(t)$ is achieved by controlling the generator current output $I_g(t)$. The tuning inductor $L_t$ is specific to the static capacitance $C_0$ of an ultrasonic transducer, however, and a different ultrasonic transducer having a different static capacitance requires a different tuning inductor $L_t$. Moreover, because the tuning inductor $L_t$ is matched to the nominal value of the static capacitance $C_0$ at a single resonant frequency, accurate control of the motional branch current $I_m(t)$ is assured only at that frequency. As frequency shifts down with transducer temperature, accurate control of the motional branch current is compromised.

Various aspects of the generator 1100 may not rely on a tuning inductor $L_t$ to monitor the motional branch current $I_m(t)$. Instead, the generator 1100 may use the measured value of the static capacitance $C_0$ in between applications of power for a specific ultrasonic surgical device 1104 (along with drive signal voltage and current feedback data) to determine values of the motional branch current $I_m(t)$ on a dynamic and ongoing basis (e.g., in real-time). Such aspects of the generator 1100 are therefore able to provide virtual tuning to simulate a system that is tuned or resonant with any value of static capacitance $C_0$ at any frequency, and not just at a single resonant frequency dictated by a nominal value of the static capacitance $C_0$.

Figure 7:
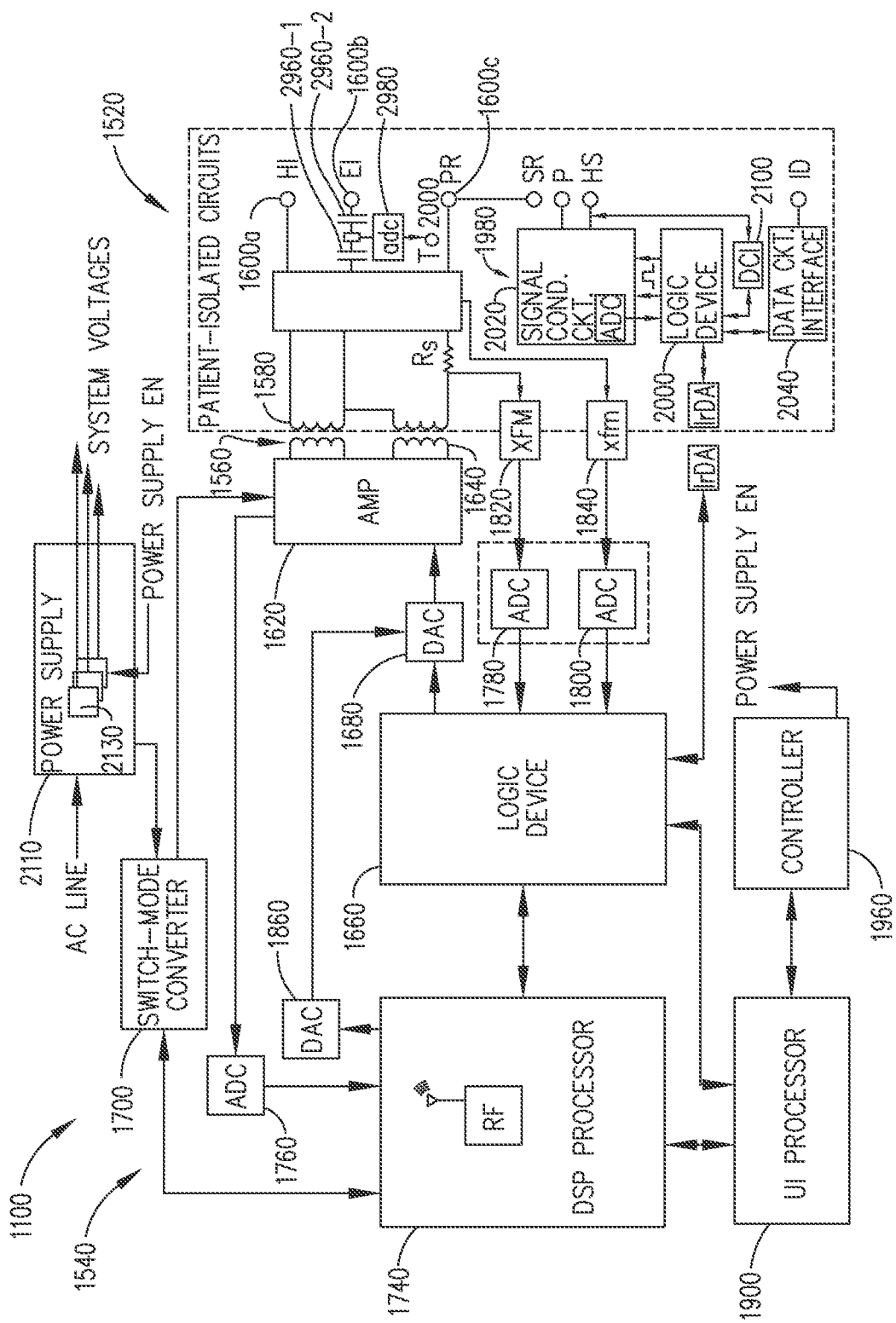
FIG. 7 is a structural view of a generator architecture, in accordance with at least one aspect of the present disclosure.
Figure 8A:
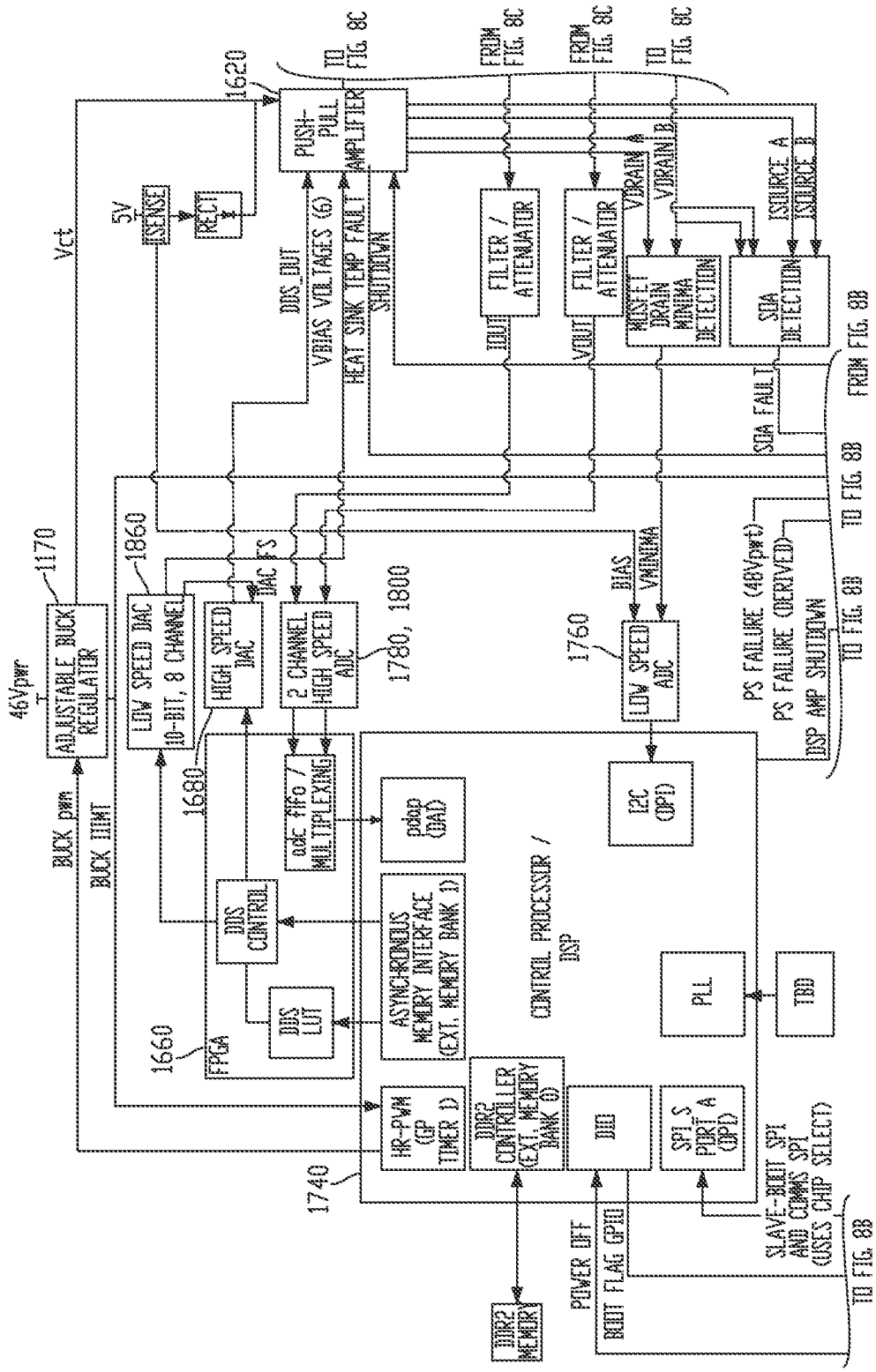
FIGS. 8A-8C are functional views of a generator architecture, in accordance with at least one aspect of the present disclosure.
Figure 8B:
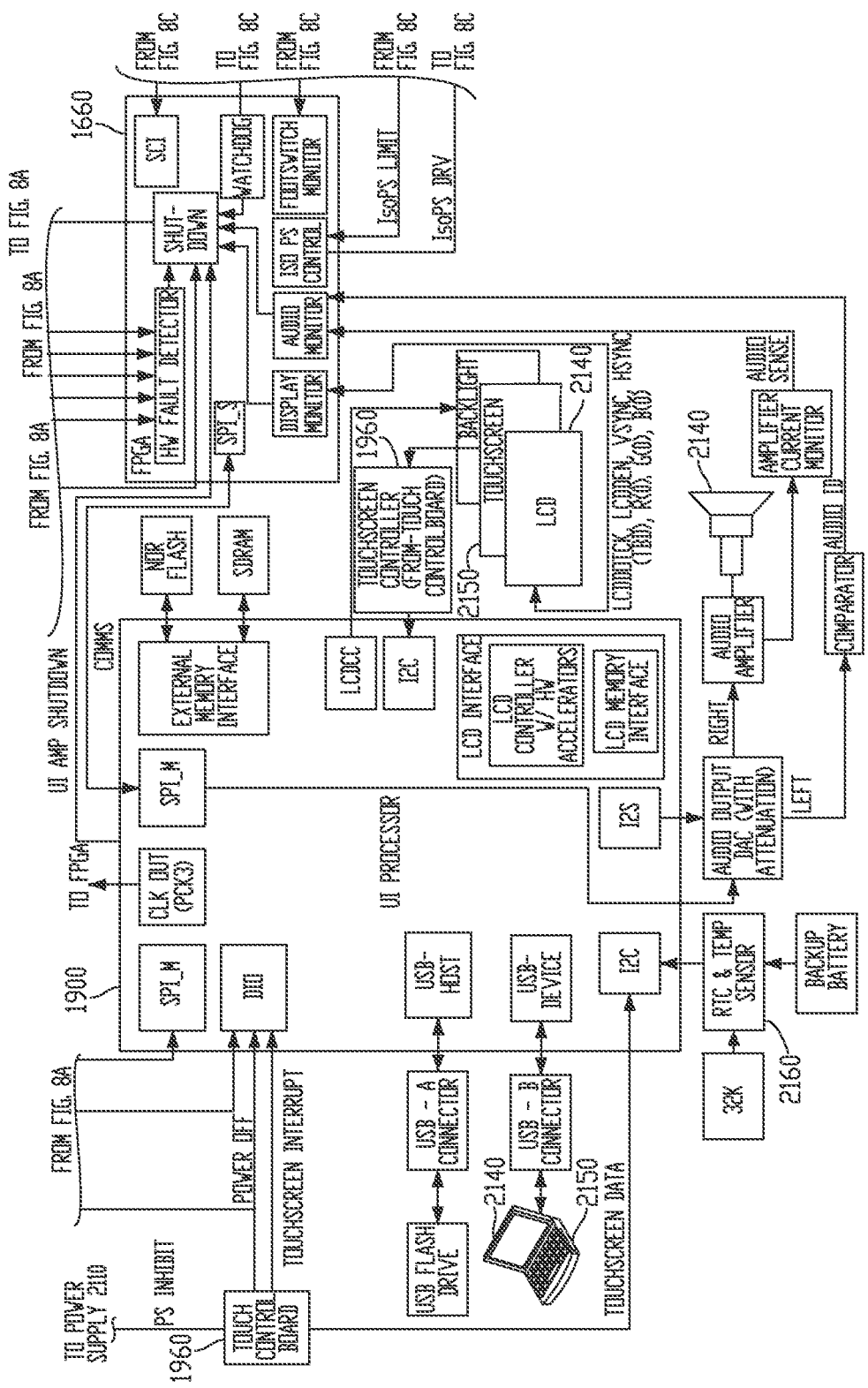
Figure 8C:
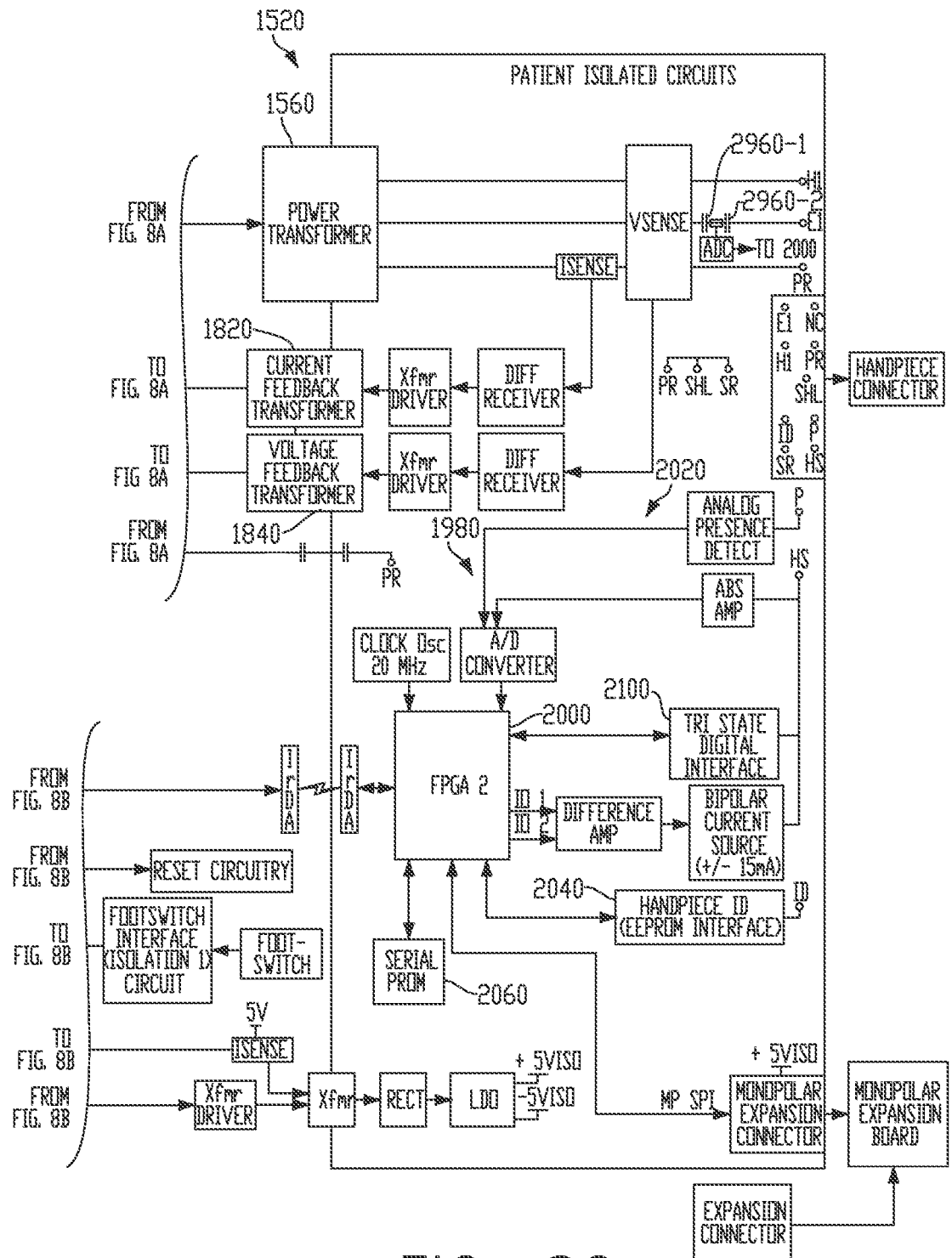

FIG. 7 is a simplified block diagram of one aspect of the generator 1100 for providing inductorless tuning as described above, among other benefits. FIGS. 8A-8C illustrate an architecture of the generator 1100 of FIG. 7 according to one aspect. With reference to FIG. 7, the generator 1100 may comprise a patient isolated stage 1520 in communication with a non-isolated stage 1540 via a power transformer 1560. A secondary winding 1580 of the power transformer 1560 is contained in the isolated stage 1520 and may comprise a tapped configuration (e.g., a center-tapped or non-center tapped configuration) to define drive signal outputs 1600*a*, 1600*b*, 1600*c* for outputting drive signals to different surgical devices, such as, for example, an ultrasonic surgical device 1104 and an electrosurgical device 1106. In particular, drive signal outputs 1600*a*, 1600*b*, 1600*c* may output a drive signal (e.g., a 420V RMS drive signal) to an ultrasonic surgical device 1104, and drive signal outputs 1600*a*, 1600*b*, 1600*c* may output a drive signal (e.g., a 100V RMS drive signal) to an electrosurgical device 1106, with output 1600*b* corresponding to the center tap of the power transformer 1560. The non-isolated stage 1540 may comprise a power amplifier 1620 having an output connected to a primary winding 1640 of the power transformer 1560. In certain aspects the power amplifier 1620 may comprise a push-pull amplifier, for example. The non-isolated stage 1540 may further comprise a programmable logic device 1660 for supplying a digital output to a digital-to-analog converter (DAC) 1680, which in turn supplies a corresponding analog signal to an input of the power amplifier 1620. In certain aspects the programmable logic device 1660 may comprise a field-programmable gate array (FPGA), for example. The programmable logic device 1660, by virtue of controlling the power amplifier's 1620 input via the DAC 1680, may therefore control any of a number of parameters (e.g., frequency, waveform shape, waveform amplitude) of drive signals appearing at the drive signal outputs 1600*a*, 1600*b*, 1600*c*. In certain aspects and as discussed below, the programmable logic device 1660, in conjunction with a processor (e.g., processor 1740 discussed below), may implement a number of digital signal processing (DSP)-based and/or other control algorithms to control parameters of the drive signals output by the generator 1100.

Power may be supplied to a power rail of the power amplifier 1620 by a switch-mode regulator 1700. In certain aspects the switch-mode regulator 1700 may comprise an adjustable buck regulator 1170, for example. As discussed above, the non-isolated stage 1540 may further comprise a processor 1740, which in one aspect may comprise a DSP processor such as an ADSP-21469 SHARC DSP, available from Analog Devices, Norwood, Mass., for example. In certain aspects the processor 1740 may control operation of the switch-mode power converter 1700 responsive to voltage feedback data received from the power amplifier 1620 by the processor 1740 via an analog-to-digital converter (ADC) 1760. In one aspect, for example, the processor 1740 may receive as input, via the ADC 1760, the waveform envelope of a signal (e.g., an RF signal) being amplified by the power amplifier 1620. The processor 1740 may then control the switch-mode regulator 1700 (e.g., via a pulse-width modulated (PWM) output) such that the rail voltage supplied to the power amplifier 1620 tracks the waveform envelope of the amplified signal. By dynamically modulating the rail voltage of the power amplifier 1620 based on the waveform envelope, the efficiency of the power amplifier 1620 may be significantly improved relative to a fixed rail voltage amplifier scheme. The processor 1740 may be configured for wired or wireless communication.

In certain aspects and as discussed in further detail in connection with FIGS. 9A-9B, the programmable logic device 1660, in conjunction with the processor 1740, may implement a direct digital synthesizer (DDS) control scheme to control the waveform shape, frequency and/or amplitude of drive signals output by the generator 1100. In one aspect, for example, the programmable logic device 1660 may implement a DDS control algorithm 2680 (FIG. 9A) by recalling waveform samples stored in a dynamically-updated look-up table (LUT), such as a RAM LUT which may be embedded in an FPGA. This control algorithm is particularly useful for ultrasonic applications in which an ultrasonic transducer, such as the ultrasonic transducer 1120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1100 is impacted by various sources of distortion present in the output drive circuit (e.g., the power transformer 1560, the power amplifier 1620), voltage and current feedback data based on the drive signal may be input into an algorithm, such as an error control algorithm implemented by the processor 1740, which compensates for distortion by suitably pre-distorting or modifying the waveform samples stored in the LUT on a dynamic, ongoing basis (e.g., in real-time). In one aspect, the amount or degree of pre-distortion applied to the LUT samples may be based on the error between a computed motional branch current and a desired current waveform shape, with the error being determined on a sample-by sample basis. In this way, the pre-distorted LUT samples, when processed through the drive circuit, may result in a motional branch drive signal having the desired waveform shape (e.g., sinusoidal) for optimally driving the ultrasonic transducer. In such aspects, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1540 may further comprise an ADC 1780 and an ADC 1800 coupled to the output of the power transformer 1560 via respective isolation transformers 1820, 1840 for respectively sampling the voltage and current of drive signals output by the generator 1100. In certain aspects, the ADCs 1780, 1800 may be configured to sample at high speeds (e.g., 80 Msps) to enable oversampling of the drive signals. In one aspect, for example, the sampling speed of the ADCs 1780, 1800 may enable approximately 200× (depending on drive frequency) oversampling of the drive signals. In certain aspects, the sampling operations of the ADCs 1780, 1800 may be performed by a single ADC receiving input voltage and current signals via a two-way multiplexer. The use of high-speed sampling in aspects of the generator 1100 may enable, among other things, calculation of the complex current flowing through the motional branch (which may be used in certain aspects to implement DDS-based waveform shape control described above), accurate digital filtering of the sampled signals, and calculation of real power consumption with a high degree of precision. Voltage and current feedback data output by the ADCs 1780, 1800 may be received and processed (e.g., FIFO buffering, multiplexing) by the programmable logic device 1660 and stored in data memory for subsequent retrieval by, for example, the processor 1740. As noted above, voltage and current feedback data may be used as input to an algorithm for pre-distorting or modifying LUT waveform samples on a dynamic and ongoing basis. In certain aspects, this may require each stored voltage and current feedback data pair to be indexed based on, or otherwise associated with, a corresponding LUT sample that was output by the programmable logic device 1660 when the voltage and current feedback data pair was acquired. Synchronization of the LUT samples and the voltage and current feedback data in this manner contributes to the correct timing and stability of the pre-distortion algorithm.

In certain aspects, the voltage and current feedback data may be used to control the frequency and/or amplitude (e.g., current amplitude) of the drive signals. In one aspect, for example, voltage and current feedback data may be used to determine impedance phase, e.g., the phase difference between the voltage and current drive signals. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the processor 1740, for example, with the frequency control signal being supplied as input to a DDS control algorithm implemented by the programmable logic device 1660.

The impedance phase may be determined through Fourier analysis. In one aspect, the phase difference between the generator voltage $V_g(t)$ and generator current $I_g(t)$ driving signals may be determined using the Fast Fourier Transform (FFT) or the Discrete Fourier Transform (DFT) as follows:

$$V_g(t) = A_1 \cos(2\pi f_0 t + \varphi_1)$$

$$I_g(t) = A_2 \cos(2\pi f_0 t + \varphi_2)$$

$$V_g(f) = \frac{A_1}{2}(\delta(f - f_0) + \delta(f + f_0)) \exp\left(j2\pi f \frac{\varphi_1}{2\pi f_0}\right)$$

$$I_g(f) = \frac{A_2}{2}(\delta(f - f_0) + \delta(f + f_0)) \exp\left(j2\pi f \frac{\varphi_2}{2\pi f_0}\right)$$

Evaluating the Fourier Transform at the frequency of the sinusoid yields:

$$V_g(f_0) = \frac{A_1}{2}\delta(0)\exp(j\varphi_1) \quad \arg V(f_0) = \varphi_1$$

$$I_g(f_0) = \frac{A_2}{2}\delta(0)\exp(j\varphi_2) \quad \arg I(f_0) = \varphi_2$$

Other approaches include weighted least-squares estimation, Kalman filtering, and space-vector-based techniques. Virtually all of the processing in an FFT or DFT technique may be performed in the digital domain with the aid of the 2-channel high speed ADC 1780, 1800, for example. In one technique, the digital signal samples of the voltage and current signals are Fourier transformed with an FFT or a DFT. The phase angle φ at any point in time can be calculated by:

φ=2πft+φ₀ where φ is the phase angle, f is the frequency, t is time, and φ₀ is the phase at t=0.

Another technique for determining the phase difference between the voltage $V_g(t)$ and current $I_g(t)$ signals is the zero-crossing method and produces highly accurate results. For voltage $V_g(t)$ and current $I_g(t)$ signals having the same frequency, each negative to positive zero-crossing of voltage signal $V_g(t)$ triggers the start of a pulse, while each negative to positive zero-crossing of current signal $I_g(t)$ triggers the end of the pulse. The result is a pulse train with a pulse width proportional to the phase angle between the voltage signal and the current signal. In one aspect, the pulse train may be passed through an averaging filter to yield a measure of the phase difference. Furthermore, if the positive to negative zero crossings also are used in a similar manner, and the results averaged, any effects of DC and harmonic components can be reduced. In one implementation, the analog voltage $V_g(t)$ and current $I_g(t)$ signals are converted to digital signals that are high if the analog signal is positive and low if the analog signal is negative. High accuracy phase estimates require sharp transitions between high and low. In one aspect, a Schmitt trigger along with an RC stabilization network may be employed to convert the analog signals into digital signals. In other aspects, an edge triggered RS flip-flop and ancillary circuitry may be employed. In yet another aspect, the zero-crossing technique may employ an eXclusive OR (XOR) gate.

Other techniques for determining the phase difference between the voltage and current signals include Lissajous figures and monitoring the image; methods such as the three-voltmeter method, the crossed-coil method, vector voltmeter and vector impedance methods; and using phase standard instruments, phase-locked loops, and other techniques as described in Phase Measurement, Peter O'Shea, 2000 CRC Press LLC, <http://www.engnetbase.com>, which is incorporated herein by reference.

In another aspect, for example, the current feedback data may be monitored in order to maintain the current amplitude of the drive signal at a current amplitude setpoint. The current amplitude setpoint may be specified directly or determined indirectly based on specified voltage amplitude and power setpoints. In certain aspects, control of the current amplitude may be implemented by control algorithm, such as, for example, a proportional-integral-derivative (PID) control algorithm, in the processor 1740. Variables controlled by the control algorithm to suitably control the current amplitude of the drive signal may include, for example, the scaling of the LUT waveform samples stored in the programmable logic device 1660 and/or the full-scale output voltage of the DAC 1680 (which supplies the input to the power amplifier 1620) via a DAC 1860.

The non-isolated stage 1540 may further comprise a processor 1900 for providing, among other things, user interface (UI) functionality. In one aspect, the processor 1900 may comprise an Atmel AT91 SAM9263 processor having an ARM 926EJ-S core, available from Atmel Corporation, San Jose, Calif., for example. Examples of UI functionality supported by the processor 1900 may include audible and visual user feedback, communication with peripheral devices (e.g., via a Universal Serial Bus (USB) interface), communication with a foot switch 1430, communication with an input device 2150 (e.g., a touch screen display) and communication with an output device 2140 (e.g., a speaker). The processor 1900 may communicate with the processor 1740 and the programmable logic device (e.g., via a serial peripheral interface (SPI) bus). Although the processor 1900 may primarily support UI functionality, it may also coordinate with the processor 1740 to implement hazard mitigation in certain aspects. For example, the processor 1900 may be programmed to monitor various aspects of user input and/or other inputs (e.g., touch screen inputs 2150, foot switch 1430 inputs, temperature sensor inputs 2160) and may disable the drive output of the generator 1100 when an erroneous condition is detected.

In certain aspects, both the processor 1740 (FIGS. 7, 8A) and the processor 1900 (FIGS. 7, 8B) may determine and monitor the operating state of the generator 1100. For processor 1740, the operating state of the generator 1100 may dictate, for example, which control and/or diagnostic processes are implemented by the processor 1740. For processor 1900, the operating state of the generator 1100 may dictate, for example, which elements of a user interface (e.g., display screens, sounds) are presented to a user. The processors 1740, 1900 may independently maintain the current operating state of the generator 1100 and recognize and evaluate possible transitions out of the current operating state. The processor 1740 may function as the master in this relationship and determine when transitions between operating states are to occur. The processor 1900 may be aware of valid transitions between operating states and may confirm if a particular transition is appropriate. For example, when the processor 1740 instructs the processor 1900 to transition to a specific state, the processor 1900 may verify that the requested transition is valid. In the event that a requested transition between states is determined to be invalid by the processor 1900, the processor 1900 may cause the generator 1100 to enter a failure mode.

The non-isolated stage 1540 may further comprise a controller 1960 (FIGS. 7, 8B) for monitoring input devices 2150 (e.g., a capacitive touch sensor used for turning the generator 1100 on and off, a capacitive touch screen). In certain aspects, the controller 1960 may comprise at least one processor and/or other controller device in communication with the processor 1900. In one aspect, for example, the controller 1960 may comprise a processor (e.g., a Mega168 8-bit controller available from Atmel) configured to monitor user input provided via one or more capacitive touch sensors. In one aspect, the controller 1960 may comprise a touch screen controller (e.g., a QT5480 touch screen controller available from Atmel) to control and manage the acquisition of touch data from a capacitive touch screen.

In certain aspects, when the generator 1100 is in a "power off" state, the controller 1960 may continue to receive operating power (e.g., via a line from a power supply of the generator 1100, such as the power supply 2110 (FIG. 7) discussed below). In this way, the controller 1960 may continue to monitor an input device 2150 (e.g., a capacitive touch sensor located on a front panel of the generator 1100) for turning the generator 1100 on and off. When the generator 1100 is in the "power off" state, the controller 1960 may wake the power supply (e.g., enable operation of one or more DC/DC voltage converters 2130 (FIG. 7) of the power supply 2110) if activation of the "on/off" input device 2150 by a user is detected. The controller 1960 may therefore initiate a sequence for transitioning the generator 1100 to a "power on" state. Conversely, the controller 1960 may initiate a sequence for transitioning the generator 1100 to the "power off" state if activation of the "on/off" input device 2150 is detected when the generator 1100 is in the "power on" state. In certain aspects, for example, the controller 1960 may report activation of the "on/off" input device 2150 to the processor 1900, which in turn implements the necessary process sequence for transitioning the generator 1100 to the "power off" state. In such aspects, the controller 1960 may have no independent ability for causing the removal of power from the generator 1100 after its "power on" state has been established.

In certain aspects, the controller 1960 may cause the generator 1100 to provide audible or other sensory feedback for alerting the user that a "power on" or "power off" sequence has been initiated. Such an alert may be provided at the beginning of a "power on" or "power off" sequence and prior to the commencement of other processes associated with the sequence.

In certain aspects, the isolated stage 1520 may comprise an instrument interface circuit 1980 to, for example, provide a communication interface between a control circuit of a surgical device (e.g., a control circuit comprising handpiece switches) and components of the non-isolated stage 1540, such as, for example, the programmable logic device 1660, the processor 1740 and/or the processor 1900. The instrument interface circuit 1980 may exchange information with components of the non-isolated stage 1540 via a communication link that maintains a suitable degree of electrical isolation between the stages 1520, 1540, such as, for example, an infrared (IR)-based communication link. Power may be supplied to the instrument interface circuit 1980 using, for example, a low-dropout voltage regulator powered by an isolation transformer driven from the non-isolated stage 1540.

In one aspect, the instrument interface circuit 1980 may comprise a programmable logic device 2000 (e.g., an FPGA) in communication with a signal conditioning circuit 2020 (FIG. 7 and FIG. 8C). The signal conditioning circuit 2020 may be configured to receive a periodic signal from the programmable logic device 2000 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 1100 to the surgical device) and monitored to determine a state or configuration of the control circuit. For example, the control circuit may comprise a number of switches, resistors and/or diodes to modify one or more characteristics (e.g., amplitude, rectification) of the interrogation signal such that a state or configuration of the control circuit is uniquely discernible based on the one or more characteristics. In one aspect, for example, the signal conditioning circuit 2020 may comprise an ADC for generating samples of a voltage signal appearing across inputs of the control circuit resulting from passage of interrogation signal therethrough. The programmable logic device 2000 (or a component of the non-isolated stage 1540) may then determine the state or configuration of the control circuit based on the ADC samples.

In one aspect, the instrument interface circuit 1980 may comprise a first data circuit interface 2040 to enable information exchange between the programmable logic device 2000 (or other element of the instrument interface circuit 1980) and a first data circuit disposed in or otherwise associated with a surgical device. In certain aspects, for example, a first data circuit 2060 may be disposed in a cable integrally attached to a surgical device handpiece, or in an adaptor for interfacing a specific surgical device type or model with the generator 1100. In certain aspects, the first data circuit may comprise a non-volatile storage device, such as an electrically erasable programmable read-only memory (EEPROM) device. In certain aspects and referring again to FIG. 7, the first data circuit interface 2040 may be implemented separately from the programmable logic device 2000 and comprise suitable circuitry (e.g., discrete logic devices, a processor) to enable communication between the programmable logic device 2000 and the first data circuit. In other aspects, the first data circuit interface 2040 may be integral with the programmable logic device 2000.

In certain aspects, the first data circuit 2060 may store information pertaining to the particular surgical device with which it is associated. Such information may include, for example, a model number, a serial number, a number of operations in which the surgical device has been used, and/or any other type of information. This information may be read by the instrument interface circuit 1980 (e.g., by the programmable logic device 2000), transferred to a component of the non-isolated stage 1540 (e.g., to programmable logic device 1660, processor 1740 and/or processor 1900) for presentation to a user via an output device 2140 and/or for controlling a function or operation of the generator 1100. Additionally, any type of information may be communicated to first data circuit 2060 for storage therein via the first data circuit interface 2040 (e.g., using the programmable logic device 2000). Such information may comprise, for example, an updated number of operations in which the surgical device has been used and/or dates and/or times of its usage.

As discussed previously, a surgical instrument may be detachable from a handpiece (e.g., instrument 1106 may be detachable from handpiece 1107) to promote instrument interchangeability and/or disposability. In such cases, known generators may be limited in their ability to recognize particular instrument configurations being used and to optimize control and diagnostic processes accordingly. The addition of readable data circuits to surgical device instruments to address this issue is problematic from a compatibility standpoint, however. For example, it may be impractical to design a surgical device to maintain backward compatibility with generators that lack the requisite data reading functionality due to, for example, differing signal schemes, design complexity and cost. Other aspects of instruments address these concerns by using data circuits that may be implemented in existing surgical instruments economically and with minimal design changes to preserve compatibility of the surgical devices with current generator platforms.

Additionally, aspects of the generator 1100 may enable communication with instrument-based data circuits. For example, the generator 1100 may be configured to communicate with a second data circuit (e.g., a data circuit) contained in an instrument (e.g., instrument 1104, 1106 or 1108) of a surgical device. The instrument interface circuit 1980 may comprise a second data circuit interface 2100 to enable this communication. In one aspect, the second data circuit interface 2100 may comprise a tri-state digital interface, although other interfaces may also be used. In certain aspects, the second data circuit may generally be any circuit for transmitting and/or receiving data. In one aspect, for example, the second data circuit may store information pertaining to the particular surgical instrument with which it is associated. Such information may include, for example, a model number, a serial number, a number of operations in which the surgical instrument has been used, and/or any other type of information. Additionally or alternatively, any type of information may be communicated to the second data circuit for storage therein via the second data circuit interface 2100 (e.g., using the programmable logic device 2000). Such information may comprise, for example, an updated number of operations in which the instrument has been used and/or dates and/or times of its usage. In certain aspects, the second data circuit may transmit data acquired by one or more sensors (e.g., an instrument-based temperature sensor). In certain aspects, the second data circuit may receive data from the generator 1100 and provide an indication to a user (e.g., an LED indication or other visible indication) based on the received data.

In certain aspects, the second data circuit and the second data circuit interface 2100 may be configured such that communication between the programmable logic device 2000 and the second data circuit can be effected without the need to provide additional conductors for this purpose (e.g., dedicated conductors of a cable connecting a handpiece to the generator 1100). In one aspect, for example, information may be communicated to and from the second data circuit using a one-wire bus communication scheme implemented on existing cabling, such as one of the conductors used transmit interrogation signals from the signal conditioning circuit 2020 to a control circuit in a handpiece. In this way, design changes or modifications to the surgical device that might otherwise be necessary are minimized or reduced. Moreover, because different types of communications can be implemented over a common physical channel (either with or without frequency-band separation), the presence of a second data circuit may be "invisible" to generators that do not have the requisite data reading functionality, thus enabling backward compatibility of the surgical device instrument.

In certain aspects, the isolated stage 1520 may comprise at least one blocking capacitor 2960-1 (FIG. 8C) connected to the drive signal output 1600b to prevent passage of DC current to a patient. A single blocking capacitor may be required to comply with medical regulations or standards, for example. While failure in single-capacitor designs is relatively uncommon, such failure may nonetheless have negative consequences. In one aspect, a second blocking capacitor 2960-2 may be provided in series with the blocking capacitor 2960-1, with current leakage from a point between the blocking capacitors 2960-1, 2960-2 being monitored by, for example, an ADC 2980 for sampling a voltage induced by leakage current. The samples may be received by the programmable logic device 2000, for example. Based on changes in the leakage current (as indicated by the voltage samples in the aspect of FIG. 7), the generator 1100 may determine when at least one of the blocking capacitors 2960-1, 2960-2 has failed. Accordingly, the aspect of FIG. 7 may provide a benefit over single-capacitor designs having a single point of failure.

In certain aspects, the non-isolated stage 1540 may comprise a power supply 2110 for outputting DC power at a suitable voltage and current. The power supply may comprise, for example, a 400 W power supply for outputting a 48 VDC system voltage. As discussed above, the power supply 2110 may further comprise one or more DC/DC voltage converters 2130 for receiving the output of the power supply to generate DC outputs at the voltages and currents required by the various components of the generator 1100. As discussed above in connection with the controller 1960, one or more of the DC/DC voltage converters 2130 may receive an input from the controller 1960 when activation of the "on/off" input device 2150 by a user is detected by the controller 1960 to enable operation of, or wake, the DC/DC voltage converters 2130.

Figure 9A:
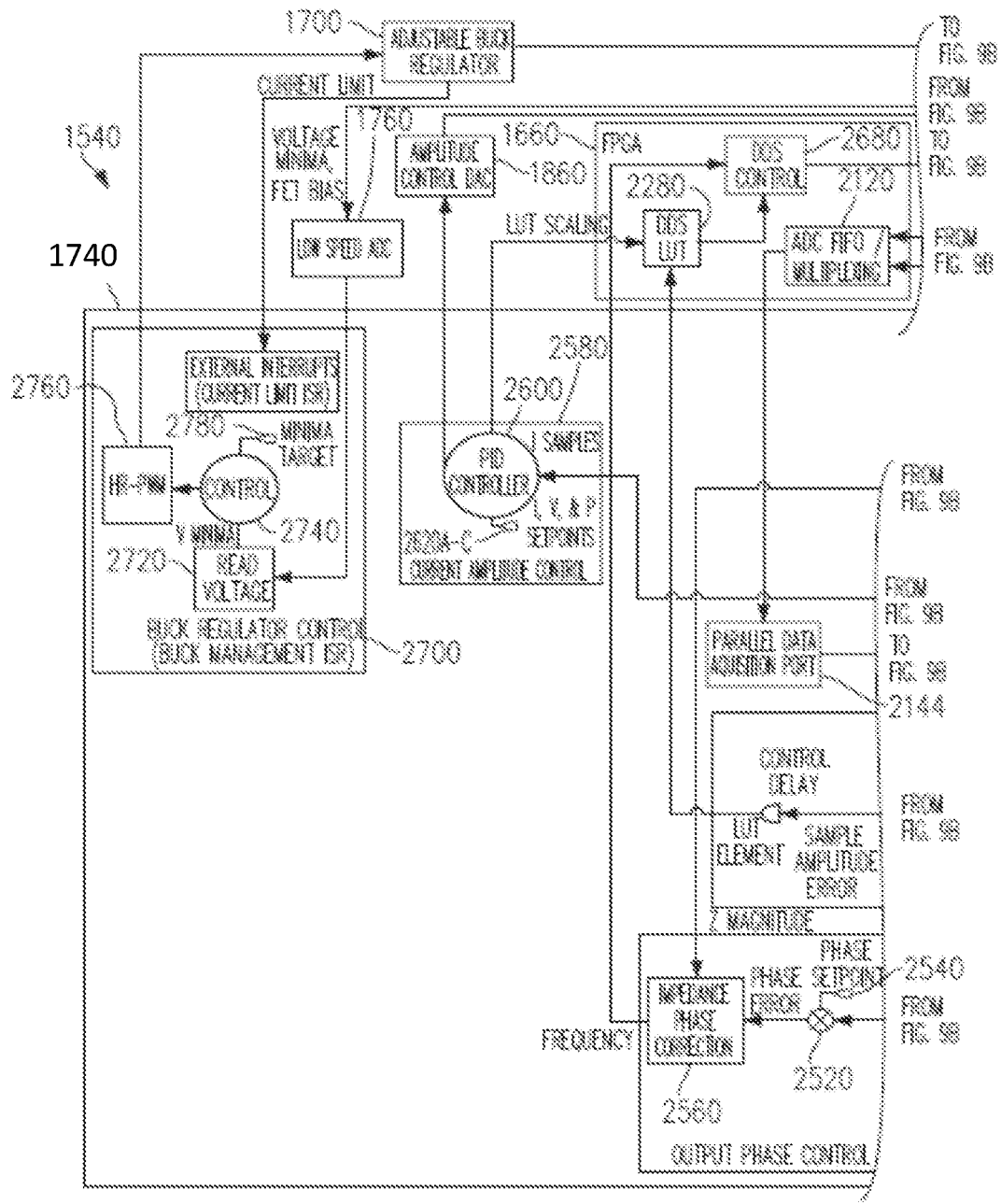
FIGS. 9A-9B are structural and functional aspects of a generator, in accordance with at least one aspect of the present disclosure.
Figure 9B:
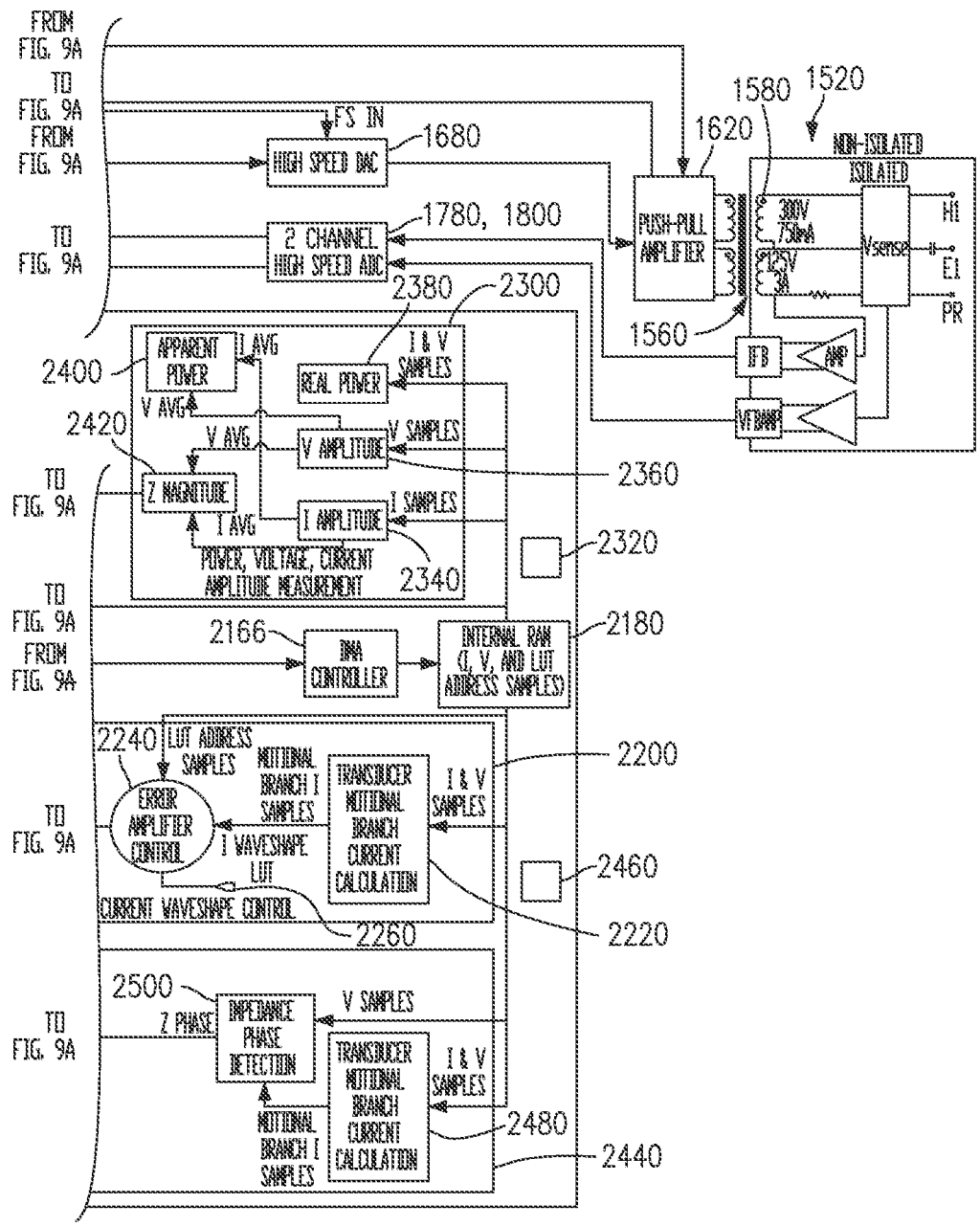

FIGS. 9A-9B illustrate certain functional and structural aspects of one aspect of the generator 1100. Feedback indicating current and voltage output from the secondary winding 1580 of the power transformer 1560 is received by the ADCs 1780, 1800, respectively. As shown, the ADCs 1780, 1800 may be implemented as a 2-channel ADC and may sample the feedback signals at a high speed (e.g., 80 Msps) to enable oversampling (e.g., approximately 200× oversampling) of the drive signals. The current and voltage feedback signals may be suitably conditioned in the analog domain (e.g., amplified, filtered) prior to processing by the ADCs 1780, 1800. Current and voltage feedback samples from the ADCs 1780, 1800 may be individually buffered and subsequently multiplexed or interleaved into a single data stream within block 2120 of the programmable logic device 1660. In the aspect of FIGS. 9A-9B, the programmable logic device 1660 comprises an FPGA.

The multiplexed current and voltage feedback samples may be received by a parallel data acquisition port (PDAP) implemented within block 2144 of the processor 1740. The PDAP may comprise a packing unit for implementing any of a number of methodologies for correlating the multiplexed feedback samples with a memory address. In one aspect, for example, feedback samples corresponding to a particular LUT sample output by the programmable logic device 1660 may be stored at one or more memory addresses that are correlated or indexed with the LUT address of the LUT sample. In another aspect, feedback samples corresponding to a particular LUT sample output by the programmable logic device 1660 may be stored, along with the LUT address of the LUT sample, at a common memory location. In any event, the feedback samples may be stored such that the address of the LUT sample from which a particular set of feedback samples originated may be subsequently ascertained. As discussed above, synchronization of the LUT sample addresses and the feedback samples in this way contributes to the correct timing and stability of the pre-distortion algorithm. A direct memory access (DMA) controller implemented at block 2166 of the processor 1740 may store the feedback samples (and any LUT sample address data, where applicable) at a designated memory location 2180 of the processor 1740 (e.g., internal RAM).

Block 2200 of the processor 1740 may implement a pre-distortion algorithm for pre-distorting or modifying the LUT samples stored in the programmable logic device 1660 on a dynamic, ongoing basis. As discussed above, pre-distortion of the LUT samples may compensate for various sources of distortion present in the output drive circuit of the generator 1100. The pre-distorted LUT samples, when processed through the drive circuit, will therefore result in a drive signal having the desired waveform shape (e.g., sinusoidal) for optimally driving the ultrasonic transducer.

At block 2220 of the pre-distortion algorithm, the current through the motional branch of the ultrasonic transducer is determined. The motional branch current may be determined using Kirchhoff's Current Law based on, for example, the current and voltage feedback samples stored at memory location 2180 (which, when suitably scaled, may be representative of $I_g$ and $V_g$ in the model of FIG. 6 discussed above), a value of the ultrasonic transducer static capacitance $C_0$ (measured or known a priori) and a known value of the drive frequency. A motional branch current sample for each set of stored current and voltage feedback samples associated with a LUT sample may be determined.

At block 2240 of the pre-distortion algorithm, each motional branch current sample determined at block 2220 is compared to a sample of a desired current waveform shape to determine a difference, or sample amplitude error, between the compared samples. For this determination, the sample of the desired current waveform shape may be supplied, for example, from a waveform shape LUT 2260 containing amplitude samples for one cycle of a desired current waveform shape. The particular sample of the desired current waveform shape from the LUT 2260 used for the comparison may be dictated by the LUT sample address associated with the motional branch current sample used in the comparison. Accordingly, the input of the motional branch current to block 2240 may be synchronized with the input of its associated LUT sample address to block 2240. The LUT samples stored in the programmable logic device 1660 and the LUT samples stored in the waveform shape LUT 2260 may therefore be equal in number. In certain aspects, the desired current waveform shape represented by the LUT samples stored in the waveform shape LUT 2260 may be a fundamental sine wave. Other waveform shapes may be desirable. For example, it is contemplated that a fundamental sine wave for driving main longitudinal motion of an ultrasonic transducer superimposed with one or more other drive signals at other frequencies, such as a third order harmonic for driving at least two mechanical resonances for beneficial vibrations of transverse or other modes, could be used.

Each value of the sample amplitude error determined at block 2240 may be transmitted to the LUT of the programmable logic device 1660 (shown at block 2280 in FIG. 9A) along with an indication of its associated LUT address. Based on the value of the sample amplitude error and its associated address (and, optionally, values of sample amplitude error for the same LUT address previously received), the LUT 2280 (or other control block of the programmable logic device 1660) may pre-distort or modify the value of the LUT sample stored at the LUT address such that the sample amplitude error is reduced or minimized. It will be appreciated that such pre-distortion or modification of each LUT sample in an iterative manner across the entire range of LUT addresses will cause the waveform shape of the generator's output current to match or conform to the desired current waveform shape represented by the samples of the waveform shape LUT 2260.

Current and voltage amplitude measurements, power measurements and impedance measurements may be determined at block 2300 of the processor 1740 based on the current and voltage feedback samples stored at memory location 2180. Prior to the determination of these quantities, the feedback samples may be suitably scaled and, in certain aspects, processed through a suitable filter 2320 to remove noise resulting from, for example, the data acquisition process and induced harmonic components. The filtered voltage and current samples may therefore substantially represent the fundamental frequency of the generator's drive output signal. In certain aspects, the filter 2320 may be a finite impulse response (FIR) filter applied in the frequency domain. Such aspects may use the Fast Fourier Transform (FFT) of the output drive signal current and voltage signals. In certain aspects, the resulting frequency spectrum may be used to provide additional generator functionality. In one aspect, for example, the ratio of the second and/or third order harmonic component relative to the fundamental frequency component may be used as a diagnostic indicator.

At block 2340 (FIG. 9B), a root mean square (RMS) calculation may be applied to a sample size of the current feedback samples representing an integral number of cycles of the drive signal to generate a measurement $I_{rms}$ representing the drive signal output current.

At block 2360, a root mean square (RMS) calculation may be applied to a sample size of the voltage feedback samples representing an integral number of cycles of the drive signal to determine a measurement $V_{rms}$ representing the drive signal output voltage.

At block 2380, the current and voltage feedback samples may be multiplied point by point, and a mean calculation is applied to samples representing an integral number of cycles of the drive signal to determine a measurement $P_r$ of the generator's real output power.

At block 2400, measurement $P_a$ of the generator's apparent output power may be determined as the product $V_{rms} \cdot I_{rms}$.

At block 2420, measurement $Z_m$ of the load impedance magnitude may be determined as the quotient $V_{rms}/V_{rms}$.

In certain aspects, the quantities $I_{rms}$, $V_{rms}$, $P_r$, $P_a$ and $Z_m$ determined at blocks 2340, 2360, 2380, 2400 and 2420 may be used by the generator 1100 to implement any of a number of control and/or diagnostic processes. In certain aspects, any of these quantities may be communicated to a user via, for example, an output device 2140 integral with the generator 1100 or an output device 2140 connected to the generator 1100 through a suitable communication interface (e.g., a USB interface). Various diagnostic processes may include, without limitation, handpiece integrity, instrument integrity, instrument attachment integrity, instrument overload, approaching instrument overload, frequency lock failure, over-voltage condition, over-current condition, over-power condition, voltage sense failure, current sense failure, audio indication failure, visual indication failure, short circuit condition, power delivery failure, or blocking capacitor failure, for example.

Block 2440 of the processor 1740 may implement a phase control algorithm for determining and controlling the impedance phase of an electrical load (e.g., the ultrasonic transducer) driven by the generator 1100. As discussed above, by controlling the frequency of the drive signal to minimize or reduce the difference between the determined impedance phase and an impedance phase setpoint (e.g., 0°), the effects of harmonic distortion may be minimized or reduced, and the accuracy of the phase measurement increased.

The phase control algorithm receives as input the current and voltage feedback samples stored in the memory location 2180. Prior to their use in the phase control algorithm, the feedback samples may be suitably scaled and, in certain aspects, processed through a suitable filter 2460 (which may be identical to filter 2320) to remove noise resulting from the data acquisition process and induced harmonic components, for example. The filtered voltage and current samples may therefore substantially represent the fundamental frequency of the generator's drive output signal.

At block 2480 of the phase control algorithm, the current through the motional branch of the ultrasonic transducer is determined. This determination may be identical to that described above in connection with block 2220 of the pre-distortion algorithm. The output of block 2480 may thus be, for each set of stored current and voltage feedback samples associated with a LUT sample, a motional branch current sample.

At block 2500 of the phase control algorithm, impedance phase is determined based on the synchronized input of motional branch current samples determined at block 2480 and corresponding voltage feedback samples. In certain aspects, the impedance phase is determined as the average of the impedance phase measured at the rising edge of the waveforms and the impedance phase measured at the falling edge of the waveforms.

At block 2520 of the of the phase control algorithm, the value of the impedance phase determined at block 2500 is compared to phase setpoint 2540 to determine a difference, or phase error, between the compared values.

At block 2560 (FIG. 9A) of the phase control algorithm, based on a value of phase error determined at block 2520 and the impedance magnitude determined at block 2420, a frequency output for controlling the frequency of the drive signal is determined. The value of the frequency output may be continuously adjusted by the block 2560 and transferred to a DDS control block 2680 (discussed below) in order to maintain the impedance phase determined at block 2500 at the phase setpoint (e.g., zero phase error). In certain aspects, the impedance phase may be regulated to a 0° phase setpoint. In this way, any harmonic distortion will be centered about the crest of the voltage waveform, enhancing the accuracy of phase impedance determination.

Block 2580 of the processor 1740 may implement an algorithm for modulating the current amplitude of the drive signal in order to control the drive signal current, voltage and power in accordance with user specified setpoints, or in accordance with requirements specified by other processes or algorithms implemented by the generator 1100. Control of these quantities may be realized, for example, by scaling the LUT samples in the LUT 2280 and/or by adjusting the full-scale output voltage of the DAC 1680 (which supplies the input to the power amplifier 1620) via a DAC 1860. Block 2600 (which may be implemented as a PID controller in certain aspects) may receive, as input, current feedback samples (which may be suitably scaled and filtered) from the memory location 2180. The current feedback samples may be compared to a "current demand" $I_d$ value dictated by the controlled variable (e.g., current, voltage or power) to determine if the drive signal is supplying the necessary current. In aspects in which drive signal current is the control variable, the current demand $I_d$ may be specified directly by a current setpoint 2620A ($I_{sp}$). For example, an RMS value of the current feedback data (determined as in block 2340) may be compared to user-specified RMS current setpoint $I_{sp}$ to determine the appropriate controller action. If, for example, the current feedback data indicates an RMS value less than the current setpoint $I_{sp}$, LUT scaling and/or the full-scale output voltage of the DAC 1680 may be adjusted by the block 2600 such that the drive signal current is increased. Conversely, block 2600 may adjust LUT scaling and/or the full-scale output voltage of the DAC 1680 to decrease the drive signal current when the current feedback data indicates an RMS value greater than the current setpoint $I_{sp}$.

In aspects in which the drive signal voltage is the control variable, the current demand $I_d$ may be specified indirectly, for example, based on the current required to maintain a desired voltage setpoint 2620B ($V_{sp}$) given the load impedance magnitude $Z_m$ measured at block 2420 (e.g. $I_d = V_{sp}/Z_m$). Similarly, in aspects in which drive signal power is the control variable, the current demand $I_d$ may be specified indirectly, for example, based on the current required to maintain a desired power setpoint 2620C ($P_{sp}$) given the voltage $V_{rms}$ measured at blocks 2360 (e.g. $I_d = P_{sp}/V_{rms}$).

Block 2680 (FIG. 9A) may implement a DDS control algorithm for controlling the drive signal by recalling LUT samples stored in the LUT 2280. In certain aspects, the DDS control algorithm may be a numerically-controlled oscillator (NCO) algorithm for generating samples of a waveform at a fixed clock rate using a point (memory location)-skipping technique. The NCO algorithm may implement a phase accumulator, or frequency-to-phase converter, that functions as an address pointer for recalling LUT samples from the LUT 2280. In one aspect, the phase accumulator may be a D step size, modulo N phase accumulator, where D is a positive integer representing a frequency control value, and N is the number of LUT samples in the LUT 2280. A frequency control value of D=1, for example, may cause the phase accumulator to sequentially point to every address of the LUT 2280, resulting in a waveform output replicating the waveform stored in the LUT 2280. When D>1, the phase accumulator may skip addresses in the LUT 2280, resulting in a waveform output having a higher frequency. Accordingly, the frequency of the waveform generated by the DDS control algorithm may therefore be controlled by suitably varying the frequency control value. In certain aspects, the frequency control value may be determined based on the output of the phase control algorithm implemented at block 2440. The output of block 2680 may supply the input of DAC 1680, which in turn supplies a corresponding analog signal to an input of the power amplifier 1620.

Block 2700 of the processor 1740 may implement a switch-mode converter control algorithm for dynamically modulating the rail voltage of the power amplifier 1620 based on the waveform envelope of the signal being amplified, thereby improving the efficiency of the power amplifier 1620. In certain aspects, characteristics of the waveform envelope may be determined by monitoring one or more signals contained in the power amplifier 1620. In one aspect, for example, characteristics of the waveform envelope may be determined by monitoring the minima of a drain voltage (e.g., a MOSFET drain voltage) that is modulated in accordance with the envelope of the amplified signal. A minima voltage signal may be generated, for example, by a voltage minima detector coupled to the drain voltage. The minima voltage signal may be sampled by ADC 1760, with the output minima voltage samples being received at block 2720 of the switch-mode converter control algorithm. Based on the values of the minima voltage samples, block 2740 may control a PWM signal output by a PWM generator 2760, which, in turn, controls the rail voltage supplied to the power amplifier 1620 by the switch-mode regulator 1700. In certain aspects, as long as the values of the minima voltage samples are less than a minima target 2780 input into block 2720, the rail voltage may be modulated in accordance with the waveform envelope as characterized by the minima voltage samples. When the minima voltage samples indicate low envelope power levels, for example, block 2740 may cause a low rail voltage to be supplied to the power amplifier 1620, with the full rail voltage being supplied only when the minima voltage samples indicate maximum envelope power levels. When the minima voltage samples fall below the minima target 2780, block 2740 may cause the rail voltage to be maintained at a minimum value suitable for ensuring proper operation of the power amplifier 1620.

Figure 10:
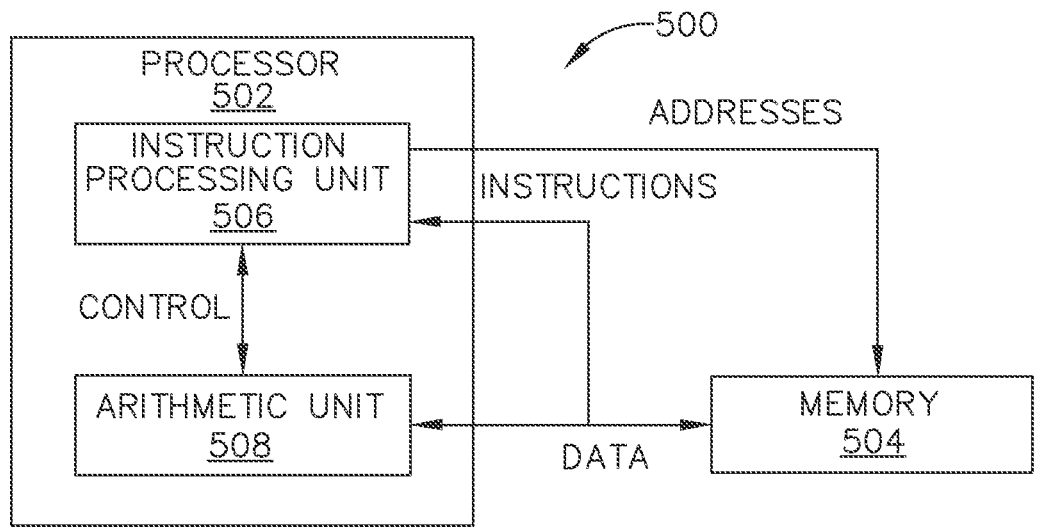
FIG. 10 illustrates a control circuit configured to control aspects of the surgical instrument or tool, in accordance with at least one aspect of the present disclosure.

FIG. 10 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 11:
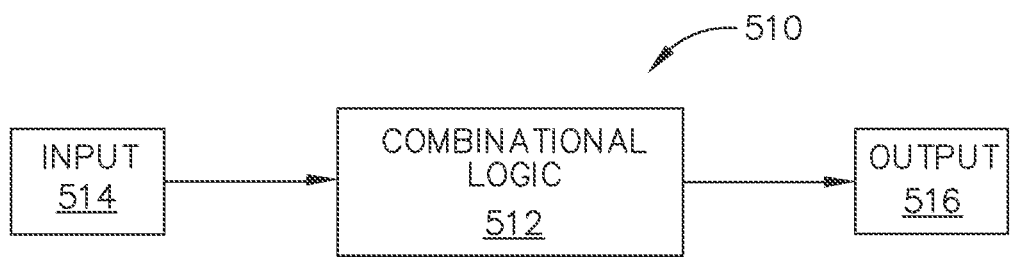
FIG. 11 illustrates a combinational logic circuit configured to control aspects of the surgical instrument or tool, in accordance with at least one aspect of the present disclosure.

FIG. 11 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 12:
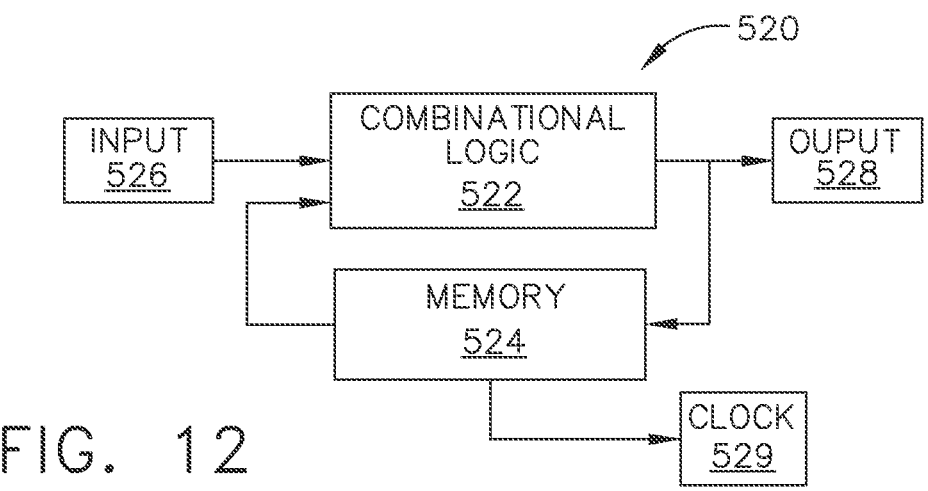
FIG. 12 illustrates a sequential logic circuit configured to control aspects of the surgical instrument or tool, in accordance with at least one aspect of the present disclosure.

FIG. 12 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 13:
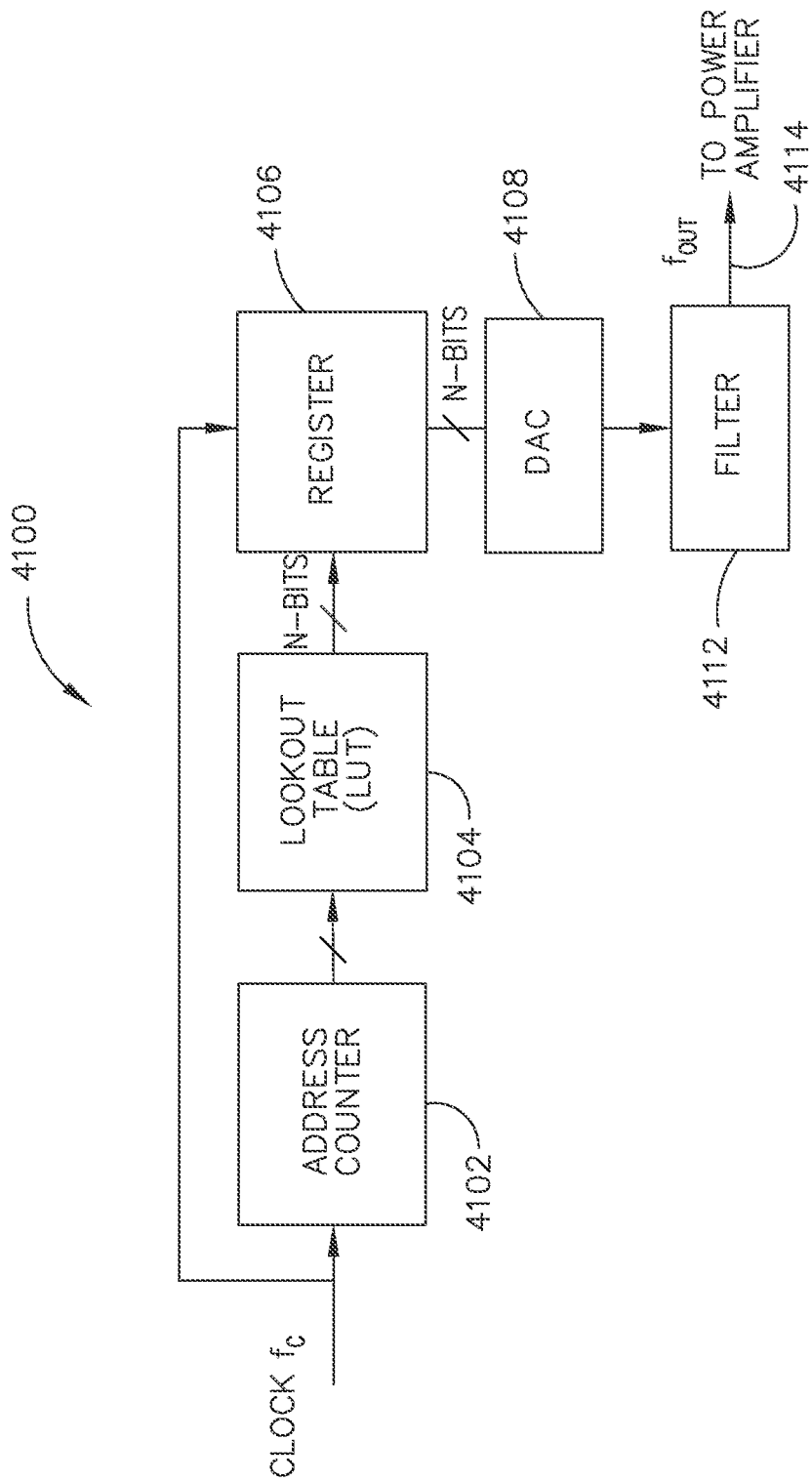
FIG. 13 illustrates one aspect of a fundamental architecture for a digital synthesis circuit such as a direct digital synthesis (DDS) circuit configured to generate a plurality of wave shapes for the electrical signal waveform for use in a surgical instrument, in accordance with at least one aspect of the present disclosure.

In one aspect, the ultrasonic or high-frequency current generators of the surgical system 1000 may be configured to generate the electrical signal waveform digitally using a predetermined number of phase points stored in a lookup table to digitize the wave shape. The phase points may be stored in a table defined in a memory, a field programmable gate array (FPGA), or any suitable non-volatile memory. FIG. 13 illustrates one aspect of a fundamental architecture for a digital synthesis circuit such as a direct digital synthesis (DDS) circuit 4100 configured to generate a plurality of wave shapes for the electrical signal waveform. The generator software and digital controls may command the FPGA to scan the addresses in the lookup table 4104 which in turn provides varying digital input values to a DAC circuit 4108 that feeds a power amplifier. The addresses may be scanned according to a frequency of interest. Using such a lookup table 4104 enables generating various types of wave shapes that can be fed into tissue or into a transducer, an RF electrode, multiple transducers simultaneously, multiple RF electrodes simultaneously, or a combination of RF and ultrasonic instruments. Furthermore, multiple lookup tables 4104 that represent multiple wave shapes can be created, stored, and applied to tissue from a generator.

The waveform signal may be configured to control at least one of an output current, an output voltage, or an output power of an ultrasonic transducer and/or an RF electrode, or multiples thereof (e.g. two or more ultrasonic transducers and/or two or more RF electrodes). Further, where the surgical instrument comprises ultrasonic components, the waveform signal may be configured to drive at least two vibration modes of an ultrasonic transducer of the at least one surgical instrument. Accordingly, a generator may be configured to provide a waveform signal to at least one surgical instrument wherein the waveform signal corresponds to at least one wave shape of a plurality of wave shapes in a table. Further, the waveform signal provided to the two surgical instruments may comprise two or more wave shapes. The table may comprise information associated with a plurality of wave shapes and the table may be stored within the generator. In one aspect or example, the table may be a direct digital synthesis table, which may be stored in an FPGA of the generator. The table may be addressed by anyway that is convenient for categorizing wave shapes. According to one aspect, the table, which may be a direct digital synthesis table, is addressed according to a frequency of the waveform signal. Additionally, the information associated with the plurality of wave shapes may be stored as digital information in the table.

The analog electrical signal waveform may be configured to control at least one of an output current, an output voltage, or an output power of an ultrasonic transducer and/or an RF electrode, or multiples thereof (e.g., two or more ultrasonic transducers and/or two or more RF electrodes). Further, where the surgical instrument comprises ultrasonic components, the analog electrical signal waveform may be configured to drive at least two vibration modes of an ultrasonic transducer of the at least one surgical instrument. Accordingly, the generator circuit may be configured to provide an analog electrical signal waveform to at least one surgical instrument wherein the analog electrical signal waveform corresponds to at least one wave shape of a plurality of wave shapes stored in a lookup table 4104. Further, the analog electrical signal waveform provided to the two surgical instruments may comprise two or more wave shapes. The lookup table 4104 may comprise information associated with a plurality of wave shapes and the lookup table 4104 may be stored either within the generator circuit or the surgical instrument. In one aspect or example, the lookup table 4104 may be a direct digital synthesis table, which may be stored in an FPGA of the generator circuit or the surgical instrument. The lookup table 4104 may be addressed by anyway that is convenient for categorizing wave shapes. According to one aspect, the lookup table 4104, which may be a direct digital synthesis table, is addressed according to a frequency of the desired analog electrical signal waveform. Additionally, the information associated with the plurality of wave shapes may be stored as digital information in the lookup table 4104.

With the widespread use of digital techniques in instrumentation and communications systems, a digitally-controlled method of generating multiple frequencies from a reference frequency source has evolved and is referred to as direct digital synthesis. The basic architecture is shown in FIG. 13. In this simplified block diagram, a DDS circuit is coupled to a processor, controller, or a logic device of the generator circuit and to a memory circuit located in the generator circuit of the surgical system 1000. The DDS circuit 4100 comprises an address counter 4102, lookup table 4104, a register 4106, a DAC circuit 4108, and a filter 4112. A stable clock $f_c$ is received by the address counter 4102 and the register 4106 drives a programmable-read-only-memory (PROM) which stores one or more integral number of cycles of a sinewave (or other arbitrary waveform) in a lookup table 4104. As the address counter 4102 steps through memory locations, values stored in the lookup table 4104 are written to the register 4106, which is coupled to the DAC circuit 4108. The corresponding digital amplitude of the signal at the memory location of the lookup table 4104 drives the DAC circuit 4108, which in turn generates an analog output signal 4110. The spectral purity of the analog output signal 4110 is determined primarily by the DAC circuit 4108. The phase noise is basically that of the reference clock $f_c$. The first analog output signal 4110 output from the DAC circuit 4108 is filtered by the filter 4112 and a second analog output signal 4114 output by the filter 4112 is provided to an amplifier having an output coupled to the output of the generator circuit. The second analog output signal has a frequency $f_{out}$.

Because the DDS circuit 4100 is a sampled data system, issues involved in sampling must be considered: quantization noise, aliasing, filtering, etc. For instance, the higher order harmonics of the DAC circuit 4108 output frequencies fold back into the Nyquist bandwidth, making them unfilterable, whereas, the higher order harmonics of the output of phase-locked-loop (PLL) based synthesizers can be filtered. The lookup table 4104 contains signal data for an integral number of cycles. The final output frequency $f_{out}$ can be changed changing the reference clock frequency $f_c$ or by reprogramming the PROM.

Figure 15:
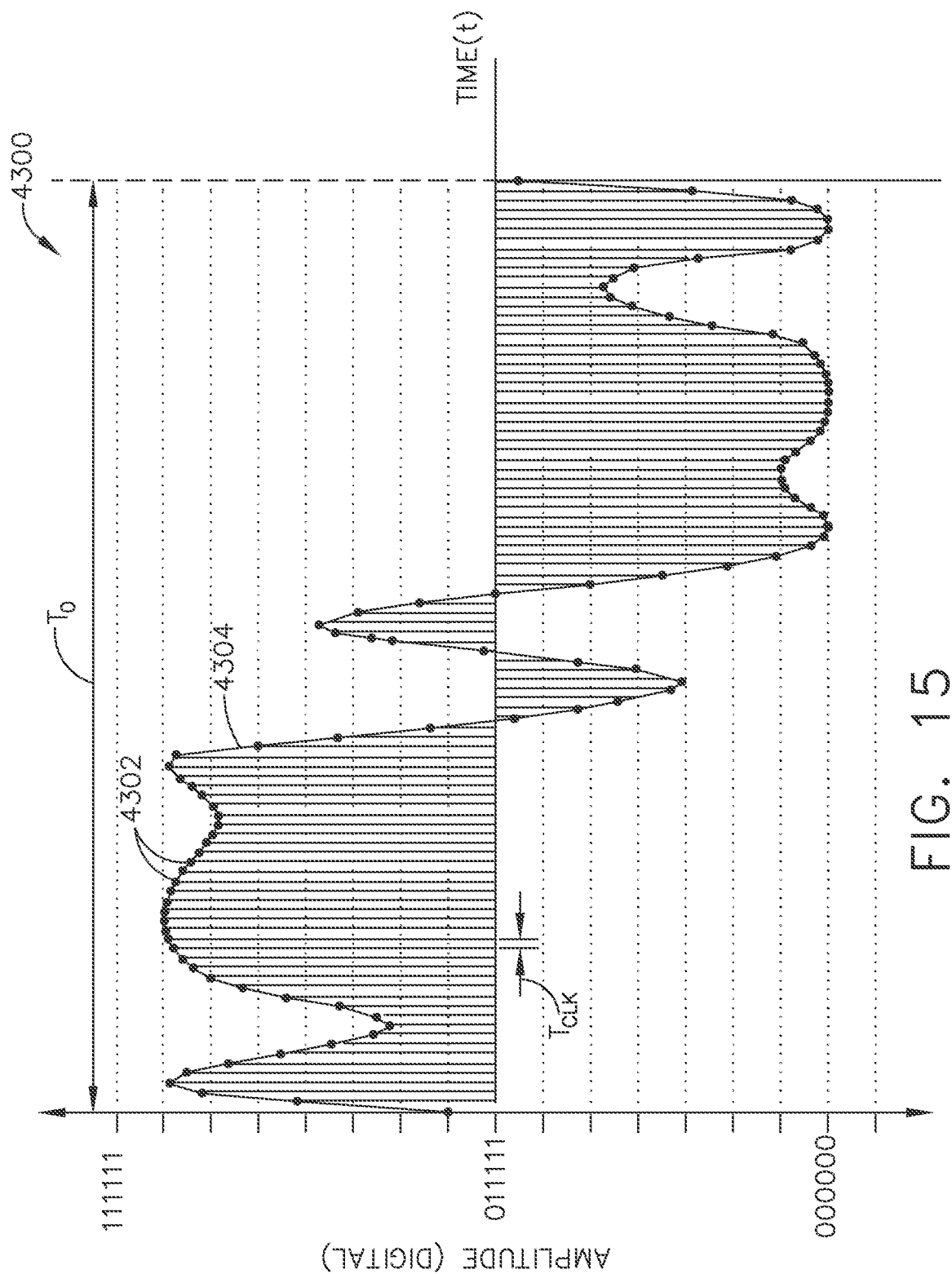
FIG. 15 illustrates one cycle of a discrete time digital electrical signal waveform, in accordance with at least one aspect of the present disclosure of an analog waveform (shown superimposed over a discrete time digital electrical signal waveform for comparison purposes), in accordance with at least one aspect of the present disclosure.

The DDS circuit 4100 may comprise multiple lookup tables 4104 where the lookup table 4104 stores a waveform represented by a predetermined number of samples, wherein the samples define a predetermined shape of the waveform. Thus multiple waveforms having a unique shape can be stored in multiple lookup tables 4104 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 4100 can create multiple wave shape lookup tables 4104 and during a tissue treatment procedure (e.g., "on-the-fly" or in virtual real time based on user or sensor inputs) switch between different wave shapes stored in separate lookup tables 4104 based on the tissue effect desired and/or tissue feedback. Accordingly, switching between wave shapes can be based on tissue impedance and other factors, for example. In other aspects, the lookup tables 4104 can store electrical signal waveforms shaped to maximize the power delivered into the tissue per cycle (i.e., trapezoidal or square wave). In other aspects, the lookup tables 4104 can store wave shapes synchronized in such way that they make maximizing power delivery by the multifunction surgical instrument of surgical system 1000 while delivering RF and ultrasonic drive signals. In yet other aspects, the lookup tables 4104 can store electrical signal waveforms to drive ultrasonic and RF therapeutic, and/or sub-therapeutic, energy simultaneously while maintaining ultrasonic frequency lock. Custom wave shapes specific to different instruments and their tissue effects can be stored in the non-volatile memory of the generator circuit or in the non-volatile memory (e.g., EEPROM) of the surgical system 1000 and be fetched upon connecting the multifunction surgical instrument to the generator circuit. An example of an exponentially damped sinusoid, as used in many high crest factor "coagulation" waveforms is shown in FIG. 15.

Figure 14:
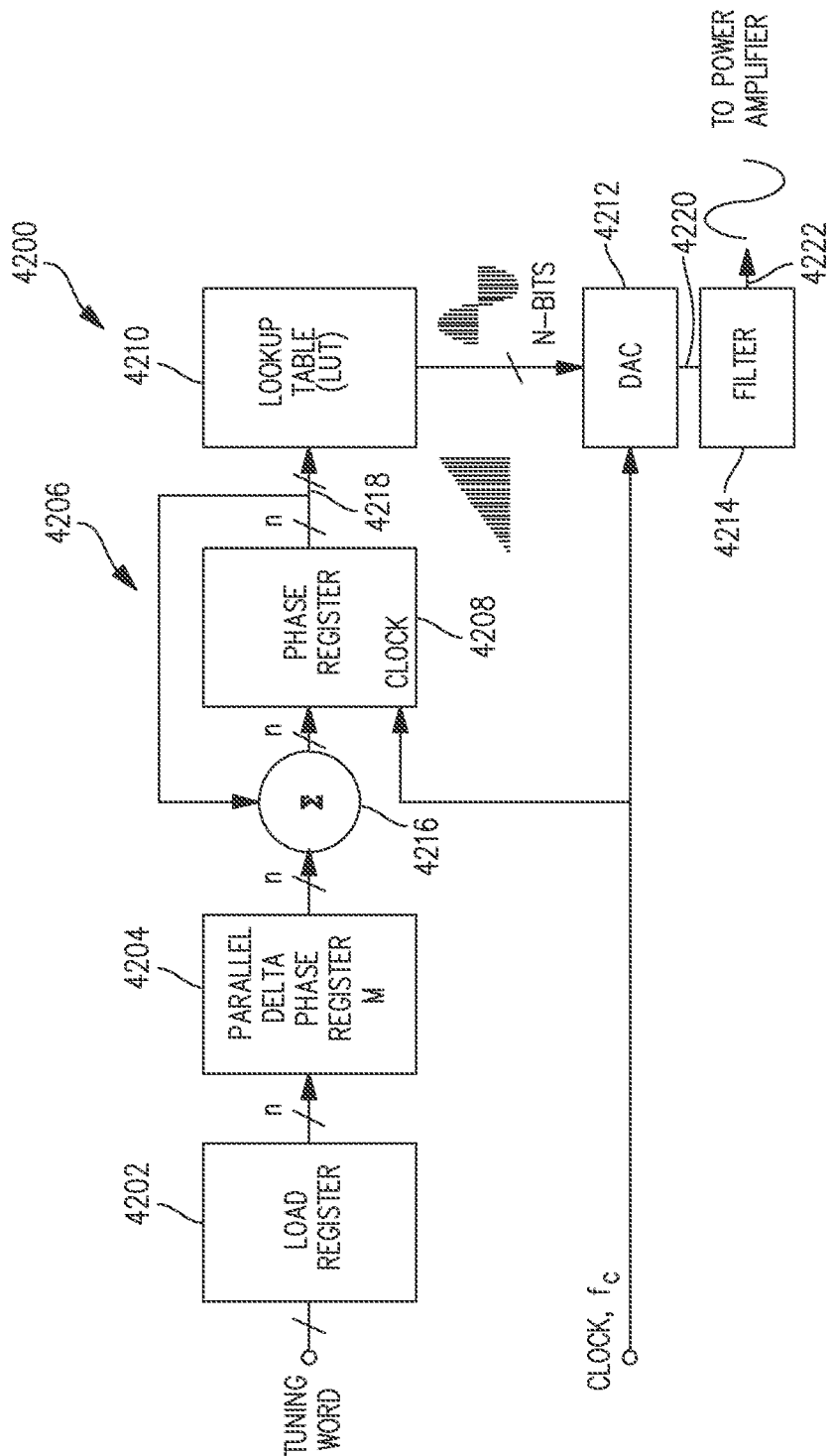
FIG. 14 illustrates one aspect of direct digital synthesis (DDS) circuit configured to generate a plurality of wave shapes for the electrical signal waveform for use in surgical instrument, in accordance with at least one aspect of the present disclosure.

A more flexible and efficient implementation of the DDS circuit 4100 employs a digital circuit called a Numerically Controlled Oscillator (NCO). A block diagram of a more flexible and efficient digital synthesis circuit such as a DDS circuit 4200 is shown in FIG. 14. In this simplified block diagram, a DDS circuit 4200 is coupled to a processor, controller, or a logic device of the generator and to a memory circuit located either in the generator or in any of the surgical instruments of surgical system 1000. The DDS circuit 4200 comprises a load register 4202, a parallel delta phase register 4204, an adder circuit 4216, a phase register 4208, a lookup table 4210 (phase-to-amplitude converter), a DAC circuit 4212, and a filter 4214. The adder circuit 4216 and the phase register 4208 form part of a phase accumulator 4206. A clock frequency $f_c$ is applied to the phase register 4208 and a DAC circuit 4212. The load register 4202 receives a tuning word that specifies output frequency as a fraction of the reference clock frequency signal $f_c$. The output of the load register 4202 is provided to the parallel delta phase register 4204 with a tuning word M.

The DDS circuit 4200 includes a sample clock that generates the clock frequency $f_c$, the phase accumulator 4206, and the lookup table 4210 (e.g., phase to amplitude converter). The content of the phase accumulator 4206 is updated once per clock cycle $f_c$. When time the phase accumulator 4206 is updated, the digital number, M, stored in the parallel delta phase register 4204 is added to the number in the phase register 4208 by the adder circuit 4216. Assuming that the number in the parallel delta phase register 4204 is 00 . . . 01 and that the initial contents of the phase accumulator 4206 is 00 . . . 00. The phase accumulator 4206 is updated by 00 . . . 01 per clock cycle. If the phase accumulator 4206 is 32-bits wide, 232 clock cycles (over 4 billion) are required before the phase accumulator 4206 returns to 00 . . . 00, and the cycle repeats.

A truncated output 4218 of the phase accumulator 4206 is provided to a phase-to amplitude converter lookup table 4210 and the output of the lookup table 4210 is coupled to a DAC circuit 4212. The truncated output 4218 of the phase accumulator 4206 serves as the address to a sine (or cosine) lookup table. An address in the lookup table corresponds to a phase point on the sinewave from 0° to 360°. The lookup table 4210 contains the corresponding digital amplitude information for one complete cycle of a sinewave. The lookup table 4210 therefore maps the phase information from the phase accumulator 4206 into a digital amplitude word, which in turn drives the DAC circuit 4212. The output of the DAC circuit is a first analog signal 4220 and is filtered by a filter 4214. The output of the filter 4214 is a second analog signal 4222, which is provided to a power amplifier coupled to the output of the generator circuit.

In one aspect, the electrical signal waveform may be digitized into 1024 ($2^{10}$) phase points, although the wave shape may be digitized is any suitable number of $2^n$ phase points ranging from 256 ($2^8$) to 281,474,976,710,656 ($2^{48}$), where n is a positive integer, as shown in TABLE 1. The electrical signal waveform may be expressed as $A_n(\theta_n)$, where a normalized amplitude $A_n$ at a point n is represented by a phase angle $\theta_n$ is referred to as a phase point at point n. The number of discrete phase points n determines the tuning resolution of the DDS circuit 4200 (as well as the DDS circuit 4100 shown in FIG. 13).

TABLE 1 specifies the electrical signal waveform digitized into a number of phase points.

TABLE 1

| N | Number of Phase Points $2^n$ |
|---|---|
| 8 | 256 |
| 10 | 1,024 |
| 12 | 4,096 |
| 14 | 16,384 |
| 16 | 65,536 |
| 18 | 262,144 |
| 20 | 1,048,576 |
| 22 | 4,194,304 |
| 24 | 16,777,216 |
| 26 | 67,108,864 |
| 28 | 268,435,456 |
| ... | ... |
| 32 | 4,294,967,296 |
| ... | ... |
| 48 | 281,474,976,710,656 |
| ... | ... |

The generator circuit algorithms and digital control circuits scan the addresses in the lookup table 4210, which in turn provides varying digital input values to the DAC circuit 4212 that feeds the filter 4214 and the power amplifier. The addresses may be scanned according to a frequency of interest. Using the lookup table enables generating various types of shapes that can be converted into an analog output signal by the DAC circuit 4212, filtered by the filter 4214, amplified by the power amplifier coupled to the output of the generator circuit, and fed to the tissue in the form of RF energy or fed to an ultrasonic transducer and applied to the tissue in the form of ultrasonic vibrations which deliver energy to the tissue in the form of heat. The output of the amplifier can be applied to an RF electrode, multiple RF electrodes simultaneously, an ultrasonic transducer, multiple ultrasonic transducers simultaneously, or a combination of RF and ultrasonic transducers, for example. Furthermore, multiple wave shape tables can be created, stored, and applied to tissue from a generator circuit.

With reference back to FIG. 13, for n=32, and M=1, the phase accumulator 4206 steps through $2^{32}$ possible outputs before it overflows and restarts. The corresponding output wave frequency is equal to the input clock frequency divided by $2^{32}$. If M=2, then the phase register 4106 "rolls over" twice as fast, and the output frequency is doubled. This can be generalized as follows.

For a phase accumulator 4206 configured to accumulate n-bits (n generally ranges from 24 to 32 in most DDS systems, but as previously discussed n may be selected from a wide range of options), there are $2^n$ possible phase points. The digital word in the delta phase register, M, represents the amount the phase accumulator is incremented per clock cycle. If $f_c$ is the clock frequency, then the frequency of the output sinewave is equal to:

$$f_0 = \frac{M \cdot f_c}{2^n}$$

The above equation is known as the DDS "tuning equation." Note that the frequency resolution of the system is equal to $$\frac{f_0}{2^n}.$$

For n=32, the resolution is greater than one part in four billion. In one aspect of the DDS circuit 4200, not all of the bits out of the phase accumulator 4206 are passed on to the lookup table 4210, but are truncated, leaving only the first 13 to 15 most significant bits (MSBs), for example. This reduces the size of the lookup table 4210 and does not affect the frequency resolution. The phase truncation only adds a small but acceptable amount of phase noise to the final output.

The electrical signal waveform may be characterized by a current, voltage, or power at a predetermined frequency. Further, where any one of the surgical instruments of surgical system 1000 comprises ultrasonic components, the electrical signal waveform may be configured to drive at least two vibration modes of an ultrasonic transducer of the at least one surgical instrument. Accordingly, the generator circuit may be configured to provide an electrical signal waveform to at least one surgical instrument wherein the electrical signal waveform is characterized by a predetermined wave shape stored in the lookup table 4210 (or lookup table 4104 FIG. 13). Further, the electrical signal waveform may be a combination of two or more wave shapes. The lookup table 4210 may comprise information associated with a plurality of wave shapes. In one aspect or example, the lookup table 4210 may be generated by the DDS circuit 4200 and may be referred to as a direct digital synthesis table. DDS works by first storing a large repetitive waveform in onboard memory. A cycle of a waveform (sine, triangle, square, arbitrary) can be represented by a predetermined number of phase points as shown in TABLE 1 and stored into memory. Once the waveform is stored into memory, it can be generated at very precise frequencies. The direct digital synthesis table may be stored in a non-volatile memory of the generator circuit and/or may be implemented with a FPGA circuit in the generator circuit. The lookup table 4210 may be addressed by any suitable technique that is convenient for categorizing wave shapes. According to one aspect, the lookup table 4210 is addressed according to a frequency of the electrical signal waveform. Additionally, the information associated with the plurality of wave shapes may be stored as digital information in a memory or as part of the lookup table 4210.

In one aspect, the generator circuit may be configured to provide electrical signal waveforms to at least two surgical instruments simultaneously. The generator circuit also may be configured to provide the electrical signal waveform, which may be characterized two or more wave shapes, via an output channel of the generator circuit to the two surgical instruments simultaneously. For example, in one aspect the electrical signal waveform comprises a first electrical signal to drive an ultrasonic transducer (e.g., ultrasonic drive signal), a second RF drive signal, and/or a combination thereof. In addition, an electrical signal waveform may comprise a plurality of ultrasonic drive signals, a plurality of RF drive signals, and/or a combination of a plurality of ultrasonic and RF drive signals.

In addition, a method of operating the generator circuit according to the present disclosure comprises generating an electrical signal waveform and providing the generated electrical signal waveform to any one of the surgical instruments of surgical system 1000, where generating the electrical signal waveform comprises receiving information associated with the electrical signal waveform from a memory. The generated electrical signal waveform comprises at least one wave shape. Furthermore, providing the generated electrical signal waveform to the at least one surgical instrument comprises providing the electrical signal waveform to at least two surgical instruments simultaneously.

The generator circuit as described herein may allow for the generation of various types of direct digital synthesis tables. Examples of wave shapes for RF/Electrosurgery signals suitable for treating a variety of tissue generated by the generator circuit include RF signals with a high crest factor (which may be used for surface coagulation in RF mode), a low crest factor RF signals (which may be used for deeper tissue penetration), and waveforms that promote efficient touch-up coagulation. The generator circuit also may generate multiple wave shapes employing a direct digital synthesis lookup table 4210 and, on the fly, can switch between particular wave shapes based on the desired tissue effect. Switching may be based on tissue impedance and/or other factors.

In addition to traditional sine/cosine wave shapes, the generator circuit may be configured to generate wave shape(s) that maximize the power into tissue per cycle (i.e., trapezoidal or square wave). The generator circuit may provide wave shape(s) that are synchronized to maximize the power delivered to the load when driving RF and ultrasonic signals simultaneously and to maintain ultrasonic frequency lock, provided that the generator circuit includes a circuit topology that enables simultaneously driving RF and ultrasonic signals. Further, custom wave shapes specific to instruments and their tissue effects can be stored in a non-volatile memory (NVM) or an instrument EEPROM and can be fetched upon connecting any one of the surgical instruments of surgical system 1000 to the generator circuit.

The DDS circuit 4200 may comprise multiple lookup tables 4104 where the lookup table 4210 stores a waveform represented by a predetermined number of phase points (also may be referred to as samples), wherein the phase points define a predetermined shape of the waveform. Thus multiple waveforms having a unique shape can be stored in multiple lookup tables 4210 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 4200 can create multiple wave shape lookup tables 4210 and during a tissue treatment procedure (e.g., "on-the-fly" or in virtual real time based on user or sensor inputs) switch between different wave shapes stored in different lookup tables 4210 based on the tissue effect desired and/or tissue feedback. Accordingly, switching between wave shapes can be based on tissue impedance and other factors, for example. In other aspects, the lookup tables 4210 can store electrical signal waveforms shaped to maximize the power delivered into the tissue per cycle (i.e., trapezoidal or square wave). In other aspects, the lookup tables 4210 can store wave shapes synchronized in such way that they make maximizing power delivery by any one of the surgical instruments of surgical system 1000 when delivering RF and ultrasonic drive signals. In yet other aspects, the lookup tables 4210 can store electrical signal waveforms to drive ultrasonic and RF therapeutic, and/or sub-therapeutic, energy simultaneously while maintaining ultrasonic frequency lock. Generally, the output wave shape may be in the form of a sine wave, cosine wave, pulse wave, square wave, and the like. Nevertheless, the more complex and custom wave shapes specific to different instruments and their tissue effects can be stored in the non-volatile memory of the generator circuit or in the non-volatile memory (e.g., EEPROM) of the surgical instrument and be fetched upon connecting the surgical instrument to the generator circuit. One example of a custom wave shape is an exponentially damped sinusoid as used in many high crest factor "coagulation" waveforms, as shown in FIG. 43.

FIG. 15 illustrates one cycle of a discrete time digital electrical signal waveform 4300, in accordance with at least one aspect of the present disclosure of an analog waveform 4304 (shown superimposed over the discrete time digital electrical signal waveform 4300 for comparison purposes). The horizontal axis represents Time (t) and the vertical axis represents digital phase points. The digital electrical signal waveform 4300 is a digital discrete time version of the desired analog waveform 4304, for example. The digital electrical signal waveform 4300 is generated by storing an amplitude phase point 4302 that represents the amplitude per clock cycle $T_{clk}$ over one cycle or period $T_o$. The digital electrical signal waveform 4300 is generated over one period $T_o$ by any suitable digital processing circuit. The amplitude phase points are digital words stored in a memory circuit. In the example illustrated in FIGS. 13, 14, the digital word is a six-bit word that is capable of storing the amplitude phase points with a resolution of 26 or 64 bits. It will be appreciated that the examples shown in FIGS. 13, 14 is for illustrative purposes and in actual implementations the resolution can be much higher. The digital amplitude phase points 4302 over one cycle $T_o$ are stored in the memory as a string of string words in a lookup table 4104, 4210 as described in connection with FIGS. 13, 14, for example. To generate the analog version of the analog waveform 4304, the amplitude phase points 4302 are read sequentially from the memory from 0 to $T_o$ per clock cycle $T_{clk}$ and are converted by a DAC circuit 4108, 4212, also described in connection with FIGS. 13, 14. Additional cycles can be generated by repeatedly reading the amplitude phase points 4302 of the digital electrical signal waveform 4300 the from 0 to $T_o$ for as many cycles or periods as may be desired. The smooth analog version of the analog waveform 4304 is achieved by filtering the output of the DAC circuit 4108, 4212 by a filter 4112, 4214 (FIGS. 13 and 14). The filtered analog output signal 4114, 4222 (FIGS. 13 and 14) is applied to the input of a power amplifier.

Figure 16:
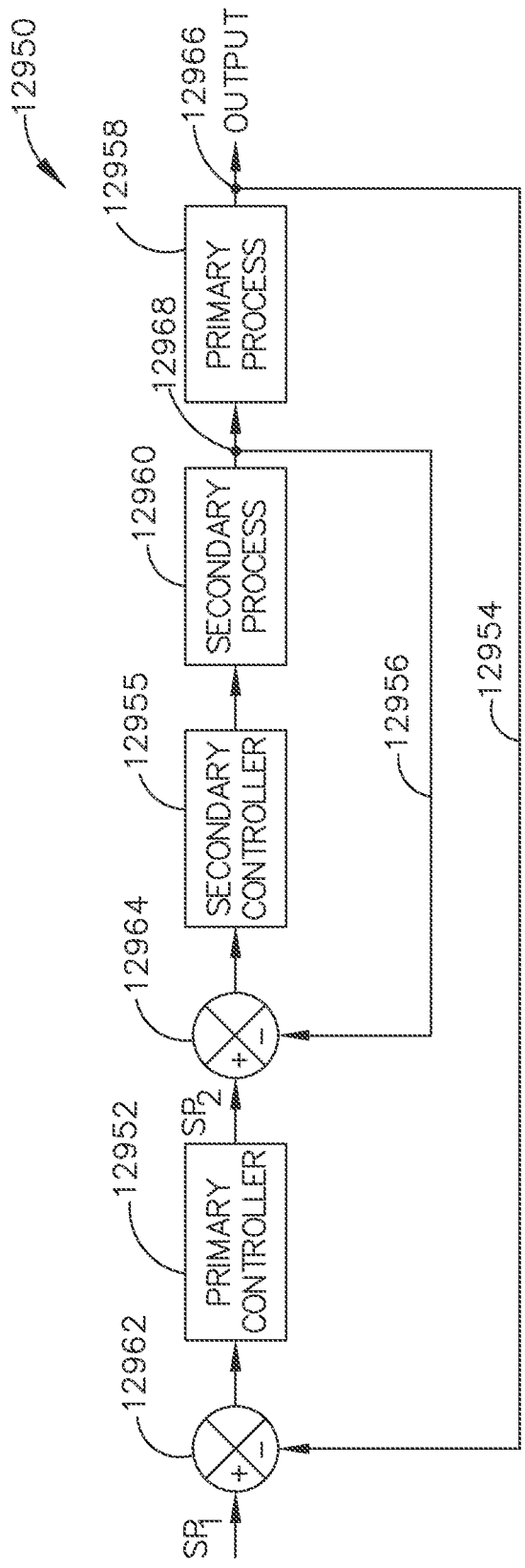
FIG. 16 is a diagram of a control system in accordance with one aspect of this disclosure.
Figure 17:
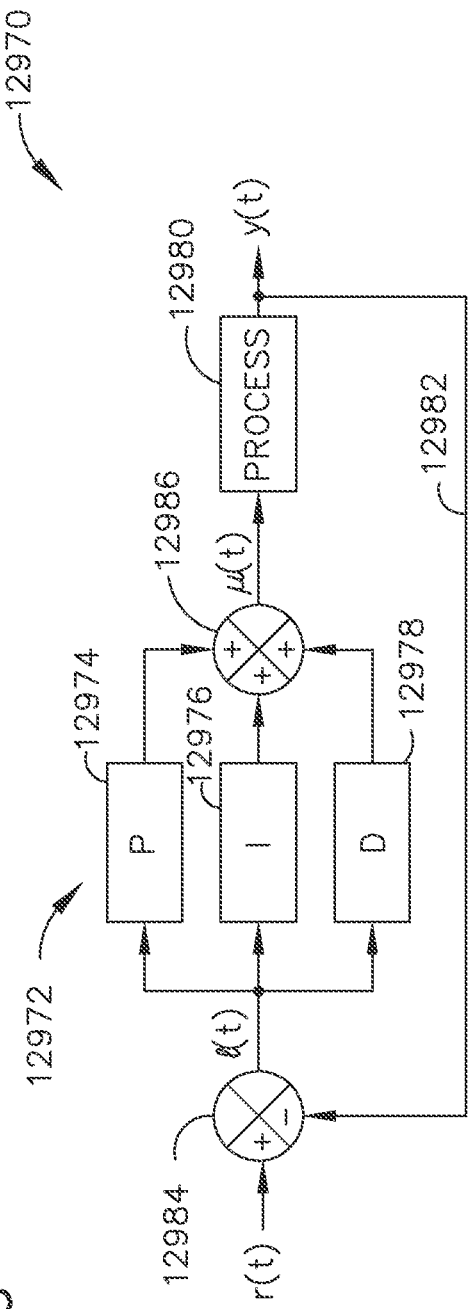
FIG. 17 illustrates a proportional-integral-derivative (PID) controller feedback control system in accordance with one aspect of this disclosure.

FIG. 16 is a diagram of a control system 12950 that may be implemented as a nested PID feedback controller. A PID controller is a control loop feedback mechanism (controller) to continuously calculate an error value as the difference between a desired set point and a measured process variable and applies a correction based on proportional, integral, and derivative terms (sometimes denoted P, I, and D respectively). The nested PID controller feedback control system 12950 includes a primary controller 12952, in a primary (outer) feedback loop 12954 and a secondary controller 12955 in a secondary (inner) feedback loop 12956. The primary controller 12952 may be a PID controller 12972 as shown in FIG. 17, and the secondary controller 12955 also may be a PID controller 12972 as shown in FIG. 17. The primary controller 12952 controls a primary process 12958 and the secondary controller 12955 controls a secondary process 12960. The output 12966 of the primary process 12958 is subtracted from a primary set point $SP_1$ by a first summer 12962. The first summer 12962 produces a single sum output signal which is applied to the primary controller 12952. The output of the primary controller 12952 is the secondary set point $SP_2$. The output 12968 of the secondary process 12960 is subtracted from the secondary set point $SP_2$ by a second summer 12964.

FIG. 17 illustrates a PID feedback control system 12970 according to one aspect of this disclosure. The primary controller 12952 or the secondary controller 12955, or both, may be implemented as a PID controller 12972. In one aspect, the PID controller 12972 may comprise a proportional element 12974 (P), an integral element 12976 (I), and a derivative element 12978 (D). The outputs of the P, I, D elements 12974, 12976, 12978 are summed by a summer 12986, which provides the control variable μ(t) to the process 12980. The output of the process 12980 is the process variable y(t). A summer 12984 calculates the difference between a desired set point r(t) and a measured process variable y(t) received by feedback loop 12982. The PID controller 12972 continuously calculates an error value e(t) (e.g., difference between closure force threshold and measured closure force) as the difference between a desired set point r(t) (e.g., closure force threshold) and a measured process variable y(t) (e.g., velocity and direction of closure tube) and applies a correction based on the proportional, integral, and derivative terms calculated by the proportional element 12974 (P), integral element 12976 (I), and derivative element 12978 (D), respectively. The PID controller 12972 attempts to minimize the error e(t) over time by adjustment of the control variable p(t) (e.g., velocity and direction of the closure tube).

In accordance with the PID algorithm, the "P" element 12974 accounts for present values of the error. For example, if the error is large and positive, the control output will also be large and positive. In accordance with the present disclosure, the error term e(t) is the difference between the desired closure force and the measured closure force of the closure tube. The "I" element 12976 accounts for past values of the error. For example, if the current output is not sufficiently strong, the integral of the error will accumulate over time, and the controller will respond by applying a stronger action. The "D" element 12978 accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot.

It will be appreciated that other variables and set points may be monitored and controlled in accordance with the feedback control systems 12950, 12970. For example, the adaptive closure member velocity control algorithm described herein may measure at least two of the following parameters: firing member stroke location, firing member load, displacement of cutting element, velocity of cutting element, closure tube stroke location, closure tube load, among others.

Figure 18:
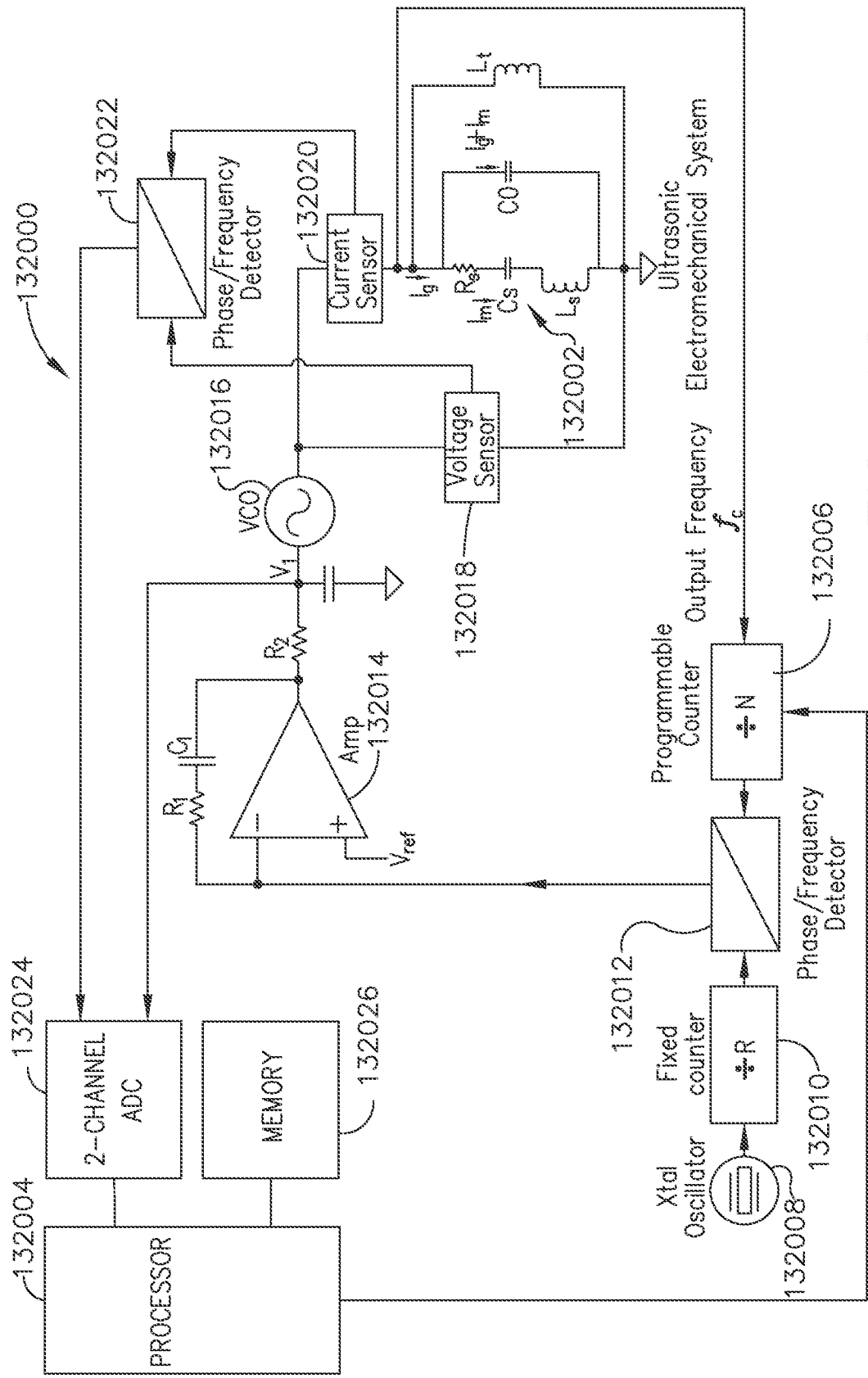
FIG. 18 is an alternative system for controlling the frequency of an ultrasonic electromechanical system and detecting the impedance thereof, in accordance with at least one aspect of the present disclosure.

FIG. 18 is an alternative system 132000 for controlling the frequency of an ultrasonic electromechanical system 132002 and detecting the impedance thereof, in accordance with at least one aspect of the present disclosure. The system 132000 may be incorporated into a generator. A processor 132004 coupled to a memory 132026 programs a programmable counter 132006 to tune to the output frequency $f_o$ of the ultrasonic electromechanical system 132002. The input frequency is generated by a crystal oscillator 132008 and is input into a fixed counter 132010 to scale the frequency to a suitable value. The outputs of the fixed counter 132010 and the programmable counter 132006 are applied to a phase/frequency detector 132012. The output of the phase/frequency detector 132012 is applied to an amplifier/active filter circuit 132014 to generate a tuning voltage $V_t$ that is applied to a voltage controlled oscillator 132016 (VCO). The VCO 132016 applies the output frequency $f_o$ to an ultrasonic transducer portion of the ultrasonic electromechanical system 132002, shown here modeled as an equivalent electrical circuit. The voltage and current signals applied to the ultrasonic transducer are monitored by a voltage sensor 132018 and a current sensor 132020.

The outputs of the voltage and current sensors 132018, 132020 are applied to another phase/frequency detector 132022 to determine the phase angle between the voltage and current as measured by the voltage and current sensors 132018, 132020. The output of the phase/frequency detector 132022 is applied to one channel of a high speed analog to digital converter 132024 (ADC) and is provided to the processor 132004 therethrough. Optionally, the outputs of the voltage and current sensors 132018, 132020 may be applied to respective channels of the two-channel ADC 132024 and provided to the processor 132004 for zero crossing, FFT, or other algorithm described herein for determining the phase angle between the voltage and current signals applied to the ultrasonic electromechanical system 132002.

Optionally the tuning voltage $V_t$, which is proportional to the output frequency $f_o$, may be fed back to the processor 132004 via the ADC 132024. This provides the processor 132004 with a feedback signal proportional to the output frequency $f_o$, and can use this feedback to adjust and control the output frequency $f_o$.

Estimating the State of the Jaw (Pad Burn Through, Staples, Broken Blade, Bone in Jaw, Tissue in Jaw)

A challenge with ultrasonic energy delivery is that ultrasonic acoustics applied on the wrong materials or the wrong tissue can result in device failure, for example, clamp arm pad burn through or ultrasonic blade breakage. It is also desirable to detect what is located in the jaws of an end effector of an ultrasonic device and the state of the jaws without adding additional sensors in the jaws. Locating sensors in the jaws of an ultrasonic end effector poses reliability, cost, and complexity challenges.

Ultrasonic spectroscopy smart blade algorithm techniques may be employed for estimating the state of the jaw (clamp arm pad burn through, staples, broken blade, bone in jaw, tissue in jaw, back-cutting with jaw closed, etc.) based on the impedance $$Z_g(t) = \frac{V_g(t)}{I_g(t)}$$

of an ultrasonic transducer configured to drive an ultrasonic transducer blade, in accordance with at least one aspect of the present disclosure. The impedance $Z_g(t)$, magnitude $|Z|$, and phase $\varphi$ are plotted as a function of frequency f.

Dynamic mechanical analysis (DMA), also known as dynamic mechanical spectroscopy or simply mechanical spectroscopy, is a technique used to study and characterize materials. A sinusoidal stress is applied to a material, and the strain in the material is measured, allowing the determination of the complex modulus of the material. The spectroscopy as applied to ultrasonic devices includes exciting the tip of the ultrasonic blade with a sweep of frequencies (compound signals or traditional frequency sweeps) and measuring the resulting complex impedance at each frequency. The complex impedance measurements of the ultrasonic transducer across a range of frequencies are used in a classifier or model to infer the characteristics of the ultrasonic end effector. In one aspect, the present disclosure provides a technique for determining the state of an ultrasonic end effector (clamp arm, jaw) to drive automation in the ultrasonic device (such as disabling power to protect the device, executing adaptive algorithms, retrieving information, identifying tissue, etc.).

Figure 19:
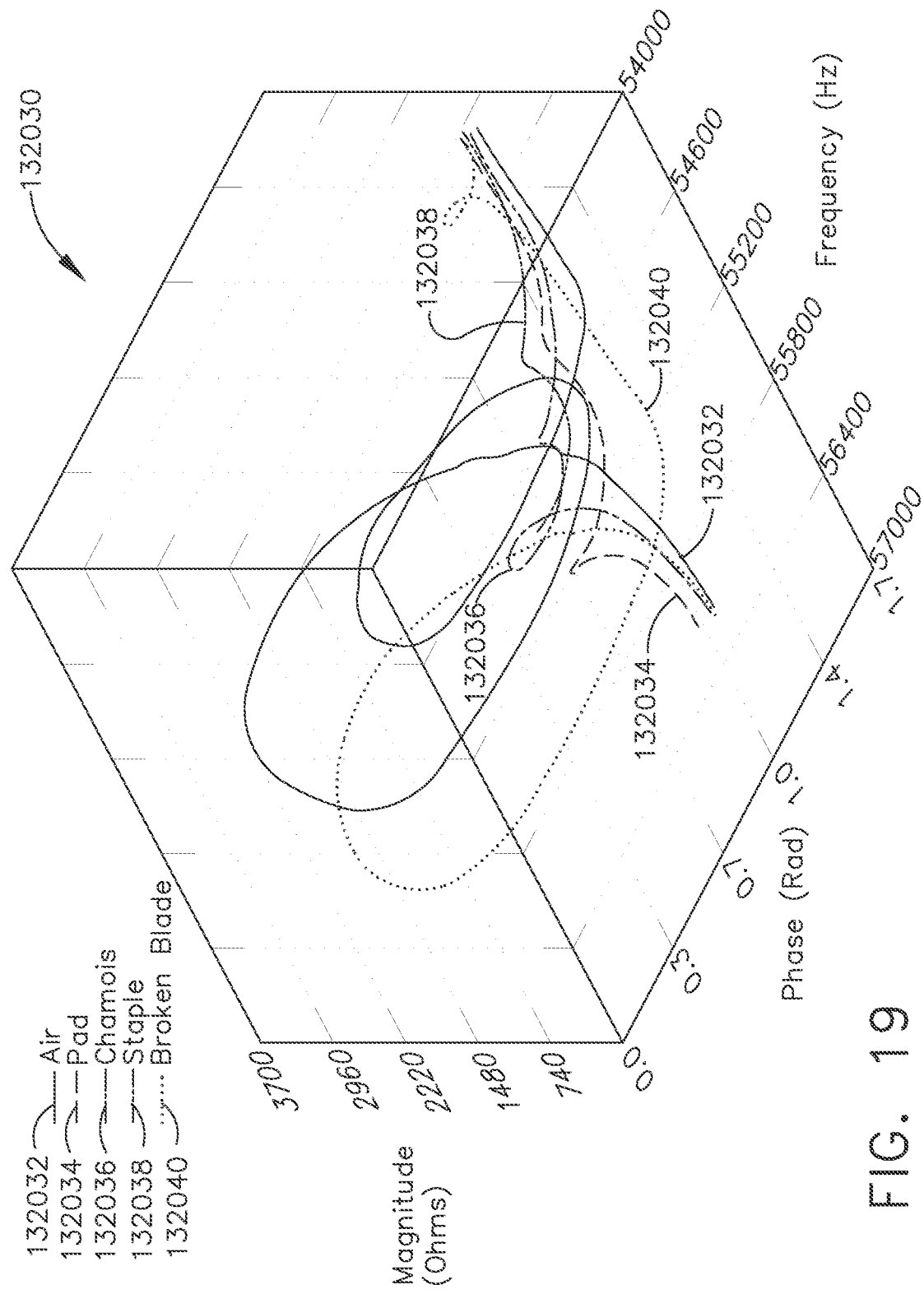
FIG. 19 is a spectra of the same ultrasonic device with a variety of different states and conditions of the end effector where phase and magnitude of the impedance of an ultrasonic transducer are plotted as a function of frequency, in accordance with at least one aspect of the present disclosure.

FIG. 19 is a spectra 132030 of an ultrasonic device with a variety of different states and conditions of the end effector where the impedance $Z_g(t)$, magnitude $|Z|$, and phase $\varphi$ are plotted as a function of frequency f, in accordance with at least one aspect of the present disclosure. The spectra 132030 is plotted in three-dimensional space where frequency (Hz) is plotted along the x-axis, phase (Rad) is plotted along the y-axis, and magnitude (Ohms) is plotted along the z-axis.

Spectral analysis of different jaw bites and device states produces different complex impedance characteristic patterns (fingerprints) across a range of frequencies for different conditions and states. Each state or condition has a different characteristic pattern in 3D space when plotted. These characteristic patterns can be used to estimate the condition and state of the end effector. FIG. 19 shows the spectra for air 132032, clamp arm pad 132034, chamois 132036, staple 132038, and broken blade 132040. The chamois 132036 may be used to characterize different types of tissue.

The spectra 132030 can be evaluated by applying a low-power electrical signal across the ultrasonic transducer to produce a non-therapeutic excitation of the ultrasonic blade. The low-power electrical signal can be applied in the form of a sweep or a compound Fourier series to measure the impedance $$Z_g(t) = \frac{V_g(t)}{I_g(t)}$$

across the ultrasonic transducer at a range of frequencies in series (sweep) or in parallel (compound signal) using an FFT.

Methods of Classification of New Data

For each characteristic pattern, a parametric line can be fit to the data used for training using a polynomial, a Fourier series, or any other form of parametric equation as may be dictated by convenience. A new data point is then received and is classified by using the Euclidean perpendicular distance from the new data point to the trajectory that has been fitted to the characteristic pattern training data. The perpendicular distance of the new data point to each of the trajectories (each trajectory representing a different state or condition) is used to assign the point to a state or condition.

The probability distribution of distance of each point in the training data to the fitted curve can be used to estimate the probability of a correctly classified new data point. This essentially constructs a two-dimensional probability distribution in a plane perpendicular to the fitted trajectory at each new data point of the fitted trajectory. The new data point can then be included in the training set based on its probability of correct classification to make an adaptive, learning classifier that readily detects high-frequency changes in states but adapts to slow occurring deviations in system performance, such as a device getting dirty or the pad wearing out.

Figure 20:
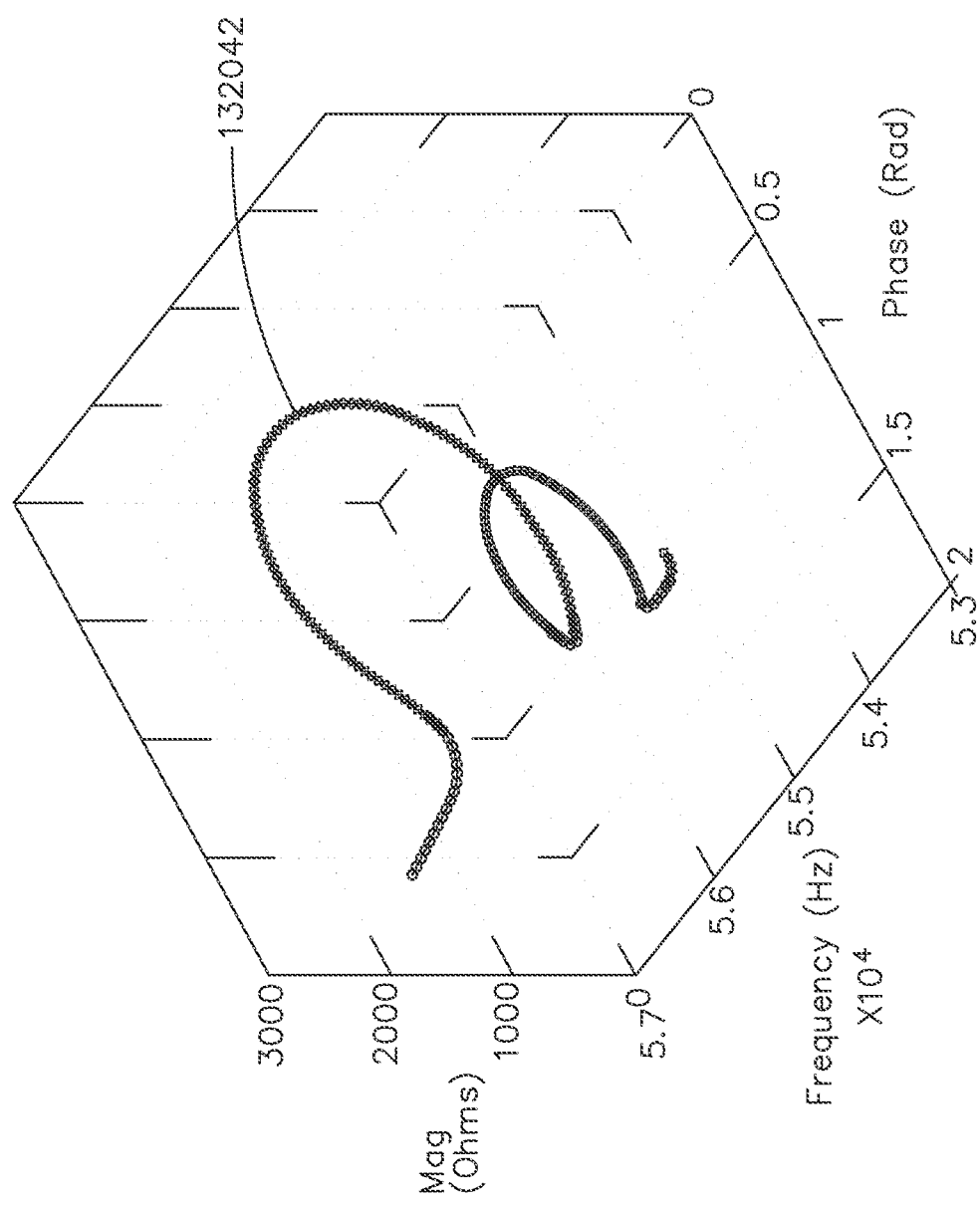
FIG. 20 is a graphical representation of a plot of a set of 3D training data S, where ultrasonic transducer impedance magnitude and phase are plotted as a function of frequency, in accordance with at least one aspect of the present disclosure.

FIG. 20 is a graphical representation of a plot 132042 of a set of 3D training data set (S), where ultrasonic transducer impedance $Z_g(t)$, magnitude $|Z|$, and phase $\varphi$ are plotted as a function of frequency f, in accordance with at least one aspect of the present disclosure. The 3D training data set (S) plot 132042 is graphically depicted in three-dimensional space where phase (Rad) is plotted along the x-axis, frequency (Hz) is plotted along the y-axis, magnitude (Ohms) is plotted along the z-axis, and a parametric Fourier series is fit to the 3D training data set (S). A methodology for classifying data is based on the 3D training data set (S0 is used to generate the plot 132042).

The parametric Fourier series fit to the 3D training data set (S) is defined by:

$$\vec{p} = \vec{a}_0 + \sum_{n=1}^{\infty} \left( \vec{a}_n \cos \frac{n\pi t}{L} + \vec{b}_n \sin \frac{n\pi t}{L} \right)$$

For a new point $\vec{z}$ the perpendicular distance from $\vec{p}$ to $\vec{z}$ is found by:

$$D = \|\vec{p} - \vec{z}\|$$

When:

$$\frac{\partial D}{\partial T} = 0$$

Then:

$$D = D_\perp$$

A probability distribution of D can be used to estimate the probability of a data point $\vec{z}$ belonging to the group S.

Control

Based on the classification of data measured before, during, or after activation of the ultrasonic transducer/ultrasonic blade, a variety of automated tasks and safety measures can be implemented. Similarly, the state of the tissue located in the end effector and temperature of the ultrasonic blade also can be inferred to some degree, and used to better inform the user of the state of the ultrasonic device or protect critical structures, etc. Temperature control of an ultrasonic blade is described in commonly owned U.S. Provisional Patent Application No. 62/640,417, filed Mar. 8, 2018, titled TEMPERATURE CONTROL IN ULTRASONIC DEVICE AND CONTROL SYSTEM THEREFOR, which is incorporated herein by reference in its entirety.

Similarly, power delivery can be reduced when there is a high probability that the ultrasonic blade is contacting the clamp arm pad (e.g., without tissue in between) or if there is a probability that the ultrasonic blade has broken or that the ultrasonic blade is touching metal (e.g., a staple). Furthermore, back-cutting can be disallowed if the jaw is closed and no tissue is detected between the ultrasonic blade and the clamp arm pad.

Integration of Other Data to Improve Classification

This system can be used in conjunction with other information provided by sensors, the user, metrics on the patient, environmental factors, etc., by combing the data from this process with the aforementioned data using probability functions and a Kalman filter. The Kalman filter determines the maximum likelihood of a state or condition occurring given a plethora of uncertain measurements of varying confidence. Since this method allows for an assignment of probability to a newly classified data point, this algorithm's information can be implemented with other measures or estimates in a Kalman filter.

Figure 21:
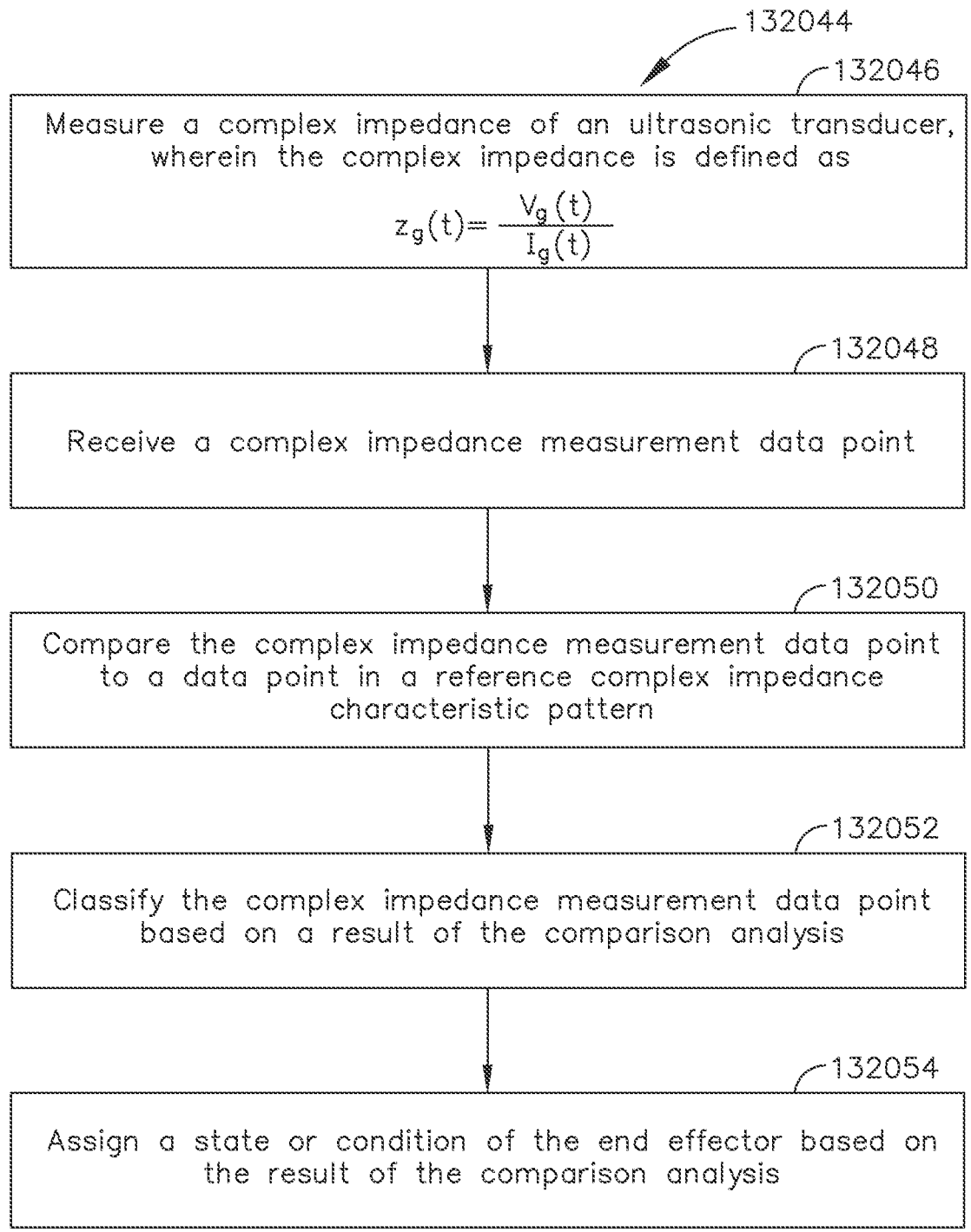
FIG. 21 is a logic flow diagram depicting a control program or a logic configuration to determine jaw conditions based on the complex impedance characteristic pattern (fingerprint), in accordance with at least one aspect of the present disclosure.

FIG. 21 is a logic flow diagram 132044 depicting a control program or a logic configuration to determine jaw conditions based on the complex impedance characteristic pattern (fingerprint), in accordance with at least one aspect of the present disclosure. Prior to determining jaw conditions based on the complex impedance characteristic pattern (fingerprint), a database is populated with reference complex impedance characteristic patterns or a training data sets (S) that characterize various jaw conditions, including, without limitation, air 132032, clamp arm pad 132034, chamois 132036, staple 132038, broken blade 132040, as shown in FIG. 82, and a variety of tissue types and conditions. The chamois dry or wet, full byte or tip, may be used to characterize different types of tissue. The data points used to generate reference complex impedance characteristic patterns or a training data set (S) are obtained by applying a sub-therapeutic drive signal to the ultrasonic transducer, sweeping the driving frequency over a predetermined range of frequencies from below resonance to above resonance, measuring the complex impedance at each of the frequencies, and recording the data points. The data points are then fit to a curve using a variety of numerical methods including polynomial curve fit, Fourier series, and/or parametric equation. A parametric Fourier series fit to the reference complex impedance characteristic patterns or a training data set (S) is described herein.

Once the reference complex impedance characteristic patterns or a training data sets (S) are generated, the ultrasonic instrument measures new data points, classifies the new points, and determines whether the new data points should be added to the reference complex impedance characteristic patterns or a training data sets (S).

Turning now to the logic flow diagram of FIG. 21, in one aspect, the control circuit measures 132046 a complex impedance of an ultrasonic transducer, wherein the complex impedance is defined as $$Z_g(t) = \frac{V_g(t)}{I_g(t)}.$$

The control circuit receives 132048 a complex impedance measurement data point and compares 132050 the complex impedance measurement data point to a data point in a reference complex impedance characteristic pattern. The control circuit classifies 132052 the complex impedance measurement data point based on a result of the comparison analysis and assigns 132054 a state or condition of the end effector based on the result of the comparison analysis.

In one aspect, the control circuit receives the reference complex impedance characteristic pattern from a database or memory coupled to the processor. In one aspect, the control circuit generates the reference complex impedance characteristic pattern as follows. A drive circuit coupled to the control circuit applies a nontherapeutic drive signal to the ultrasonic transducer starting at an initial frequency, ending at a final frequency, and at a plurality of frequencies therebetween. The control circuit measures the impedance of the ultrasonic transducer at each frequency and stores a data point corresponding to each impedance measurement. The control circuit curve fits a plurality of data points to generate a three-dimensional curve of representative of the reference complex impedance characteristic pattern, wherein the magnitude $|Z|$ and phase $\varphi$ are plotted as a function of frequency f. The curve fitting includes a polynomial curve fit, a Fourier series, and/or a parametric equation.

In one aspect, the control circuit receives a new impedance measurement data point and classifies the new impedance measurement data point using a Euclidean perpendicular distance from the new impedance measurement data point to a trajectory that has been fitted to the reference complex impedance characteristic pattern. The control circuit estimates a probability that the new impedance measurement data point is correctly classified. The control circuit adds the new impedance measurement data point to the reference complex impedance characteristic pattern based on the probability of the estimated correct classification of the new impedance measurement data point. In one aspect, the control circuit classifies data based on a training data set (S), where the training data set (S) comprises a plurality of complex impedance measurement data, and curve fits the training data set (S) using a parametric Fourier series, wherein S is defined herein and wherein the probability distribution is used to estimate the probability of the new impedance measurement data point belonging to the group S.

State of Jaw Classifier Based on Model

There has been an existing interest in classifying matter located within the jaws of an ultrasonic device including tissue types and condition. In various aspects, it can be shown that with high data sampling and sophisticated pattern recognition this classification is possible. The approach is based on impedance as a function of frequency, where magnitude, phase, and frequency are plotted in 3D the patterns look like ribbons as shown in FIGS. 19 and 20 and the logic flow diagram of FIG. 21. This disclosure provides an alternative smart blade algorithm approach that is based on a well-established model for piezoelectric transducers.

Figure 22:
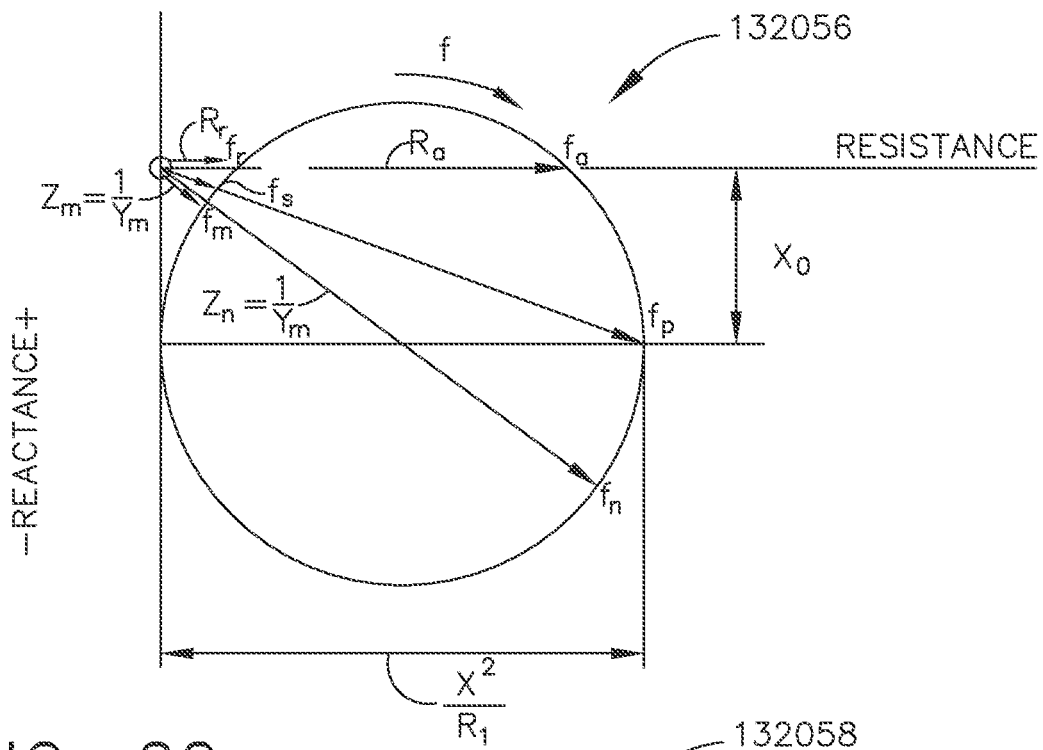
FIG. 22 is a circle plot of complex impedance plotted as an imaginary component versus real components of a piezoelectric vibrator, in accordance with at least one aspect of the present disclosure.
Figure 23:
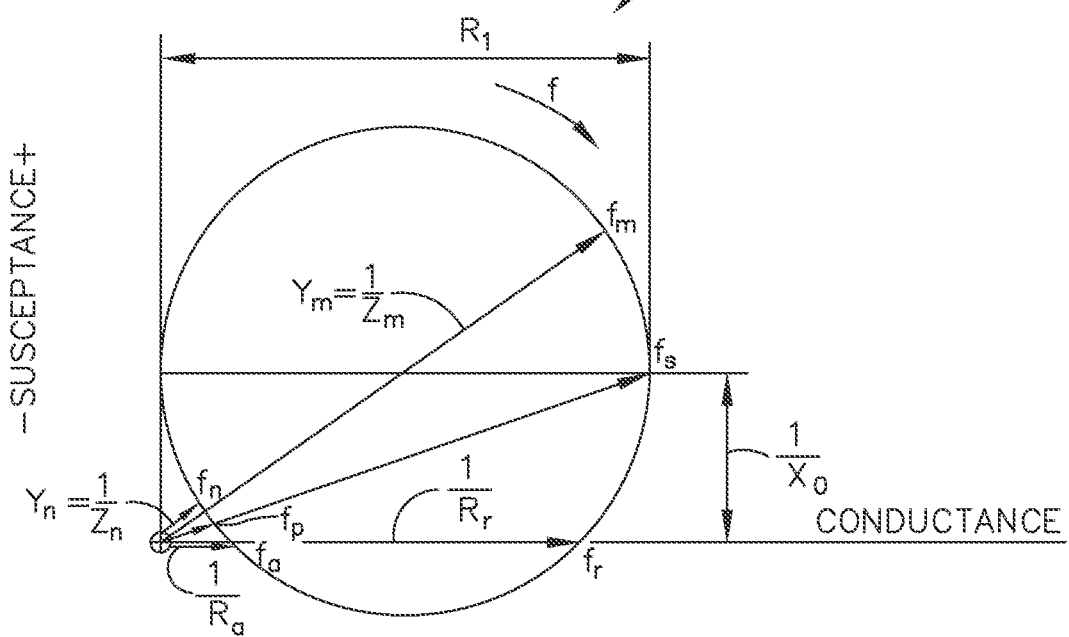
FIG. 23 is a circle plot of complex admittance plotted as an imaginary component versus real components of a piezoelectric vibrator, in accordance with at least one aspect of the present disclosure.

By way of example, the equivalent electrical lumped parameter model is known to be an accurate model of the physical piezoelectric transducer. It is based on the Mittag- Leffler expansion of a tangent near a mechanical resonance. When the complex impedance or the complex admittance is plotted as an imaginary component versus a real component, circles are formed. FIG. 22 is a circle plot 132056 of complex impedance plotted as an imaginary component versus real components of a piezoelectric vibrator, in accordance with at least one aspect of the present disclosure. FIG. 23 is a circle plot 132058 of complex admittance plotted as an imaginary component versus real components of a piezoelectric vibrator, in accordance with at least one aspect of the present disclosure. The circles depicted in FIGS. 22 and 23 are taken from the IEEE 177 Standard, which is incorporated herein by reference in its entirety. Tables 1-4 are taken from the IEEE 177 Standard and disclosed herein for completeness.

The circle is created as the frequency is swept from below resonance to above resonance. Rather than stretching the circle out in 3D, a circle is identified and the radius (r) and offsets (a, b) of the circle are estimated. These values are then compared with established values for given conditions. These conditions may be: 1) open nothing in jaws, 2) tip bite 3) full bite and staple in jaws. If the sweep generates multiple resonances, circles of different characteristics will be present for each resonance. Each circle will be drawn out before the next if the resonances are separated. Rather than fitting a 3D curve with a series approximation, the data is fitted with a circle. The radius (r) and offsets (a, b) can be calculated using a processor programmed to execute a variety of mathematical or numerical techniques described below. These values may be estimated by capturing an image of a circle and, using image processing techniques, the radius (r) and offsets (a, b) that define the circle are estimated.

Figure 24:
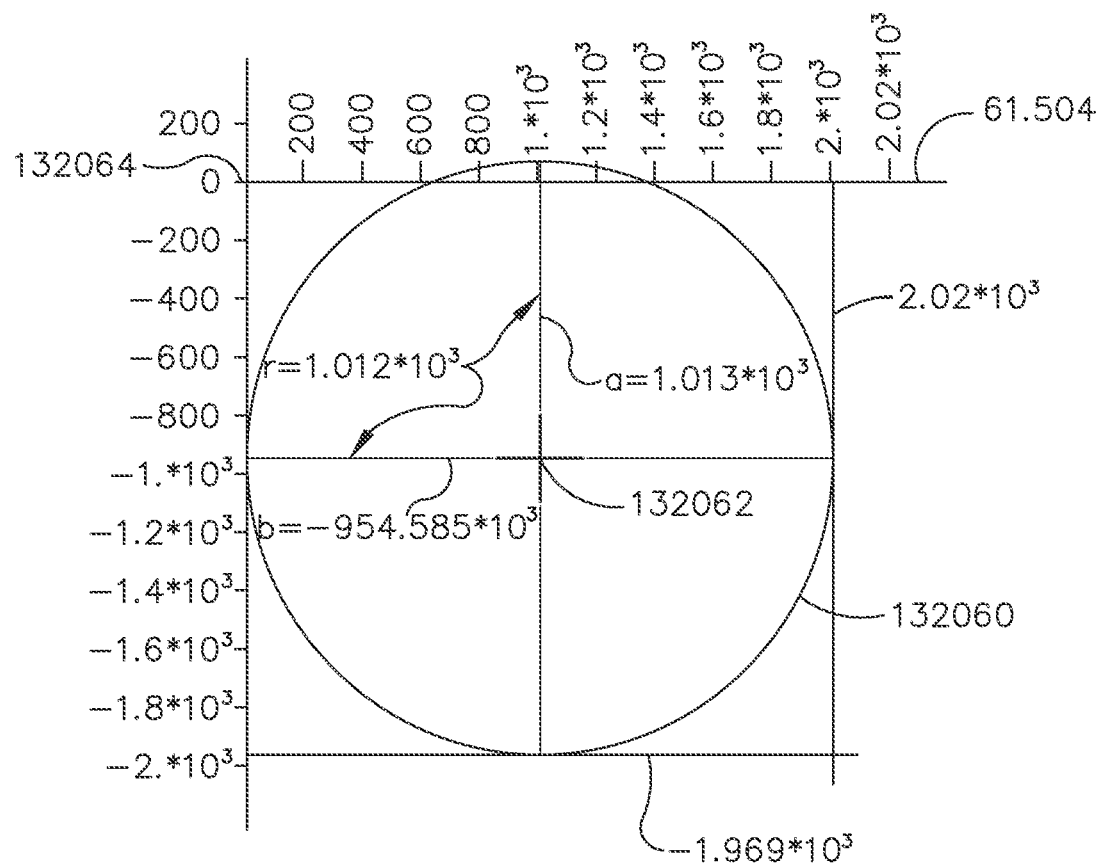
FIG. 24 is a circle plot of complex admittance for a 55.5 kHz ultrasonic piezoelectric transducer.

FIG. 24 is a circle plot 132060 of complex admittance for a 55.5 kHz ultrasonic piezoelectric transducer for lumped parameters inputs and outputs specified hereinbelow. Values for a lumped parameter model were used to generate the complex admittance. A moderate load was applied in the model. The obtained admittance circle generated in Math-Cad is shown in FIG. 24. The circle plot 132060 is formed when the frequency is swept from 54 to 58 kHz.

The lumped parameter input values are:

Co=3.0 nF

Cs=8.22 pF

Ls=1.0 H

Rs=450Ω

The outputs of the model based on the inputs are:

$$am = \frac{D \cdot C - B \cdot C}{A \cdot C - B^2} = 1.013 \cdot 10^3$$

$$bm = \frac{A \cdot E - B \cdot D}{A \cdot C - B^2} = -954.585$$

$$rm = \frac{1}{fpts}\left(\sum_i^{fpts} \sqrt[2]{((Zout_{1,i} = am)^2 + (Zout_{2,i} - bm)^2)}\right) = 1.012 \cdot 10^3$$

The output values are used to plot the circle plot 132060 shown in FIG. 24. The circle plot 132060 has a radius (r) and the center 132062 is offset (a, b) from the origin 132064 as follows:

$r=1.012*10^3$ $a=1.013*10^3$ $b=954.585$

The summations A-E specified below are needed to estimate the circle plot 132060 plot for the example given in FIG. 24, in accordance with at least one aspect of the present disclosure. Several algorithms exist to calculate a fit to a circle. A circle is defined by its radius (r) and offsets (a, b) of the center from the origin:

$$r^2 = (x-a)^2 + (y-b)^2$$

The modified least squares method (Umbach and Jones) is convenient in that there a simple close formed solution for a, b, and r.

$$\hat{a} = \frac{DC - BE}{AC - B^2}$$

$$\hat{b} = \frac{AE - BD}{AC - B^2}$$

$$\hat{r} = \frac{1}{n}\sum_{i=1}^{n}\sqrt{(x_i - \hat{a})^2 + (y_i - \hat{b})^2}$$

The caret symbol over the variable "a" indicates an estimate of the true value. A, B, C, D, and E are summations of various products which are calculated from the data. They are included herein for completeness as follows:

$$A := fpts \cdot \sum_i^{fpts} (Zout_{1,i})^2 - \left(\sum_i^{fpts}(Zout_{1,i})\right)^2 = 5.463 \cdot 10^{10}$$

$$B := fpts\sum_i^{fpts}(Zout_{1,i} \cdot Zout_{2,i}) - \left(\left(\sum_i^{fpts}(Zout_{1,i})\right) \cdot \left(\sum_i^{fpts}(Zout_{2,i})\right)\right) = 5.461 \cdot 10^7$$

$$C := fpts\sum_i^{fpts}(Zout_{2,i})^2 - \left(\sum_i^{fpts}(Zout_{2,i})\right)^2 = 5.445 \cdot 10^{10}$$

$$D := 0.5 \cdot \left(fpts\sum_i^{fpts}(Zout_{1,i} \cdot (Zout_{2,i})^2) - \left(\sum_i^{fpts}(Zout_{1,i})\right) \cdot \left(\sum_i^{fpts}(Zout_{2,i})^2\right) + fpts\sum_i^{fpts}(Zout_{1,i}^3) - \left(\sum_i^{fpts}(Zout_{1,i})\right) \cdot \left(\sum_i^{fpts}(Zout_{1,i})^2\right)\right) = 5.529 \cdot 10^3$$

$$E := 0.5 \cdot \left(fpts\sum_i^{fpts}(Zout_{2,i} \cdot (Zout_{1,i})^2) - \left(\sum_i^{fpts}(Zout_{2,i})\right) \cdot \left(\sum_i^{fpts}(Zout_{1,i})^2\right) + fpts\sum_i^{fpts}(Zout_{2,i}^3) - \left(\sum_i^{fpts}(Zout_{2,i})\right) \cdot \left(\sum_i^{fpts}(Zout_{2,i})^2\right)\right) = -5.192 \cdot 10^{13}$$

Z1, i is a first vector of the real components referred to as conductance;

Z2, i is a second of the imaginary components referred to as susceptance; and

Z3, i is a third vector that represents the frequencies at which admittances are calculated.

This disclosure will work for ultrasonic systems and may possibly be applied to electrosurgical systems, even though electrosurgical systems do not rely on a resonance.

FIGS. 25-29 illustrate images taken from an impedance analyzer showing impedance/admittance circle plots for an ultrasonic device with the end effector jaw in various open or closed configurations and loading. The circle plots in solid line depict impedance and the circle plots in broken lines depict admittance, in accordance with at least one aspect of the present disclosure. By way of example, the impedance/admittance circle plots are generated by connecting an ultrasonic device to an impedance analyzer. The display of the impedance analyzer is set to complex impedance and complex admittance, which can be selectable from the front panel of the impedance analyzer. An initial display may be obtained with the jaw of the ultrasonic end effector in an open position and the ultrasonic device in an unloaded state, as described below in connection with FIG. 25, for example. The autoscale display function of the impedance analyzer may be used to generate both the complex impedance and admittance circle plots. The same display is used for subsequent runs of the ultrasonic device with different loading conditions as shown in the subsequent FIGS. 25-29. A LabVIEW application may be employed to upload the data files. In another technique, the display images may be captured with a camera, such as a smartphone camera, like an iPhone or Android. As such, the image of the display may include some "keystone-ing" and in general may not appear to be parallel to the screen. Using this technique, the circle plot traces on the display will appear distorted in the captured image. With this approach, the material located in the jaws of the ultrasonic end effector can be classified.

The complex impedance and complex admittance are just the reciprocal of one another. No new information should be added by looking at both. Another consideration includes determining how sensitive the estimates are to noise when using complex impedance or complex admittance.

In the examples illustrated in FIGS. 25-29, the impedance analyzer is set up with a range to just capture the main resonance. By scanning over a wider range of frequencies more resonances may be encountered and multiple circle plots may be formed. An equivalent circuit of an ultrasonic transducer may be modeled by a first "motional" branch having a serially connected inductance Ls, resistance Rs and capacitance Cs that define the electromechanical properties of the resonator, and a second capacitive branch having a static capacitance C0. In the impedance/admittance plots shown in FIGS. 25-29 that follow, the values of the components of the equivalent circuit are:

$Ls=L1=1.1068$ H $Rs=R1=311.35211 \Omega$ $Cs=C1=7.43265$ pF $C0=C0=3.64026$ nF

The oscillator voltage applied to the ultrasonic transducer is 500 mV and the frequency is swept from 55 kHz to 56 kHz. The impedance (Z) scale is 200 Ω/div and the admittance (Y) scale is 500 μS/div. Measurements of values that may characterize the impedance (Z) and admittance (Y) circle plots may be obtained at the locations on the circle plots as indicated by an impedance cursor and an admittance cursor.

State of Jaw: Open With no Loading

Figure 25:
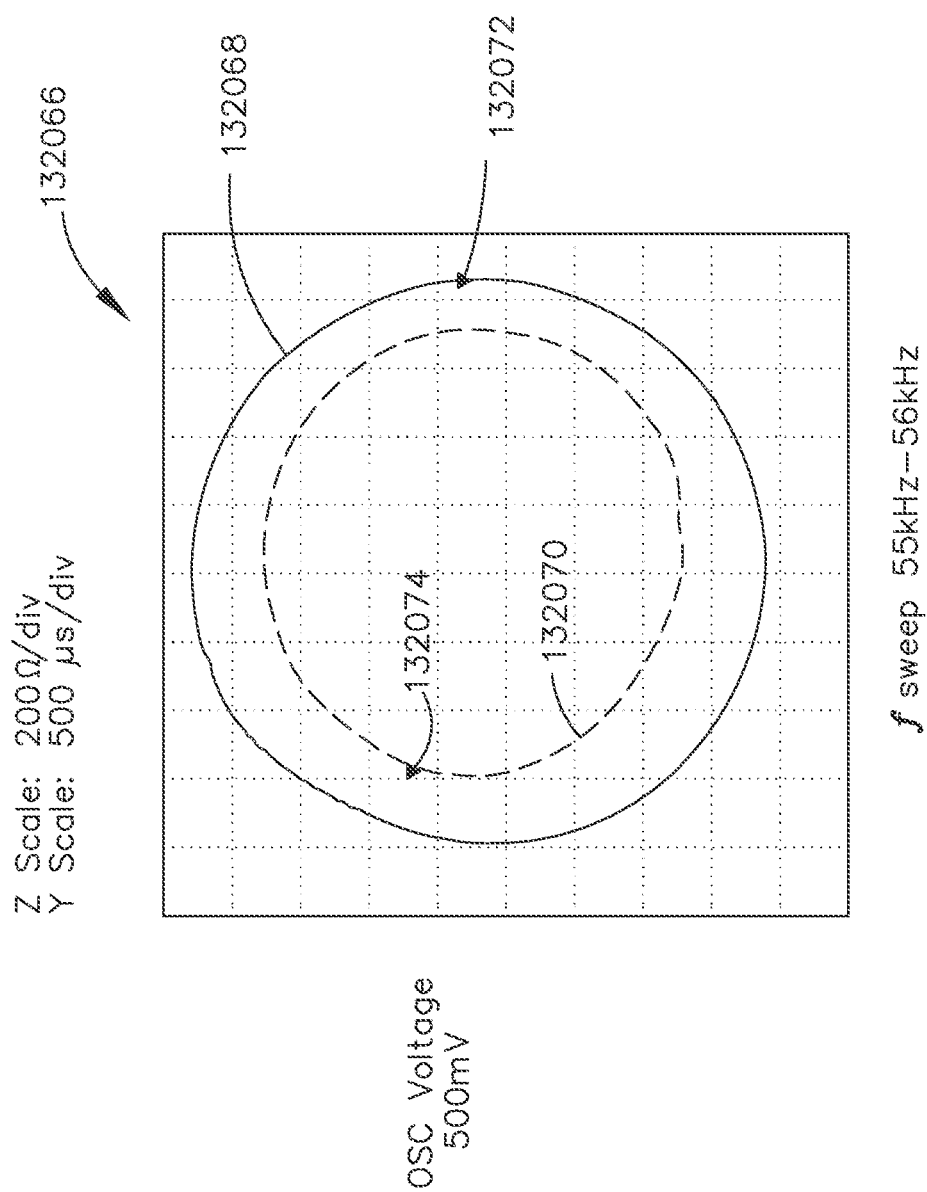
FIG. 25 is a graphical display of an impedance analyzer showing impedance/admittance circle plots for an ultrasonic device with the jaw open and no loading where complex admittance is depicted in broken line and complex impedance is depicted in solid line, in accordance with at least one aspect of the present disclosure.

FIG. 25 is a graphical display 132066 of an impedance analyzer showing complex impedance (Z)/admittance (Y) circle plots 132068, 132070 for an ultrasonic device with the jaw open and no loading where a circle plot 132068 in solid line depicts complex impedance and a circle plot 132070 in broken line depicts complex admittance, in accordance with at least one aspect of the present disclosure. The oscillator voltage applied to the ultrasonic transducer is 500 mV and the frequency is swept from 55 kHz to 56 kHz. The impedance (Z) scale is 200 Ω/div and the admittance (Y) scale is 500 μS/div. Measurements of values that may characterize the complex impedance (Z) and admittance (Y) circle plots 132068, 132070 may be obtained at locations on the circle plots 132068, 132070 as indicated by the impedance cursor 132072 and the admittance cursor 132074. Thus, the impedance cursor 132072 is located at a portion of the impedance circle plot 132068 that is equivalent to about 55.55 kHz, and the admittance cursor 132074 is located at a portion of the admittance circle plot 132070 that is equivalent to about 55.29 kHz. As depicted in FIG. 25, the position of the impedance cursor 132072 corresponds to values of:

$R=1.66026 \Omega$ $X=697.309 \Omega$

Where R is the resistance (real value) and X is the reactance (imaginary value). Similarly, the position of the admittance cursor 132074 corresponds to values of:

$G=64.0322$ μS $B=1.63007$ mS

Where G is the conductance (real value) and B is susceptance (imaginary value).

State of Jaw: Clamped on Dry Chamois

Figure 26:
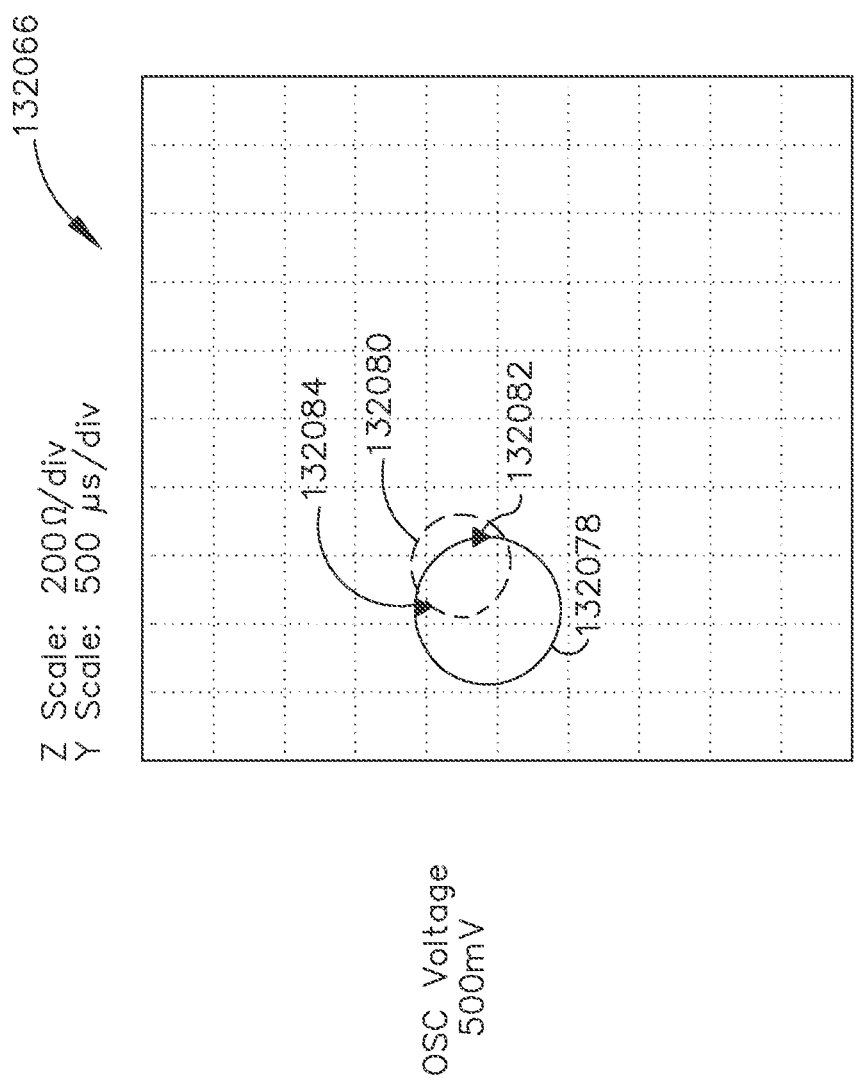
FIG. 26 is a graphical display of an impedance analyzer showing impedance/admittance circle plots for an ultrasonic device with the jaw clamped on dry chamois where complex admittance is depicted in broken line and complex impedance is depicted in solid line, in accordance with at least one aspect of the present disclosure.

FIG. 26 is a graphical display 132076 of an impedance analyzer showing complex impedance (Z)/admittance (Y) circle plots 132078, 132080 for an ultrasonic device with the jaw of the end effector clamped on dry chamois where the impedance circle plot 132078 is shown in solid line and the admittance circle plot 132080 is shown in broken line, in accordance with at least one aspect of the present disclosure. The voltage applied to the ultrasonic transducer is 500 mV and the frequency is swept from 55 kHz to 56 kHz. The impedance (Z) scale is 200 Ω/div and the admittance (Y) scale is 500 μS/div.

Measurements of values that may characterize the complex impedance (Z) and admittance (Y) circle pots 132078, 132080 may be obtained at locations on the circle plots 132078, 132080 as indicated by the impedance cursor 132082 and the admittance cursor 132084. Thus, the impedance cursor 132082 is located at a portion of the impedance circle plot 132078 that is equivalent to about 55.68 kHz, and the admittance cursor 132084 is located at a portion of the admittance circle plot 132080 that is equivalent to about 55.29 kHz. As depicted in FIG. 26, the position of the impedance cursor 132082 corresponds to values of:

$R=434.577 \Omega$ $X=-758.772 \Omega$

Where R is the resistance (real value) and X is the reactance (imaginary value).

Similarly, the position of the admittance cursor 132084 corresponds to values of:

$G=85.1712$ μS $B=1.49569$ mS

Where G is the conductance (real value) and B is susceptance (imaginary value).

State of Jaw: Tip Clamped on Moist Chamois

Figure 27:
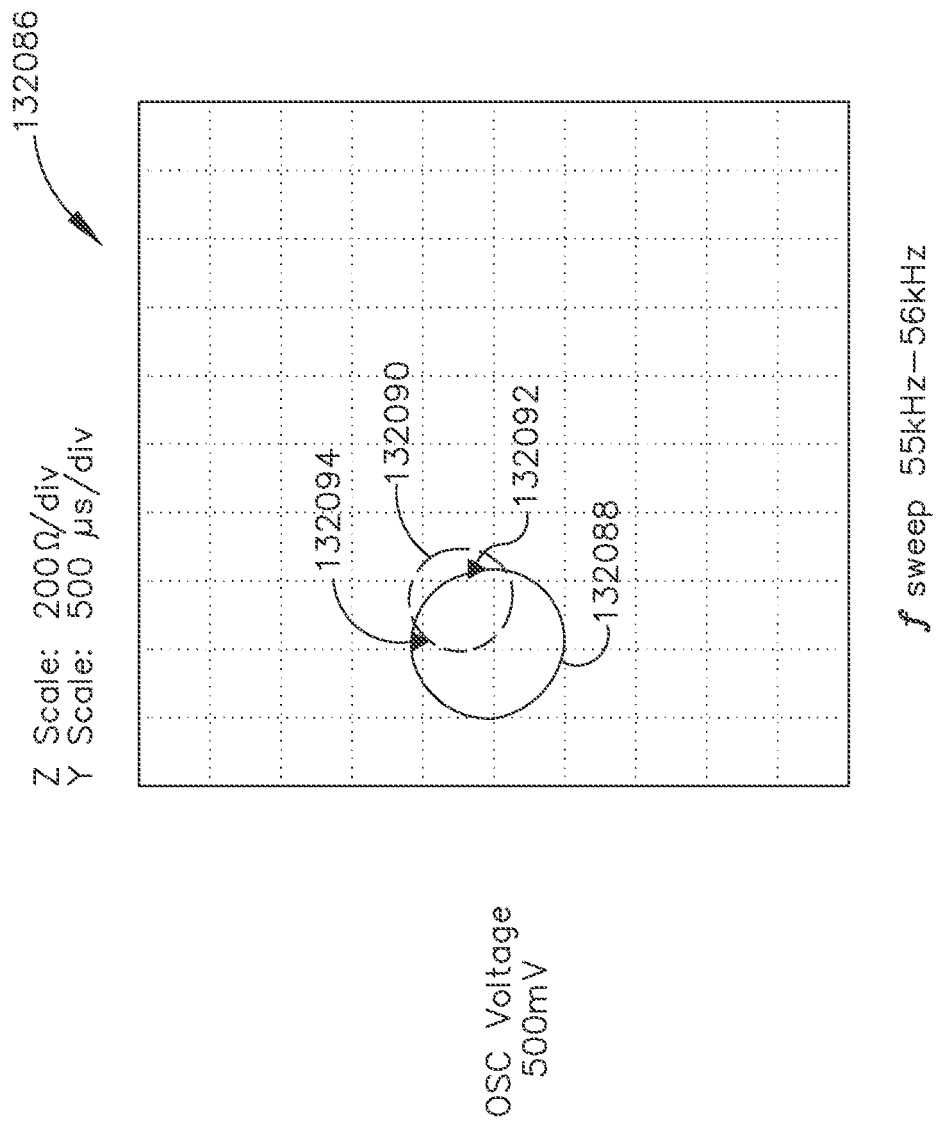
FIG. 27 is a graphical display of an impedance analyzer showing impedance/admittance circle plots for an ultrasonic device with the jaw tip clamped on moist chamois where complex admittance is depicted in broken line and complex impedance is depicted in solid line, in accordance with at least one aspect of the present disclosure.

FIG. 27 is a graphical display 132086 of an impedance analyzer showing complex impedance (Z)/admittance (Y) circle plots 132098, 132090 for an ultrasonic device with the jaw tip clamped on moist chamois where the impedance circle plot 132088 is shown in solid line and the admittance circle plot 132090 is shown in broken line, in accordance with at least one aspect of the present disclosure. The voltage applied to the ultrasonic transducer is 500 mV and the frequency is swept from 55 kHz to 56 kHz. The impedance (Z) scale is 200 Ω/div and the admittance (Y) scale is 500 µS/div.

Figure 28:
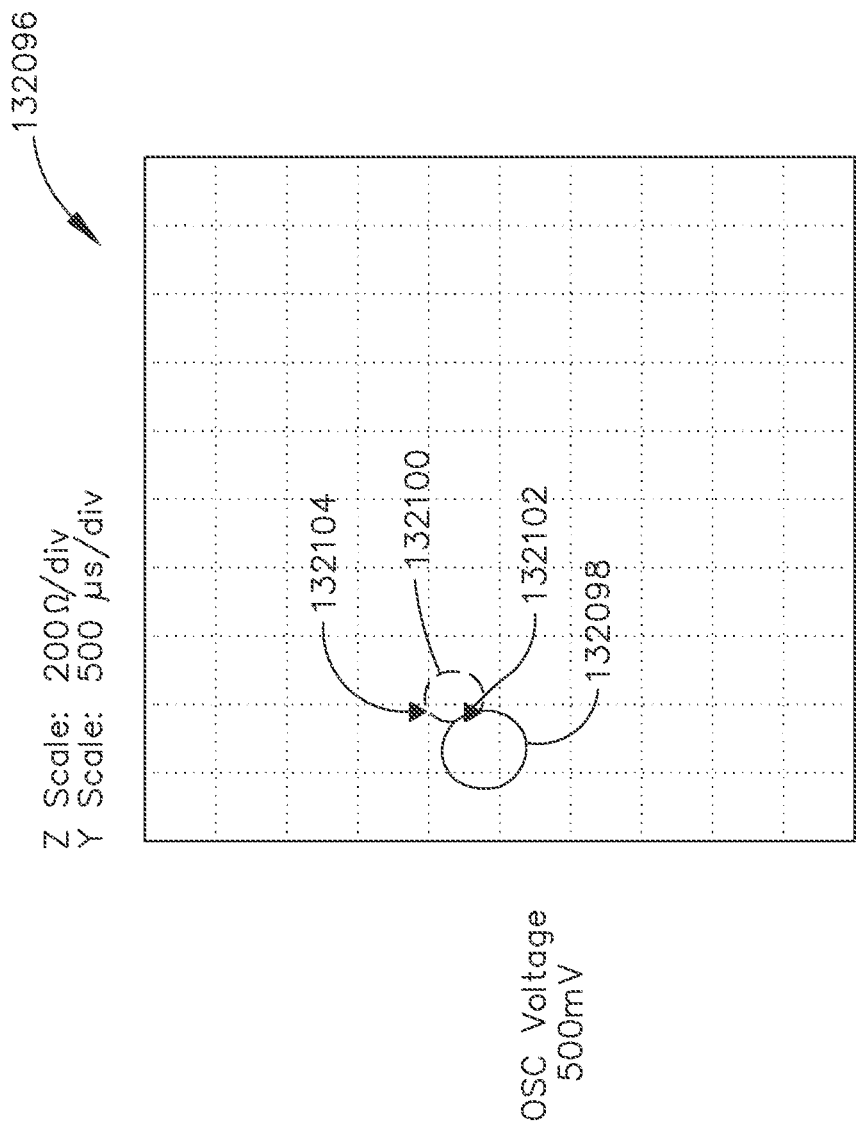
FIG. 28 is a graphical display of an impedance analyzer showing impedance/admittance circle plots for an ultrasonic device with the jaw fully clamped on moist chamois where complex admittance is depicted in broken line and complex impedance is depicted in solid line, in accordance with at least one aspect of the present disclosure.

Measurements of values that may characterize the complex impedance (Z) and complex admittance (Y) circle plots 132088, 132090 may be obtained at locations on the circle plots 132088, 132090 as indicated by the impedance cursor 132092 and the admittance cursor 132094. Thus, the impedance cursor 132092 is located at a portion of the impedance circle plot 132088 that is equivalent to about 55.68 kHz, and the admittance cursor 132094 is located at a portion of the admittance circle plot 132090 that is equivalent to about 55.29 kHz. As depicted in FIG. 28, the impedance cursor 132092 corresponds to values of:

$R=445.259\Omega$ $X=-750.082\Omega$

Where R is the resistance (real value) and X is the reactance (imaginary value). Similarly, the admittance cursor 132094 corresponds to values of:

$G=96.2179\ \mu S$ $B=1.50236\ mS$

Where G is the conductance (real value) and B is susceptance (imaginary value).

State of Jaw: Fully Clamped on Moist Chamois

FIG. 28 is a graphical display 132096 of an impedance analyzer showing complex impedance (Z)/admittance (Y) circle plots 132098, 132100 for an ultrasonic device with the jaw fully clamped on moist chamois where the impedance circle plot 132098 is shown in solid line and the admittance circle plot 132100 is shown in broken line, in accordance with at least one aspect of the present disclosure. The voltage applied to the ultrasonic transducer is 500 mV and the frequency is swept from 55 kHz to 56 kHz. The impedance (Z) scale is 200 Ω/div and the admittance (Y) scale is 500 µS/div.

Measurements of values that may characterize the impedance and admittance circle plots 132098, 132100 may be obtained at locations on the circle plots 132098, 1332100 as indicated by the impedance cursor 13212 and admittance cursor 132104. Thus, the impedance cursor 132102 is located at a portion of the impedance circle plot 132098 equivalent to about 55.63 kHz, and the admittance cursor 132104 is located at a portion of the admittance circle plot 132100 equivalent to about 55.29 kHz. As depicted in FIG. 28, the impedance cursor 132102 corresponds to values of R, the resistance (real value, not shown), and X, the reactance (imaginary value, also not shown).

Similarly, the admittance cursor 132104 corresponds to values of:

$G=137.272\ \mu S$ $B=1.48481\ mS$

Where G is the conductance (real value) and B is susceptance (imaginary value).

State of Jaw: Open With no Loading

Figure 29:
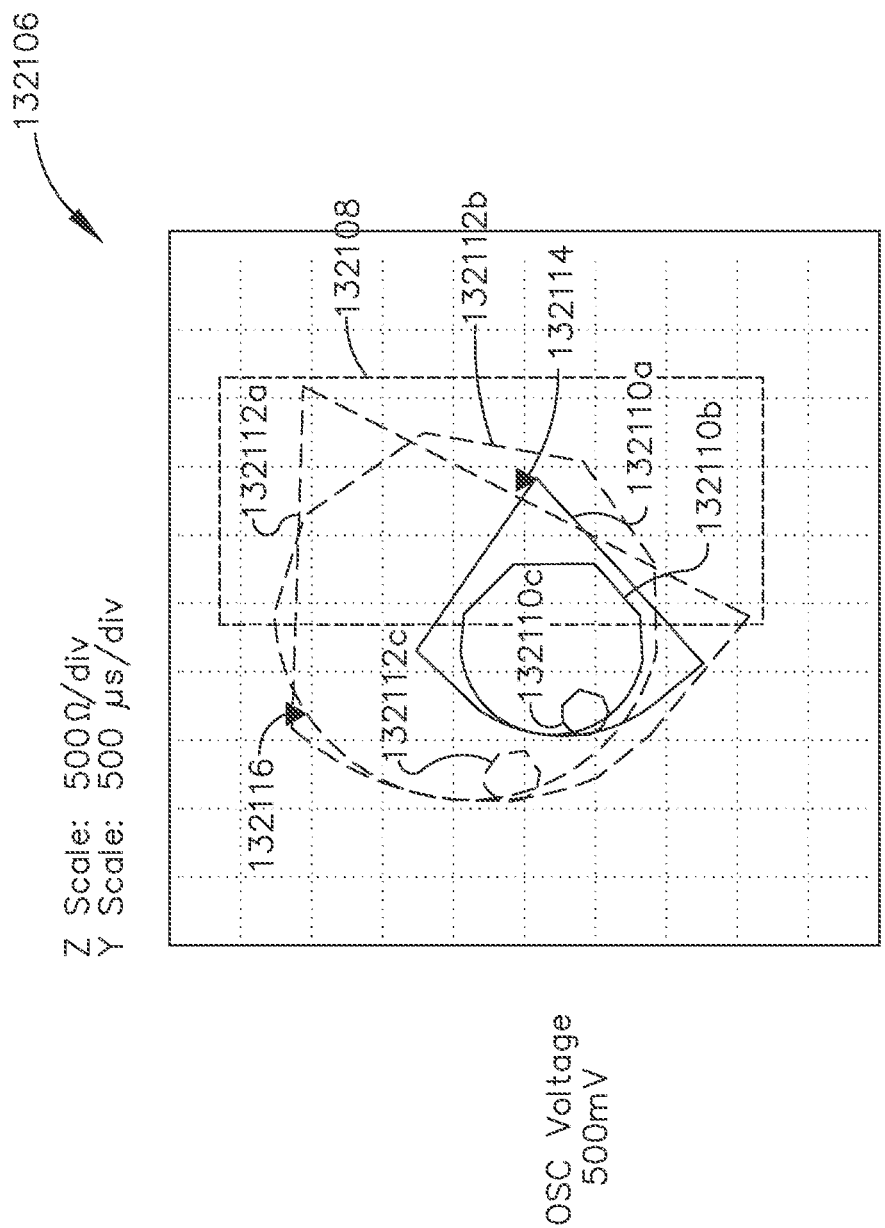
FIG. 29 is a graphical display of an impedance analyzer showing impedance/admittance plots where frequency is swept from 48 kHz to 62 kHz to capture multiple resonances of an ultrasonic device with the jaw open where the rectangular overlay shown in broken line is to help see the circles, in accordance with at least one aspect of the present disclosure.

FIG. 29 is a graphical display 132106 of an impedance analyzer showing impedance (Z)/admittance (Y) circle plots where frequency is swept from 48 kHz to 62 kHz to capture multiple resonances of an ultrasonic device with the jaw open and no loading where the area designated by the rectangle 132108 shown in broken line is to help see the impedance circle plots 132110a, 132110b, 132110c shown in solid line and the admittance circle plots 132112a, 132112b, 132112c, in accordance with at least one aspect of the present disclosure. The voltage applied to the ultrasonic transducer is 500 mV and the frequency is swept from 48 kHz to 62 kHz. The impedance (Z) scale is 500 Ω/div and the admittance (Y) scale is 500 µS/div.

Measurements of values that may characterize the impedance and admittance circle plots 132110a-c, 132112a-c may be obtained at locations on the impedance and admittance circle plots 132110a-c, 132112a-c as indicated by the impedance cursor 132114 and the admittance cursor 132116. Thus, the impedance cursor 132114 is located at a portion of the impedance circle plots 132110a-c equivalent to about 55.52 kHz, and the admittance cursor 132116 is located at a portion of the admittance circle plot 132112a-c equivalent to about 59.55 kHz. As depicted in FIG. 29, the impedance cursor 132114 corresponds to values of:

$R=1.86163\ k\Omega$ $X=-536.229\Omega$

Where R is the resistance (real value) and X is the reactance (imaginary value). Similarly, the admittance cursor 132116 corresponds to values of:

$G=649.956\ \mu S$ $B=2.51975\ mS$

Where G is the conductance (real value) and B is susceptance (imaginary value).

Because there are only 400 samples across the sweep range of the impedance analyzer, there are only a few points about a resonance. So, the circle on the right side becomes choppy. But this is only due to the impedance analyzer and the settings used to cover multiple resonances.

When multiple resonances are present, there is more information to improve the classifier. The circle plots 132110a-c, 132112a-c fit can be calculated for each as encountered to keep the algorithm running fast. So once there is a cross of the complex admittance, which implies a circle, during the sweep, a fit can be calculated.

Benefits include in-the-jaw classifier based on data and a well-known model for ultrasonic systems. Count and characterizations of circles are well known in vision systems. So data processing is readily available. For example, a closed form solution exists to calculate the radius and axes' offsets for a circle. This technique can be relatively fast.

TABLE 2 is a list of symbols used for lumped parameter model of a piezoelectric transducer (from IEEE 177 Standard).

TABLE 2

| Symbols | Meaning | SI Units | Equations | Tables | Figures |
|---|---|---|---|---|---|
| $B_p$ | Equivalent parallel susceptance of vibrator | mho | | 2 | |
| $C_o$ | Shunt (parallel) capacitance in the equivalent electric circuit | farad | 2, 3, 4, 8 | 5 | 1, 4 |
| $C_1$ | Motional capacitance in the equivalent electric circuit | farad | 2, 3, 4, 6, 8, 9 | 5 | 1, 4 |
| f | Frequency | hertz | | | 3 |
| $f_a$ | Antiresonance frequency, zero susceptance | hertz | | 2, 4 | 2, 3 |
| $f_m$ | Frequency of maximum admittance (minimum impedance) | hertz | | 2, 4 | 2, 3 |
| $f_n$ | Frequency of minimum admittance (maximum impedance) | hertz | | 2, 4 | 2, 3 |
| $f_p$ | Parallel resonance frequency $$(\text{lossless}) = \frac{1}{2\pi\sqrt{L_1\frac{C_1 C_O}{C_1 + C_O}}}$$ | hertz | 2, 3 | 2, 4 | 2 |
| $f_r$ | Resonance frequency, zero substance | hertz | | 2, 4 | 2, 3 |
| $f_B$ | Motional (series) resonance frequency ½ | hertz | 2, 3, 6, 7, 9, 11a, 11b, 11c, 12, | 2, 4 | 2, 3, 6, 8 |
| $G_p$ | Equivalent parallel conductance of vibrator | | 1 | | |
| $L_1$ | Motional inductance in the equivalent electric circuit | henry | 8, 9 | | 1, 4, 5 |
| M | Figure of merit of a vibrator $= \frac{Q}{r}$ $$M = \frac{1}{\omega_s C_O R_1}$$ | dimensionless | 10, 11a, 11b | 3, 4, 5 | |
| Q | Quality factor $$Q = \frac{\omega_s L_1}{R_1} = \frac{1}{\omega_s C_1 R_1} = rM$$ | dimensionless | 12 | 3 | 6, 8 |
| r | Capacitance ratio $$r = \frac{C_o}{C_1}$$ | dimensionless | 2, 3, 10, 11 | 2, 3, 4, 5 | 8 |
| $R_a$ | Impedance at zero phase angle near antiresonance | ohm | | | 2, 3 |
| $R_e$ | Equivalent series resistance of vibrator | ohm | | | 1, 2 |
| $R_r$ | Impedance at $f_r$ zero phase angle | ohm | | | 2, 3 |
| $R_1$ | Motional resistance in the equivalent electric circuit | ohm | 4, 8, 10, 11a, 11b, 11c, 12 | 2, 5 | 1, 3, 4, 6, 7, 8 |
| $X_e$ | Equivalent series reactance of vibrator | ohm | | | 1, 2 |
| $X_o$ | Reactance of shunt (parallel) capacitance at series resonance $= \frac{1}{\omega_s C_o}$ | ohm | 1, 4, 5 | 5 | 3, 7 |
| $X_1$ | Reactance of motional (series) arm of vibrator $$X_1 = \omega L_1 - \frac{1}{\omega C_1}$$ | ohm | | 2 | 2 |

TABLE 2-continued

| Symbols | Meaning | SI Units | Equations | Tables | Figures |
|---|---|---|---|---|---|
| Y | Admittance of vibrator $$Y = G_p + jB_p = \frac{1}{z}$$ | mho | 1 | | |
| $Y_m$ | Maximum admittance of vibrator | mho | | | 3 |
| $Y_n$ | Minimum admittance of vibrator | mho | | | 3 |
| Z | Impedance of vibrator $Z = R_e + jX_e$ | ohm | 1 | | |
| $Z_m$ | Minimum impedance of vibrator | ohm | | | 3 |
| $Z_n$ | Maximum impedance of vibrator | ohm | | | 3 |
| | Absolute value of impedance of vibrator $$Z = \sqrt{R_e^2 + X_e^2}$$ | ohm | | 2 | 2 |
| | Absolute value of impedance at $f_m$ (minimum impedance) | ohm | | | 2 |
| | Absolute value of impedance at $f_n$ (maximum impedance) | ohm | | | 2 |
| δ | Normalized damping factor δ = $\omega_o C_o R_1$ | dimensionless | 1 | 2 | |
| Ω | Normalized frequency factor $\Omega = \frac{f^2 - f_s^2}{f_p^2 - f_s^2}$ | dimensionless | 1 | 2 | |
| ω | Circular (angular) frequency ω = 2πf | hertz | | 2 | |
| $\omega_s$ | Circular frequency at motional resonance $\omega_s = 2\pi f_s$ | hertz | | | |

TABLE 3 is a list of symbols for the transmission network (from IEEE 177 Standard).

TABLE 3

| Symbols | Meaning | SI Units | Equations | Tables | Figures |
|---|---|---|---|---|---|
| b | Normalized compensation factor $1 - \frac{1}{4\pi^2 f_s^2 C_O L_O}$ | dimensionless | 4, 10 | 5 | |
| B | Normalized admittance factor | dimensionless | 10 | 5 | |
| C | Normalized admittance factor | dimensionless | 10 | 5 | |
| $C_{A-B}$ | Stray capacitance between the terminals A-B (FIG. 4) | farad | | | |
| $C_L$ | Load capacitance | farad | 6 | | 4 |
| $C_T$ | Shunt capacitance terminating transmission circuit | farad | 4, 10 | 5 | 4 |
| $C_{L1}$ | Load capacitance | farad | 7 | | |
| $C_{L2}$ | Load capacitance | farad | 7 | | |
| $e_2$ | Output voltage of transmission network | volt | | | 4 |
| $f_{mT}$ | Frequency of maximum transmission | hertz | 10 | | |
| $F_{sL1}$ | Motional resonance frequency of combination of vibrator and $C_{L1}$ | hertz | 7 | | |

TABLE 3-continued

| Symbols | Meaning | SI Units | Equations | Tables | Figures |
|---|---|---|---|---|---|
| $F_{sL2}$ | Motional resonance frequency of combination of vibrator and $C_{L2}$ | hertz | 7 | | |
| $i_1$ | Input current to transmission network | ampere | | | 4 |
| $L_0$ | Compensation inductance shunting vibrator | henry | | | 4 |
| $M_T$ | Figure of merit of transmission network $$\text{termination} = \frac{1}{2\pi f_s C_T R_T} = \frac{X_T}{R_T}$$ | dimensionless | 4, 10 | 5 | |
| $R_T$ | Shunt resistance termination of transmission network | ohm | 4, 11a, 11b, 11c, 12 | 5 | 4, 6, 7, 8 |
| $R_{sL2}$ | Standard resistor | ohm | 4, 5 | 5 | 7 |
| S | Detector sensitivity smallest detectable current change/current | dimensionless | 12 | | 6 |
| x | Normalized frequency $$\text{factor } x = \frac{f^2}{f_s^2} - 1 = \frac{\Omega}{r}$$ | dimensionless | 12 | | |
| $X_{A-B}$ | Reactance of stray capacitance $C_{A-B}$ | ohm | | | |
| $X_T$ | Reactance of $C_T$ at the motional resonance frequency $$X_T = \frac{1}{2\pi f_s C_T}$$ | ohm | 4 | 5 | |
| $x_{mT}$ | Normalized frequency factor at the frequency of maximum transmission | dimensionless | | 5 | |
| $\Delta C_L$ | $\Delta C_L = C_{L2} - C_{L1}$ | farad | 6, 7 | | |
| $\Delta f$ | $\Delta f_1 = f_{sL1} - f_{sL2}$ | hertz | 6, 7 | | 6, 8 |
| $\Delta f_1$ | $\Delta f_1 = f_{sL1} - f_s$ | hertz | 6, 7 | | |
| $\Delta f_2$ | $\Delta f_1 = f_{sL2} - f_s$ | hertz | 6, 7 | | |

*Refers to real roots; complex roots to be disregarded.

TABLE 4 is a list of solutions for various characteristic frequencies (from IEEE 177 Standard).

Solutions for the Various Characteristic Frequencies

TABLE 4

| Characteristic Frequencies | Meaning | Condition | Constituent Equation for Frequency | Root | 57 IEEE 14.S1[1] |
|---|---|---|---|---|---|
| $f_m$ | Frequency of maximum admittance (minimum impedance) | = 0 | $-2\delta^2(\Omega + r) - 2\Omega r(1 - \Omega) - \Omega^2 = 0$ | lower* | $f_m$ |
| $f_a$ | Motional (series) resonance frequency | $X_1 = 0$ | $\Omega = 0$ | | $f_a$ |
| $f_r$ | Resonance frequency | $X_e = B_p = 0$ | $\Omega(1 - \Omega) - \delta^2 = 0$ | lower | $f_r$ |
| $f_a$ | Antiresonance frequency | $X_e = B_p = 0$ | $\Omega(1 - \Omega) - \delta^2 = 0$ | upper | $f_a$ |
| $f_p$ | Parallel resonance frequency (lossless) | $\|=\infty\| R_1 = 0$ | $\Omega = 1$ | | $f_p$ |
| $f_n$ | Frequency of minimum admittance (maximum impedance) | = 0 | $-2\delta^2(\Omega + r) - 2\Omega r(1 - \Omega) - \Omega^2 = 0$ | upper* | $f_n$ |

*Refers to real roots; complex roots to be disregarded

TABLE 5 is a list of losses of three classes of piezoelectric materials.

TABLE 5

| Type of Piezoelectric Vibrator | Q = Mr | r | Q$^r$/r min |
|---|---|---|---|
| Piezoelectric Ceramics | 90 - 500 | 2 - 40 | 200 |
| Water-Soluble Piezoelectric Crystals | 200 - 50,000 | 3 - 500 | 80 |
| Quartz | $10^4 - 10^7$ | 100 - 50,000 | 2000 |

Minimum Values for the Ratio Qr/r to be Expected for Various Types of Piezoelectric Vibrators TABLE 6 illustrates jaw conditions, estimated parameters of a circle based on real time measurements of complex impedance/admittance, radius (re) and offsets (ae and be) of the circle represented by measured variables Re, Ge, Xe, Be, and parameters of a reference circle plots, as described in FIGS. 25-29, based on real time measurements of complex impedance/admittance, radius (rr) and offsets (ar, br) of the reference circle represented by reference variables Rref, Gref, Xref, Bref. These values are then compared with established values for given conditions. These conditions may be: 1) open with nothing in jaws, 2) tip bite 3) full bite and staple in jaws. The equivalent circuit of the ultrasonic transducer was modeled as follows and the frequency was swept from 55 kHz to 56 kHz:

Ls=L1=1.1068 H

Rs=R1=311.352Ω

Cs=C1=7.43265 pF and

C0=C0=3.64026 nF

TABLE 6

| Reference Jaw Conditions | Reference Circle Plot | | | |
|---|---|---|---|---|
| | $R_{ref}$(Ω) | $G_{ref}$(μS) | $X_{ref}$(Ω) | $B_{ref}$(mS) |
| Jaw open and no loading | 1.66026 | 64.0322 | −697.309 | 1.63007 |
| Jaw clamped on dry chamois | 434.577 | 85.1712 | −758.772 | 1.49569 |
| Jaw tip clamped on moist chamois | 445.259 | 96.2179 | −750.082 | 1.50236 |
| Jaw fully clamped on moist chamois | | 137.272 | | 1.48481 |

In use, the ultrasonic generator sweeps the frequency, records the measured variables, and determines estimates Re, Ge, Xe, Be. These estimates are then compared to reference variables Rref, Gref, Xref, Bref stored in memory (e.g., stored in a look-up table) and determines the jaw conditions. The reference jaw conditions shown in TABLE 6 are examples only. Additional or fewer reference jaw conditions may be classified and stored in memory. These variables can be used to estimate the radius and offsets of the impedance/admittance circle.

Figure 30:
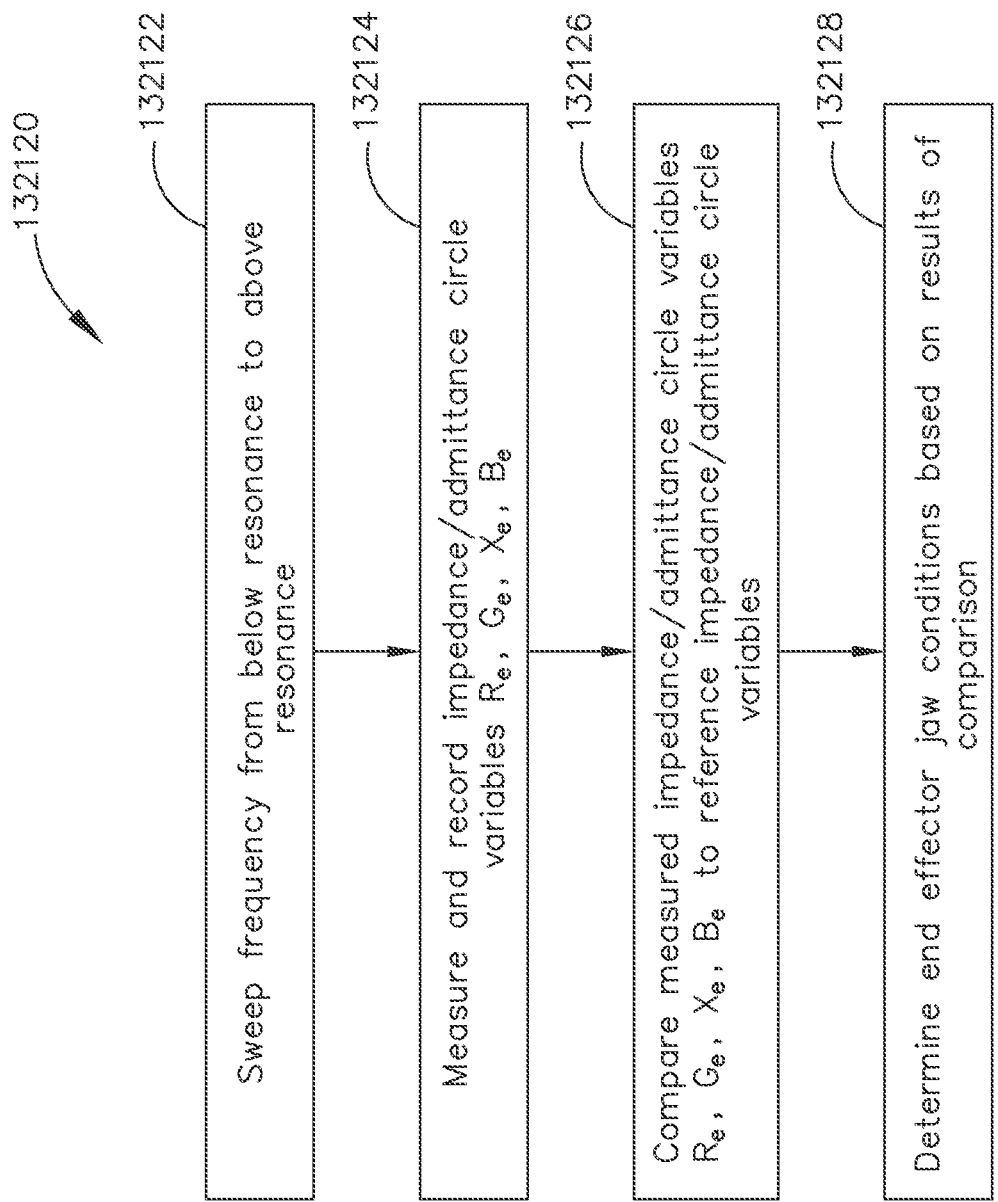
FIG. 30 is a logic flow diagram of a process depicting a control program or a logic configuration to determine jaw conditions based on estimates of the radius and offsets of an impedance/admittance circle, in accordance with at least one aspect of the present disclosure.

FIG. 30 is a logic flow diagram 132120 of a process depicting a control program or a logic configuration to determine jaw conditions based on estimates of the radius (r) and offsets (a, b) of an impedance/admittance circle, in accordance with at least one aspect of the present disclosure. Initially a data base or lookup table is populated with reference values based on reference jaw conditions as described in connection with FIGS. 25-29 and TABLE 6. A reference jaw condition is set and the frequency is swept from a value below resonance to a value above resonance. The reference values Rref, Gref, Xref, Bref that define the corresponding impedance/admittance circle plot are stored in a database or lookup table. During use, under control of a control program or logic configuration a control circuit of the generator or instrument causes the frequency to sweep 132122 from below resonance to above resonance. The control circuit measures and records 132124 (e.g., stores in memory) the variables Re, Ge, Xe, Be that define the corresponding impedance/admittance circle plot and compares 132126 them to the reference values Rref, Gref, Xref, Bref stored in the database or lookup table. The control circuit determines 132128, e.g., estimates, the end effector jaw conditions based on the results of the comparison.

Smart Ultrasonic Blade Application for Reusable and Disposable Devices

The smart blade algorithm uses spectroscopy to identify the status of an ultrasonic blade. This capability can be applied to reusable and disposable devices with detachable clamp arms to distinguish if the disposable portion of the device has been installed correctly. The status of the ultrasonic blade may be determined using smart blade algorithm techniques for estimating or classifying the state of the jaw of an ultrasonic device described in connection with FIGS. 19-21 under the heading ESTIMATING THE STATE OF THE JAW (PAD BURN THROUGH, STAPLES, BROKEN BLADE, BONE IN JAW, TISSUE IN JAW and/or FIGS. 22-30 under the heading STATE OF JAW CLASSIFIER BASED ON MODEL and/or techniques for estimating the temperature of the ultrasonic blade are described in related U.S. Provisional Patent Application No. 62/640,417, titled TEMPERATURE CONTROL IN ULTRASONIC DEVICE AND CONTROL SYSTEM THEREFOR, to Nott et al, which is incorporated herein by reference in its entirety.

The smart blade algorithm techniques described herein can be employed to identify the status of components of reusable and disposable devices. In one aspect, the status of the ultrasonic blade may be determined to distinguish if disposable portions of reusable and disposable devices have been installed correctly or incorrectly.

FIGS. 31 and 32 illustrate a reusable and disposable ultrasonic device 132400 configured to identify the status of the ultrasonic blade 132402 and determine the clocked status of the clamp arm 132404 to determine whether a portion of the reusable and disposable ultrasonic device 132400 has been installed correctly, in accordance with at least one aspect of the present disclosure. FIG. 32 is an end effector 132406 portion of the reusable and disposable ultrasonic device 132400 shown in FIG. 31. Similarities and differences between the spectroscopy signatures can be used to determine whether the reusable and disposable components of the reusable and disposable ultrasonic device 132400 have been installed correctly or incorrectly.

The reusable and disposable ultrasonic device 132400 shown in FIGS. 31 and 32 includes a reusable handle 132408 and a disposable ultrasonic waveguide/blade 132402. Prior to use, a proximal end 132410 of the disposable ultrasonic waveguide/blade 132402 is inserted 132414 into a distal opening 132412 of the reusable handle 132408 and twisted or rotated clockwise 132416 to lock the disposable ultrasonic waveguide/blade 132402 into the handle 132408 as shown in FIG. 31. If the disposable ultrasonic waveguide/blade 132402 is not fully inserted 132414 and/or fully rotated clockwise 132416, the reusable and disposable ultrasonic device 132400 will not operate properly. For example, improper insertion 132414 and rotation 132416 of the disposable ultrasonic waveguide/blade 132402 will result in poor mechanical coupling of the disposable ultrasonic waveguide/blade 132402 and will produce a different spectroscopy signature. Therefore, the smart blade algorithm techniques described herein can be used to determine if the disposable portion of the reusable and disposable ultrasonic device 132400 has been inserted 132414 and rotated 132416 completely.

In another misaligned configuration, if the clamp arm 132404 shown in FIG. 32 is clocked (rotated) relative to the ultrasonic blade 132402, the orientation of the ultrasonic blade 132402 relative to the clamp arm 132404 will be out of alignment. This also will produce a different spectroscopic signature when the reusable and disposable ultrasonic device 132400 is actuated and/or clamped. Therefore, the smart blade algorithm techniques described herein can be used to determine if the disposable portion of the reusable and disposable ultrasonic device 132400 has been properly clocked (rotated) relative to the clamp arm 132404.

In another aspect, the smart blade algorithm techniques described herein can be used to determine if a disposable portion of the reusable and disposable ultrasonic device 132400 has been pushed in or inserted 132414 all the way into the reusable portion 132408. This may be applicable to the reusable and disposable ultrasonic device 132400 in FIG. 33 below where a reusable portion such as the handle 132408, for example, is 132414 inserted into a disposable portion, such as the ultrasonic blade 132402, for example, prior to operation.

Figure 33:
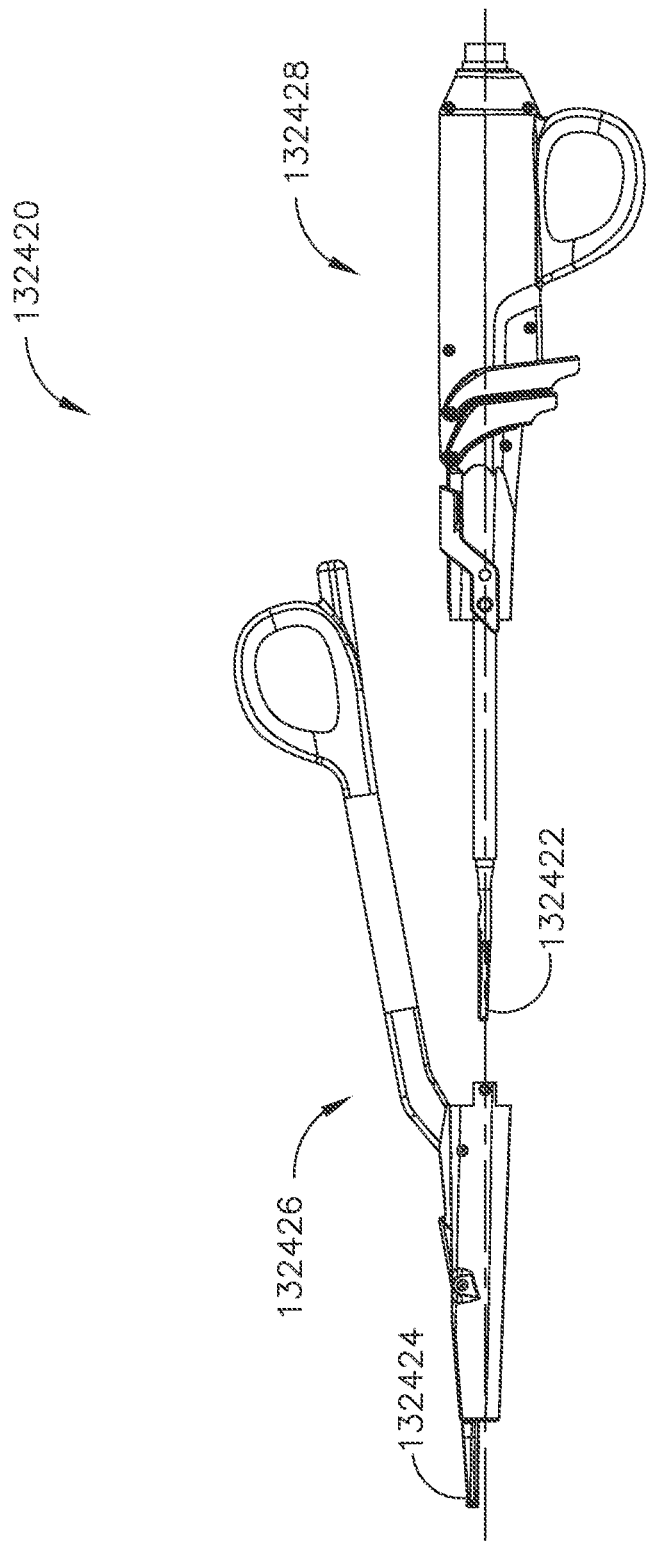
FIG. 33 is an ultrasonic device configured to identify the status of the ultrasonic blade and determine whether the clamp arm is not completely distal to determine whether a disposable portion of a reusable and disposable ultrasonic device has been installed correctly, in accordance with at least one aspect of the present disclosure.

FIG. 33 is a reusable and disposable ultrasonic device 132420 configured to identify the status of the ultrasonic blade 132422 and determine whether the clamp arm 132424 is not completely distal to the reusable component 132428 in order to determine whether a disposable portion 132426 of the reusable and disposable ultrasonic device 132420 has been installed correctly, in accordance with at least one aspect of the present disclosure. If the clamp arm 132424 is not installed completely distal with respect to the reusable component 132428, there will be a different spectroscopic signature when the device is clamped. In another aspect, if the disposable portion 132426 is not installed completely distal on the reusable component 132428, the ultrasonic blade 132422 spectroscopic signature will be different when clamped into position. Therefore, the smart blade algorithm techniques described herein can be used to determine if the disposable portion 132426 of the reusable and disposable ultrasonic device 132420 has been fully and properly coupled to the reusable portion 132428.

Figure 34:
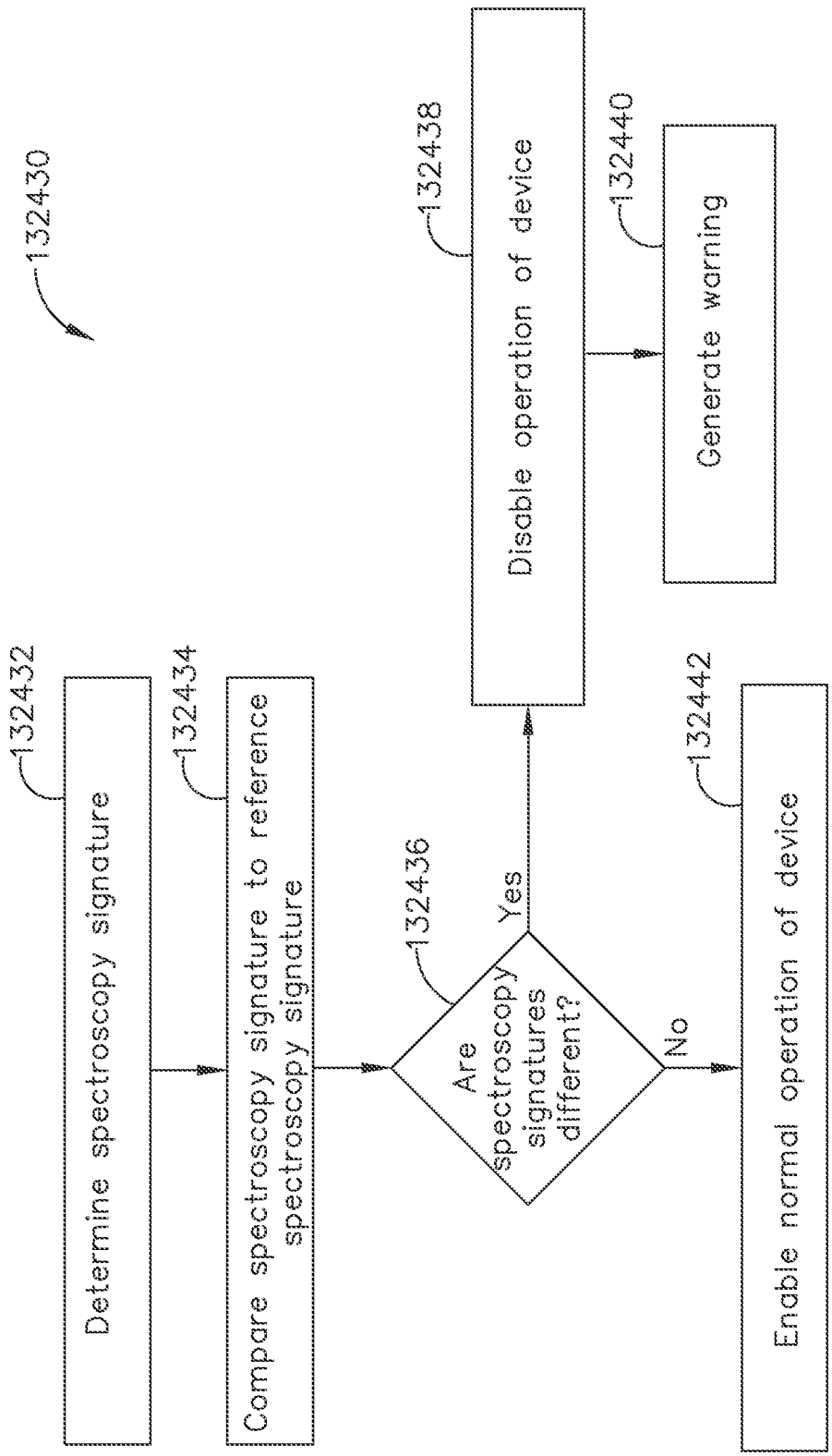
FIG. 34 is a logic flow diagram depicting a control program or a logic configuration to identify the status of components of reusable and disposable devices, in accordance with at least one aspect of the present disclosure.

FIG. 34 is a logic flow diagram 132430 depicting a control program or a logic configuration to identify the status of components of reusable and disposable ultrasonic devices, in accordance with at least one aspect of the present disclosure. According to the process depicted by the logic flow diagram 132430, a control circuit of the generator or instrument executes a smart blade algorithm technique and determines 132432 the spectroscopy signature of assembled reusable and disposable ultrasonic devices 132400, 132420 (FIGS. 32 and 33) comprising reusable and disposable components. The control circuit compares 132434 the measured spectroscopy signature to a reference spectroscopy signature, where the reference spectroscopy signature is associated with a properly assembled reusable and disposable ultrasonic device 132400, 132420 and is stored in a database or memory of the generator or instrument. When the control circuit determines 132436 that the measured spectroscopy signature differs from the reference spectroscopy signature, the control circuit disables 132438 the operation of the reusable and disposable ultrasonic device 132400, 132420 and generates 132440 a warning that can be perceived by the user. The waning may include a visible warning achieved by activating a light source, an auditory warning achieved by activating a sound source, or a tactile warning achieved by activating a vibration source. When the measured spectroscopy signature is the same or substantially similar to the reference spectroscopy signature, the control circuit enables 132442 the normal operation of the reusable and disposable ultrasonic device 132400, 132420.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered examples:

Example 1. A method of detecting proper installation of two or more components in an ultrasonic device, the ultrasonic device comprising an electromechanical ultrasonic system defined by a predetermined resonant frequency, the electromechanical ultrasonic system further comprising an ultrasonic transducer coupled to an ultrasonic blade, the method comprising: determining, by a processor or control circuit, a spectroscopy signature of the ultrasonic blade coupled to the ultrasonic transducer; comparing, by the processor or control circuit, the spectroscopy signature to a reference spectroscopy signature; determining, by the processor or control circuit, an installation state of the two or more components based on the comparison; and controlling, by the processor or control circuit, a delivery of power to the ultrasonic transducer based on the comparison.

Example 2. The method of Example 1, further comprising enabling, by the processor or control circuit, an operation of the ultrasonic device when the installation state of the two or more components is proper.

Example 3. The method of any one or more of Examples 1 through 2, further comprising: disabling, by the processor or control circuit, an operation of the ultrasonic device when the installation state of the two or more components is not proper; and generating, by the processor or control circuit, a warning.

Example 4. The method of Example 3, wherein generating, by the processor or control circuit, a warning comprises generating, by the processor or control circuit, a visible warning.

Example 5. The method of any one or more of Examples 3 through 4, wherein generating, by the processor or control circuit, a warning comprises generating, by the processor or control circuit, an audible warning.

Example 6. The method of any one or more of Examples 3 through 5, wherein generating, by the processor or control circuit, a warning comprises generating, by the processor or control circuit, a tactile warning.

Example 7. The method of any one or more of Examples 1 through 6, wherein determining, by a processor or control circuit, a spectroscopy signature of the ultrasonic blade coupled to the ultrasonic transducer comprises: measuring, by the processor or control circuit, a complex impedance of the ultrasonic transducer, wherein the complex impedance is defined as $$Z_g(t) = \frac{V_g(t)}{I_g(t)};$$

receiving, by the processor or control circuit, a complex impedance measurement data point; comparing, by the processor or control circuit, the complex impedance measurement data point to a data point in a reference complex impedance characteristic pattern; classifying, by the processor or control circuit, the complex impedance measurement data point based on a result of the comparison analysis; and assigning, by the processor or control circuit, a state or condition of an end effector based on the result of the comparison analysis.

Example 8. The method of any one or more of Examples 1 through 6, wherein comparing, by the processor or control circuit, the complex impedance measurement data point to a data point in a reference complex impedance characteristic pattern comprises comparing, by the processor or control circuit, the spectroscopy signature of the ultrasonic blade coupled to the ultrasonic transducer to the reference spectroscopy signature.

Example 9. The method of any one or more of Examples 1 through 6, wherein determining, by a processor or control circuit, a spectroscopy signature of the ultrasonic blade coupled to the ultrasonic transducer comprises: applying, by a drive circuit, a drive signal to the ultrasonic transducer, wherein the drive signal is a periodic signal defined by a magnitude and frequency; sweeping, by a processor or control circuit, the frequency of the drive signal from below resonance to above resonance of the electromechanical ultrasonic system; measuring and recording, by the processor or control circuit, impedance/admittance circle variables $R_e$, $G_e$, $X_e$, and $B_e$; comparing, by the processor or control circuit, the measured impedance/admittance circle variables $R_e$, $G_e$, $X_e$, and $B_e$ to reference impedance/admittance circle variables $R_{ref}$, $G_{ref}$, $X_{ref}$, and $B_{ref}$; and determining, by the processor or control circuit, a state or condition of an end effector based on the result of the comparison analysis.

Example 10. An ultrasonic surgical instrument comprising: an ultrasonic electromechanical system comprising an ultrasonic transducer coupled to an ultrasonic blade via an ultrasonic waveguide, wherein the ultrasonic electromechanical system comprises two or more components of which at least one of the two or more components is a disposable device and of which at least one of the two or more components is a reusable device; and a generator configured to supply power to the ultrasonic transducer, wherein the generator comprises a control circuit configured to: determine a spectroscopy signature of the ultrasonic blade coupled to the ultrasonic transducer; compare the spectroscopy signature to a reference spectroscopy signature; determine an installation state of the two or more components based on the comparison; and control a delivery of power to the ultrasonic transducer based on the comparison.

Example 11. The ultrasonic surgical instrument of Example 10, wherein the control circuit is further configured to enable an operation of the ultrasonic device when the installation state of the two or more components is proper.

Example 12. The ultrasonic surgical instrument of any one or more of Examples 10 through 11, wherein the control circuit is further configured to: disable an operation of the ultrasonic device when the installation state of the two or more components is not proper; and generate a warning.

Example 13. The ultrasonic surgical instrument of Example 12, wherein the warning comprises a visible warning.

Example 14. The ultrasonic surgical instrument of any one or more of Examples 12 through 13, wherein the warning comprises an audible warning.

Example 15. The ultrasonic surgical instrument of any one or more of Examples 12 through 14, wherein the warning comprises a tactile warning.

Example 16. The ultrasonic surgical instrument of any one or more of Examples 10 through 15, wherein the control circuit is further configured to: measure a complex impedance of the ultrasonic transducer, wherein the complex impedance is defined as $$Z_g(t) = \frac{V_g(t)}{I_g(t)};$$

receive a complex impedance measurement data point; compare the complex impedance measurement data point to a data point in a reference complex impedance characteristic pattern; classify the complex impedance measurement data point based on a result of the comparison analysis; and assign a state or condition of an end effector based on the result of the comparison analysis.

Example 17. The ultrasonic surgical instrument of any one or more of Examples 10 through 16, wherein the control circuit is further configured to: cause a drive circuit to apply a drive signal to the ultrasonic transducer, wherein the drive signal is a periodic signal defined by a magnitude and frequency; sweep the frequency of the drive signal from below resonance to above resonance of the electromechanical ultrasonic system; measure and record impedance/admittance circle variables $R_e$, $G_e$, $X_e$, and $B_e$; compare the measured impedance/admittance circle variables $R_e$, $G_e$, $X_e$, and $B_e$ to reference impedance/admittance circle variables $R_{ref}$, $G_{ref}$, $X_{ref}$, and $B_{ref}$; and determine a state or condition of an end effector based on the result of the comparison analysis.

Example 18. A generator for an ultrasonic surgical instrument, wherein the ultrasonic surgical instrument comprises two or more components of which at least one of the two or more components is a disposable device and of which at least one of the two or more components is a reusable device, the generator comprising: a control circuit configured to: determine a spectroscopy signature of an ultrasonic blade coupled to a ultrasonic transducer; compare the spectroscopy signature to a reference spectroscopy signature; determine an installation state of the two or more components based on the comparison; and control a delivery of power to the ultrasonic transducer based on the comparison.

Example 19. The generator for an ultrasonic surgical instrument of Example 18, wherein the control circuit is further configured to enable an operation of the ultrasonic device when the installation state of the two or more components is proper.

Example 20. The generator for an ultrasonic surgical instrument of any one or more of Examples 18 through 19, wherein the control circuit is further configured to: disable an operation of the ultrasonic device when the installation state of the two or more components is not proper; and generate a warning.

Example 21. The generator for an ultrasonic surgical instrument of Example 20, wherein the warning comprises a visible warning.

Example 22. The generator for an ultrasonic surgical instrument of any one or more of Examples 20 though 21, wherein the warning comprises an audible warning.

Example 23. The generator for an ultrasonic surgical instrument of any one or more of Examples 20 though 22, wherein the warning comprises a tactile warning.

Example 24. The generator for an ultrasonic surgical instrument of any one or more of Examples 18 through 23, wherein the control circuit is further configured to: measure a complex impedance of the ultrasonic transducer, wherein the complex impedance is defined as $$Z_g(t) = \frac{V_g(t)}{I_g(t)};$$

receive a complex impedance measurement data point; compare the complex impedance measurement data point to a data point in a reference complex impedance characteristic pattern; classify the complex impedance measurement data point based on a result of the comparison analysis; and assign a state or condition of an end effector based on the result of the comparison analysis.

Example 25. The generator for an ultrasonic surgical instrument of any one or more of Examples 18 through 24, wherein the control circuit is further configured to: cause a drive circuit to apply a drive signal to the ultrasonic transducer, wherein the drive signal is a periodic signal defined by a magnitude and frequency; sweep the frequency of the drive signal from below resonance to above resonance of the electromechanical ultrasonic system; measure and record impedance/admittance circle variables $R_e$, $G_e$, $X_e$, and $B_e$; compare the measured impedance/admittance circle variables $R_e$, $G_e$, $X_e$, and $B_e$ to reference impedance/admittance circle variables $R_{ref}$, $G_{ref}$, $X_{ref}$, and $B_{ref}$; and determine a state or condition of an end effector based on the result of the comparison analysis.

The invention claimed is:

1. An ultrasonic surgical instrument comprising:
an ultrasonic electromechanical system comprising an ultrasonic transducer coupled to an ultrasonic blade via an ultrasonic waveguide, wherein the ultrasonic electromechanical system comprises two or more components of which at least one of the two or more components is a disposable device and of which at least one of the two or more components is a reusable device; and a generator configured to supply power to the ultrasonic transducer, wherein the generator comprises a control circuit configured to:
determine a spectroscopy signature of the ultrasonic blade coupled to the ultrasonic transducer via the ultrasonic waveguide;
compare the spectroscopy signature to a reference spectroscopy signature;
determine an installation state of the two or more components based on the comparison; and
control a delivery of power to the ultrasonic transducer based on the comparison.

2. The ultrasonic surgical instrument of claim 1, wherein the control circuit is further configured to enable an operation of an ultrasonic device when the installation state of the two or more components of the two or more components is proper.

3. The ultrasonic surgical instrument of claim 1, wherein the control circuit is further configured to:
disable an operation of an ultrasonic device when the installation state of the two or more components is not proper; and
generate a warning.

4. The ultrasonic surgical instrument of claim 3, wherein the warning comprises a visible warning.

5. The ultrasonic surgical instrument of claim 3, wherein the warning comprises an audible warning.

6. The ultrasonic surgical instrument of claim 3, wherein the warning comprises a tactile warning.

7. The ultrasonic surgical instrument of claim 1, wherein the control circuit is further configured to:
measure a complex impedance of the ultrasonic transducer, wherein the complex impedance is defined as $$Z_g(t) = \frac{V_g(t)}{I_g(t)};$$

receive a complex impedance measurement data point;
compare the complex impedance measurement data point to a data point in a reference complex impedance characteristic pattern;
classify the complex impedance measurement data point based on a result of the comparison; and
assign a state or condition of an end effector based on the result of the comparison.

8. The ultrasonic surgical instrument of claim 1, wherein the control circuit is further configured to:
cause a drive circuit to apply a drive signal to the ultrasonic transducer, wherein the drive signal is a periodic signal defined by a magnitude and a frequency;
sweep the frequency of the drive signal from below resonance to above resonance of the ultrasonic electromechanical system;
measure and record impedance/admittance circle variables $R_e$, $G_e$, $X_e$, and $B_e$;
compare the measured impedance/admittance circle variables $R_e$, $G_e$, $X_e$, and $B_e$ to reference impedance/admittance circle variables $R_{ref}$, $G_{ref}$, $X_{ref}$, and $B_{ret}$; and
determine a state or condition of an end effector based on a result of the comparison.

9. A generator for an ultrasonic surgical instrument comprising an ultrasonic transducer coupled to an ultrasonic blade via an ultrasonic waveguide, wherein the ultrasonic surgical instrument comprises two or more components of which at least one of the two or more components is a disposable device and of which at least one of the two or more components is a reusable device, the generator comprising:
- a control circuit configured to:
  - determine a spectroscopy signature of the ultrasonic blade coupled to the ultrasonic transducer via the ultrasonic waveguide;
  - compare the spectroscopy signature to a reference spectroscopy signature;
  - determine an installation state of the two or more components based on the comparison; and
  - control a delivery of power to the ultrasonic transducer based on the comparison.

10. The generator for the ultrasonic surgical instrument of claim 9, wherein the control circuit is further configured to enable an operation for an ultrasonic device when the installation state of the two or more components is proper.

11. The generator for the ultrasonic surgical instrument of claim 9, wherein the control circuit is further configured to:
- disable an operation of an ultrasonic device when the installation state of the two or more components is not proper; and
- generate a warning.

12. The generator for the ultrasonic surgical instrument of claim 11, wherein the warning comprises a visible warning.

13. The generator for the ultrasonic surgical instrument of claim 11, wherein the warning comprises an audible warning.

14. The generator for the ultrasonic surgical instrument of claim 11, wherein the warning comprises a tactile warning.

15. The generator for the ultrasonic surgical instrument of claim 9, wherein the control circuit is further configured to: measure a complex impedance of the ultrasonic transducer, wherein the complex impedance is defined as $$Z_g(t) = \frac{V_g(t)}{I_g(t)};$$

- receive a complex impedance measurement data point;
- compare the complex impedance measurement data point to a data point in a reference complex impedance characteristic pattern;
- classify the complex impedance measurement data point based on a result of the comparison; and
- assign a state or condition of an end effector based on the result of the comparison.

16. The generator for the ultrasonic surgical instrument of claim 9, wherein the control circuit is further configured to:
- cause a drive circuit to apply a drive signal to the ultrasonic transducer, wherein the drive signal is a periodic signal defined by a magnitude and a frequency;
- sweep the frequency of the drive signal from below resonance to above resonance of the ultrasonic surgical instrument;
- measure and record impedance/admittance circle variables $R_e$, $G_e$, $X_e$, and $B_e$;
- compare the measured impedance/admittance circle variables $R_e$, $G_e$, $X_e$, and $B_e$ to reference impedance/admittance circle variables $R_{ref}$, $G_{ref}$, $X_{ref}$, and $B_{ref}$; and
- determine a state or condition of an end effector based on a result of the comparison.

* * * * *